United States Patent
Hsu

(10) Patent No.: US 11,034,745 B2
(45) Date of Patent: Jun. 15, 2021

(54) SUPERAGONIST POLYPEPTIDE ANALOGS OF ADRENOMEDULLIN AND INTERMEDIN PEPTIDE HORMONES

(71) Applicant: Adepthera LLC, Palo Alto, CA (US)

(72) Inventor: Sheau Yu Teddy Hsu, Menlo Park, CA (US)

(73) Assignee: Adepthera LLC, Palo Alto, CA (US)

( * ) Notice: Subject to any disclaimer, the term of this patent is extended or adjusted under 35 U.S.C. 154(b) by 37 days.

(21) Appl. No.: 16/066,609

(22) PCT Filed: Jan. 4, 2017

(86) PCT No.: PCT/US2017/012171
§ 371 (c)(1),
(2) Date: Jun. 27, 2018

(87) PCT Pub. No.: WO2017/120220
PCT Pub. Date: Jul. 13, 2017

(65) Prior Publication Data
US 2019/0010203 A1  Jan. 10, 2019

Related U.S. Application Data

(60) Provisional application No. 62/274,638, filed on Jan. 4, 2016.

(51) Int. Cl.
| | | |
|---|---|---|
| C07K 14/575 | (2006.01) | |
| C07K 19/00 | (2006.01) | |
| C07K 16/26 | (2006.01) | |
| A61K 38/00 | (2006.01) | |

(52) U.S. Cl.
CPC ...... *C07K 14/575* (2013.01); *C07K 14/57527* (2013.01); *C07K 16/26* (2013.01); *C07K 19/00* (2013.01); *A61K 38/00* (2013.01); *C07K 2319/00* (2013.01)

(58) Field of Classification Search
None
See application file for complete search history.

(56) References Cited

U.S. PATENT DOCUMENTS

| 6,239,107 B1 | 5/2001 | Gozes et al. |
|---|---|---|
| 6,268,474 B1 | 7/2001 | Smith et al. |
| 9,694,051 B2 | 7/2017 | Hsu et al. |
| 2008/0020978 A1 | 1/2008 | Gegg et al. |
| 2008/0026995 A1 | 1/2008 | Tosi et al. |
| 2008/0113411 A1 | 5/2008 | Sheffer et al. |
| 2008/0207501 A1 | 8/2008 | Erickson et al. |
| 2008/0274952 A1 | 11/2008 | Soares et al. |
| 2009/0036364 A1 | 2/2009 | Levy et al. |
| 2009/0088387 A1 | 4/2009 | Castillio et al. |
| 2009/0175821 A1 | 7/2009 | Bridon et al. |
| 2009/0186817 A1 | 7/2009 | Ghosh et al. |
| 2010/0048871 A1 | 2/2010 | Cho et al. |
| 2010/0249104 A1 | 9/2010 | Liu et al. |
| 2011/0190193 A1 | 8/2011 | Stroes |
| 2013/0281374 A1 | 10/2013 | Levy et al. |
| 2014/0155329 A1 | 6/2014 | Hsu et al. |
| 2014/0249299 A1 | 9/2014 | Levy et al. |

FOREIGN PATENT DOCUMENTS

| CN | 101035806 A | 9/2007 |
|---|---|---|
| CN | 101208099 A | 6/2008 |
| JP | H11502204 A | 2/1999 |
| JP | 2002/540216 A | 11/2002 |
| JP | 2008/507280 A | 3/2008 |
| JP | 2008/515443 A | 5/2008 |
| JP | 2014/511862 A | 5/2014 |
| WO | 1996/029432 A1 | 9/1996 |
| WO | 2004/048547 | 6/2004 |
| WO | 2006/082184 A2 | 8/2006 |
| WO | 2008/022716 A2 | 2/2008 |
| WO | 2012/138867 | 10/2012 |
| WO | 2012/138867 A2 | 10/2012 |
| WO | 2017/139154 | 8/2017 |

OTHER PUBLICATIONS

Robinson et al. (2009) "Novel Peptide Antagonists of Adrenomedullin and Calcitonin Gene-Related Peptide Receptors: Identification. Pharmacological Characterization. and Interactions with Position 74 in Receptor Activity-Modifying Protein 1/3" Journal of Pharmacology and Experimental Therapeutics., vol. 331. No. 2. pp. 513-521.
Hong et al (2012) "The pharmacology of Adrenomedullin 2/Intermedin". British Journal of Pharmacology. vol. 166. No. 1, pp. 110-120.
Woolley et al (2013) "Comparing the Molecular Pharmacology of CGRP and Adrenomedullin". Current Protein and Peptide Science. vol. 14. No. 5. pp. 358-374.
Chapter et al., "Chemical modification of Class II G-protein coupled receptor ligands: Frontiers in the developmentof peptide analogs as neuroendocrine pharmacological therapies", Pharmacal Ther, Jan. 2010, pp. 1-33, vol. 125, Issue 1, Elsevier, New York, NY.
Dasgupta et al., "Lipophilization of somatostatin analog RC-160 with long chain fatty acid improves itsantiproliferative and antiangiogenic activity in vitro", Br J Pharmacal, Jan. 2000 pp. 1-9, 129(1 ):1, MacmillanPublishers Ltd, London, United Kingdom.
Gaul T et al., "Enhanced cAMP generation and insulin-releasing potency of two novel Tyr1-modified enzyme-resistant arms of glucose-dependent insulinotropic polypeptide is associated with significant antihyperglycaemic activity in spontaneous obesity diabetes", Biochem J., Nov. 1, 2002, pp. 913-920, 367(Pt 3), Biochemical Society, London, United Kingdom.

(Continued)

*Primary Examiner* — Thomas S Heard
(74) *Attorney, Agent, or Firm* — Pamela J. Sherwood; Bozicevic, Field & Francis LLP

(57) ABSTRACT

Analogs for CLR/RAMP receptor ligands are provided that have agonist, superagonist, antagonist or superantagonist activity. The analogs can be selective for one or more CLR/RAMP receptors, or can be pan-specific.

7 Claims, 2 Drawing Sheets
Specification includes a Sequence Listing.

(56) References Cited

OTHER PUBLICATIONS

Jagadish et al., "Squalene-derived Flexible Linkers for Bioactive Peptides", Bioorg Med Chem Lett, Jun. 15, 2007, pp. 3310-3313, vol. 17, Issue 12, Elsevier, New York, NY.

Kato et al., "Adrenomedullin: A Protective Factor for Blood Vessels", Arterioscler Thromb Vase Bioi, Sep. 1, 2005, pp. 2480-2487, 25, American Heart Association, Dallas, TX.

Knudsen et al., "Potent Derivative of Glucagon-like Peptide-1 with Pharmacokinetic Properties Suitable for OnceDaily Administration", J. Med. Chem., Dec. 3, 1999, pp. 1664-1669, vol. 43, No. 9, Washington, D.C.

Kostel et al., "Purification of a lipid peptide: Method development for Hydrophobic Peptides", Conference abstract presented at ABRF in 1998.

Kubo et al., "Biological properties of adrenomedullin conjugated with polyethylene glycol", Peptides, May 5, 2014, pp. 118-127, 57, Elsevier, Philadelphia, PA.

Kurtzhals, "How to achieve a predictable basal insulin?", Diabetes Metab, 2005, pp. 4S25-4S33, 31(4 Pt 2): Elsevier, Philadelphia, PA.

Li et al., "Adrenomedullin Is Decreased in Preeclampsia Because of Failed Response to Epidermal Growth Factor and Impaired Syncytialization", Hypertension, Nov. 6, 2003, pp. 895-900, 42, American Heart Association, Dallas, TX.

Maletinska et al., "Angiotensin Analogues Palmitoylated in Positions 1 and 4", J. Med. Chem. 1997, pp. 3271-3279,40, American Chemical Society, Washington, D.C.

Meeran et al., "Circulating Adrenomedullin Does Not Regulate Systemic Blood Pressure but Increases PlasmaProlactin after Intravenous Infusion in Humans: A Pharmacokinetic Study", Journal of Clinical Endocrinology and Metabolism, Jan. 1997, pp. 95-100, 82(1), The Endocrine Society,Washington, DC.

Nagaya et al., "Adrenomedullin in the treatment of pulmonary hypertension", Peptides, Nov. 2004, pp. 2013-2018, vol. 25, Issue 11, Elsevier, New York City, NY.

Pennington, "Methods in Molecular Bology", Methods in Molecular Biology, 1994, pp. 171-185, vol. 35 PeptideSynthesis Protocols Ch 8, Site-Specific Chemical Modification Procedures,Humana Press Inc, Totowa, NJ.

Santiago et al., "Comparison of responses to adrenomedullin and adrenomedullin analogs in the mesenteric vascular bed of the cat", Eur J Pharmacal., Jan. 5, 1995, pp. 115-118, 272(1 ). Elsevier, New York City, NY.

Takahash I et al., "Adrenomedullin 2/intermedin in the hypothalamo-pituitary-adrenal axis", J Mol Neurosci, Jun. 11, 2010, pp. 182-192,43 {2), Springer Science & Business Media, LLC, New York, NY.

Wu et al., "Human vasoactive hormone adrenomedullin and its binding protein rescue experimental animals fromshock", Peptides, Feb. 28 2008, pp. 1223-1230, 29(7), Elsevier, New York City, NY.

Yang et al., "Effects of intermedin1-53 on cardiac function and ischemia/reperfusion injury in isolated rat hearts", Biochemical and Biophysical Research Communications Dec. 22, 2004, pp. 713-719, 327(3), Elsevier, New York City, NY.

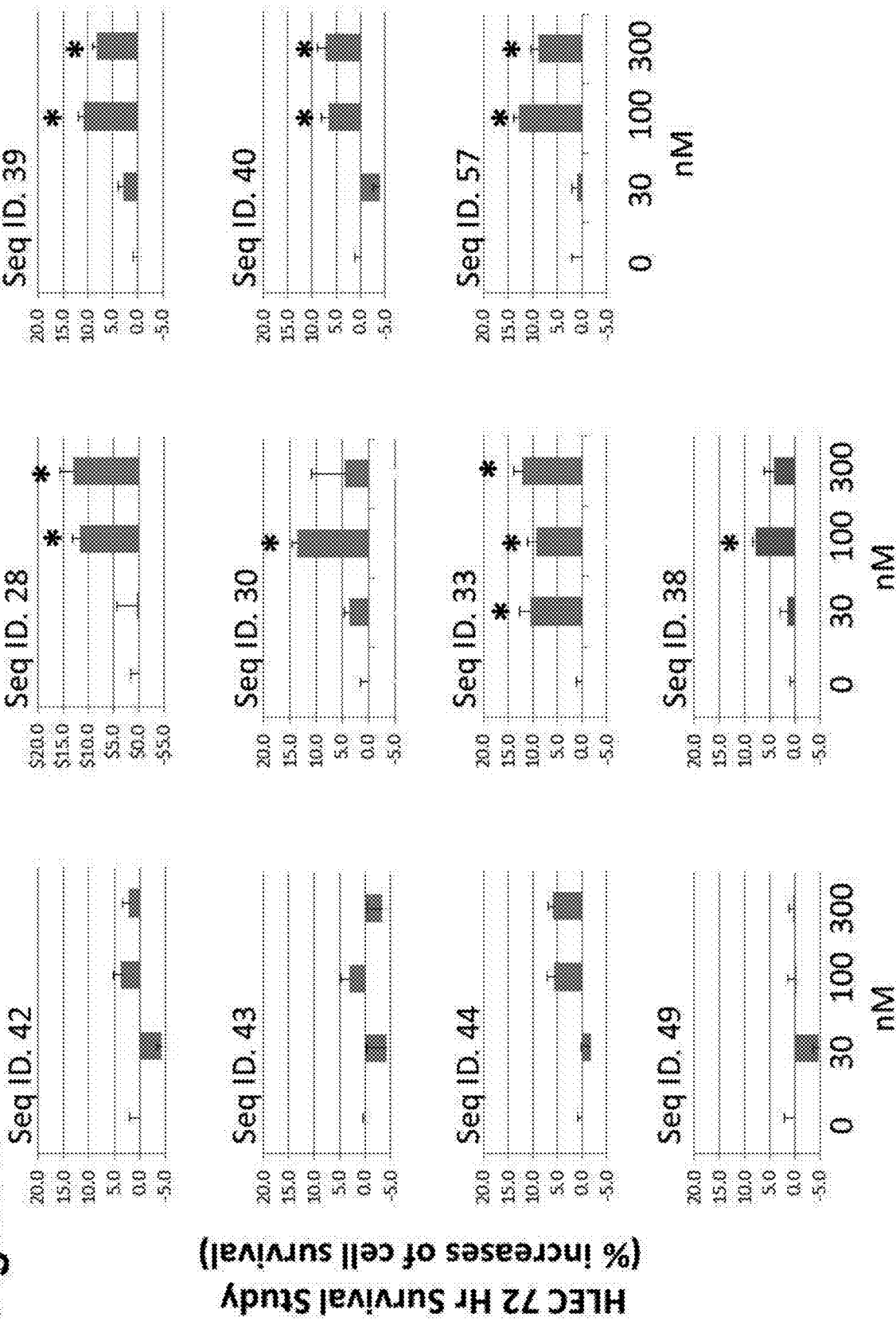

SEQUENCE LISTING

```
<160> NUMBER OF SEQ ID NOS: 144

<210> SEQ ID NO 1
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
```

```
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(22)
<223> OTHER INFORMATION: Xaa can be any naturally occurring amino acid

<400> SEQUENCE: 1

Xaa Xaa Xaa Cys Xaa Xaa Gly Xaa Cys Xaa Xaa Xaa Xaa Xaa Xaa
1               5                   10                  15

Xaa Xaa Xaa Xaa Xaa Xaa
            20

<210> SEQ ID NO 2
<211> LENGTH: 21
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid

<400> SEQUENCE: 2

Lys Gly Cys Arg Phe Gly Thr Cys Thr Val Gln Lys Leu Ala His Gln
1               5                   10                  15

Ile Tyr Gln Phe Thr
            20

<210> SEQ ID NO 3
<211> LENGTH: 20
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid

<400> SEQUENCE: 3

Lys Gly Cys Arg Phe Gly Thr Cys Thr Val Gln Lys Leu Ala His Leu
1               5                   10                  15

Trp Gln Leu Met
            20

<210> SEQ ID NO 4
<211> LENGTH: 21
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE

<400> SEQUENCE: 4
```

Lys Gly Cys Arg Phe Gly Thr Cys Thr Val Gln Lys Leu Ala His Gln
1               5                   10                  15

Ile Tyr Gln Phe Thr
            20

<210> SEQ ID NO 5
<211> LENGTH: 20
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE

<400> SEQUENCE: 5

Lys Gly Cys Arg Phe Gly Thr Cys Thr Val Gln Lys Leu Ala His Leu
1               5                   10                  15

Trp Gln Leu Met
            20

<210> SEQ ID NO 6
<211> LENGTH: 21
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (1)..(1)
<223> OTHER INFORMATION: ACETYLATION

<400> SEQUENCE: 6

Lys Gly Cys Arg Phe Gly Thr Cys Thr Val Gln Lys Leu Ala His Gln
1               5                   10                  15

Ile Tyr Gln Phe Thr
            20

<210> SEQ ID NO 7
<211> LENGTH: 20
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (1)..(1)
<223> OTHER INFORMATION: ACETYLATION

<400> SEQUENCE: 7

Lys Gly Cys Arg Phe Gly Thr Cys Thr Val Gln Lys Leu Ala His Leu
1               5                   10                  15

Trp Gln Leu Met
            20

<210> SEQ ID NO 8
<211> LENGTH: 21
<212> TYPE: PRT

-continued

```
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE

<400> SEQUENCE: 8

Lys Gly Cys Arg Phe Gly Thr Cys Thr Val Gln Lys Leu Ala His Gln
1               5                   10                  15

Ile Tyr Gln Phe Thr
            20

<210> SEQ ID NO 9
<211> LENGTH: 28
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE

<400> SEQUENCE: 9

Lys Thr Lys Lys Thr Leu Arg Thr Gly Cys Arg Phe Gly Thr Cys Thr
1               5                   10                  15

Val Gln Lys Leu Ala His Gln Ile Tyr Gln Phe Thr
            20                  25

<210> SEQ ID NO 10
<211> LENGTH: 27
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: LIPID
<222> LOCATION: (2)..(2)
<223> OTHER INFORMATION: PALMITATE

<400> SEQUENCE: 10

Thr Lys Lys Thr Leu Arg Thr Gly Cys Arg Phe Gly Thr Cys Thr Val
1               5                   10                  15

Gln Lys Leu Ala His Gln Ile Tyr Gln Phe Thr
            20                  25

<210> SEQ ID NO 11
<211> LENGTH: 27
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: LIPID
<222> LOCATION: (2)..(2)
<223> OTHER INFORMATION: PALMITATE

<400> SEQUENCE: 11

Thr Lys Lys Thr Leu Arg Thr Gly Cys Arg Phe Gly Thr Cys Thr Val
```

```
                1               5                  10                  15
Gln Lys Leu Ala His Gln Ile Tyr Gln Phe Thr
            20                  25

<210> SEQ ID NO 12
<211> LENGTH: 27
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (2)..(2)
<223> OTHER INFORMATION: PALMITATE

<400> SEQUENCE: 12

Thr Lys Lys Thr Leu Arg Thr Gly Cys Arg Phe Gly Thr Cys Thr Val
1               5                  10                  15
Gln Lys Leu Ala His Gln Ile Tyr Gln Phe Thr
            20                  25

<210> SEQ ID NO 13
<211> LENGTH: 20
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE

<400> SEQUENCE: 13

Lys Cys Arg Phe Gly Thr Cys Thr Val Gln Lys Leu Ala His Gln Ile
1               5                  10                  15
Tyr Gln Phe Thr
            20

<210> SEQ ID NO 14
<211> LENGTH: 20
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE

<400> SEQUENCE: 14

Lys Cys Arg Phe Gly Thr Cys Thr Val Gln Lys Leu Ala His Gln Ile
1               5                  10                  15
Tyr Gln Phe Thr
            20

<210> SEQ ID NO 15
<211> LENGTH: 20
<212> TYPE: PRT
```

```
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE

<400> SEQUENCE: 15

Gly Cys Arg Phe Gly Thr Cys Thr Val Gln Lys Leu Ala His Gln Ile
1               5                   10                  15

Tyr Gln Phe Thr
            20

<210> SEQ ID NO 16
<211> LENGTH: 19
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE

<400> SEQUENCE: 16

Cys Arg Phe Gly Thr Cys Thr Val Gln Lys Leu Ala His Gln Ile Tyr
1               5                   10                  15

Gln Phe Thr

<210> SEQ ID NO 17
<211> LENGTH: 12
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (1)..(12)
<223> OTHER INFORMATION: Xaa can be any naturally occurring amino acid

<400> SEQUENCE: 17

Xaa Xaa Xaa Xaa Xaa Xaa Xaa Xaa Xaa Xaa Xaa Xaa
1               5                   10

<210> SEQ ID NO 18
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 18

Asp Lys Asp Lys Asp Asn Val Ala Pro Arg Ser Lys
1               5                   10

<210> SEQ ID NO 19
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 19

Asp Lys Asp Lys Asp Asn Ser Ala Pro Val Asp Pro
1               5                   10
```

```
<210> SEQ ID NO 20
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 20

Pro Ala Gly Arg Gln Asp Ser Ala Pro Val Asp Pro
1               5                   10

<210> SEQ ID NO 21
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 21

Asp Lys Asp Lys Asp Asn Val Ala Pro Val Asp Pro
1               5                   10

<210> SEQ ID NO 22
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 22

Asp Lys Asp Lys Gln Asp Ser Ala Pro Val Asp Pro
1               5                   10

<210> SEQ ID NO 23
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 23

Asp Lys Gly Arg Gln Asp Ser Ala Pro Val Asp Pro
1               5                   10

<210> SEQ ID NO 24
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 24

Asp Lys Asp Lys Asp Ser Ala Pro Val Asp Pro
1               5                   10

<210> SEQ ID NO 25
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 25

Asp Lys Asp Lys Ser Ala Pro Val Asp Pro
1               5                   10

<210> SEQ ID NO 26
```

<211> LENGTH: 9
<212> TYPE: PRT
<213> ORGANISM: Artificial sequence
<220> FEATURE:
<223> OTHER INFORMATION: Synthetic polypeptide

<400> SEQUENCE: 26

Asp Lys Asp Ser Ala Pro Val Asp Pro
1               5

<210> SEQ ID NO 27
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: MOD_RES
<222> LOCATION: (6)..(6)
<223> OTHER INFORMATION: AMIDATION

<400> SEQUENCE: 27

Xaa Xaa Xaa Xaa Xaa Xaa
1               5

<210> SEQ ID NO 28
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 28

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
            20                  25                  30

Pro Ser Ser Pro His Ser Tyr
        35

<210> SEQ ID NO 29
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)

```
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 29

Lys Gly Cys Arg Phe Gly Thr Cys Thr Val Gln Lys Leu Ala His Gln
1               5                   10                  15

Ile Tyr Gln Phe Thr Pro Ala Gly Arg Gln Asp Ser Ala Pro Val Asp
            20                  25                  30

Pro Ser Ser Pro His Ser Tyr
        35

<210> SEQ ID NO 30
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 30

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
            20                  25                  30

Pro Ser Ser Pro His Ser Tyr
        35

<210> SEQ ID NO 31
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 31

Lys Gly Cys Arg Phe Gly Thr Cys Thr Val Gln Lys Leu Ala His Gln
1               5                   10                  15

Ile Tyr Gln Phe Thr Pro Ala Gly Arg Gln Asp Ser Ala Pro Val Asp
            20                  25                  30

Pro Ser Ser Pro His Ser Tyr
        35

<210> SEQ ID NO 32
<211> LENGTH: 39
<212> TYPE: PRT
<213> ORGANISM: Artificial sequence
<220> FEATURE:
<223> OTHER INFORMATION: Synthetic polypeptide
<220> FEATURE:
```

```
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (39)..(39)
<223> OTHER INFORMATION: AMIDATION

<400> SEQUENCE: 32

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
            20                  25                  30

Pro Ser Ser Pro His Ser Tyr
        35

<210> SEQ ID NO 33
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (39)..(39)
<223> OTHER INFORMATION: AMIDATION

<400> SEQUENCE: 33

Lys Gly Cys Arg Phe Gly Thr Cys Thr Val Gln Lys Leu Ala His Gln
1               5                   10                  15

Ile Tyr Gln Phe Thr Pro Ala Gly Arg Gln Asp Ser Ala Pro Val Asp
            20                  25                  30

Pro Ser Ser Pro His Ser Tyr
        35

<210> SEQ ID NO 34
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 34

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Val Asp
            20                  25                  30

Pro Ser Ser Pro His Ser Tyr
```

```
<210> SEQ ID NO 35
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 35

Lys Gly Cys Arg Phe Gly Thr Cys Thr Val Gln Lys Leu Ala His Gln
1               5                   10                  15

Ile Tyr Gln Phe Thr Asp Lys Asp Lys Gln Asp Ser Ala Pro Val Asp
            20                  25                  30

Pro Ser Ser Pro His Ser Tyr
        35

<210> SEQ ID NO 36
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 36

Lys Gly Cys Arg Phe Gly Thr Cys Thr Val Gln Lys Leu Ala His Gln
1               5                   10                  15

Ile Tyr Gln Phe Thr Asp Lys Gly Arg Gln Asp Ser Ala Pro Val Asp
            20                  25                  30

Pro Ser Ser Pro His Ser Tyr
        35

<210> SEQ ID NO 37
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 37

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
            20                  25                  30
```

Pro Ser Ser Pro His Ser Tyr
        35

<210> SEQ ID NO 38
<211> LENGTH: 46
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (46)..(46)
<223> OTHER INFORMATION: AMIDATION

<400> SEQUENCE: 38

Lys Thr Lys Lys Thr Leu Arg Thr Gly Cys Arg Phe Gly Thr Cys Thr
1               5                   10                  15

Val Gln Lys Leu Ala His Gln Ile Tyr Gln Phe Thr Asp Lys Asp Lys
            20                  25                  30

Asp Asn Ser Ala Pro Val Asp Pro Ser Ser Pro His Ser Tyr
        35                  40                  45

<210> SEQ ID NO 39
<211> LENGTH: 45
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: LIPID
<222> LOCATION: (2)..(2)
<223> OTHER INFORMATION: PALMITATE
<220> FEATURE:
<221> NAME/KEY: MOD_RES
<222> LOCATION: (45)..(45)
<223> OTHER INFORMATION: AMIDATION

<400> SEQUENCE: 39

Thr Lys Lys Thr Leu Arg Thr Gly Cys Arg Phe Gly Thr Cys Thr Val
1               5                   10                  15

Gln Lys Leu Ala His Gln Ile Tyr Gln Phe Thr Asp Lys Asp Lys Asp
            20                  25                  30

Asn Ser Ala Pro Val Asp Pro Ser Ser Pro His Ser Tyr
        35                  40                  45

<210> SEQ ID NO 40
<211> LENGTH: 46
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (46)..(46)
<223> OTHER INFORMATION: AMIDATION

<400> SEQUENCE: 40

```
Lys Thr Lys Lys Thr Leu Arg Thr Gly Cys Arg Phe Gly Thr Cys Thr
1               5                   10                  15

Val Gln Lys Leu Ala His Gln Ile Tyr Gln Phe Thr Asp Lys Asp Lys
            20                  25                  30

Asn Val Ala Pro Val Asp Pro Ser Ser Pro His Ser Tyr
        35                  40                  45

<210> SEQ ID NO 41
<211> LENGTH: 45
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: LIPID
<222> LOCATION: (2)..(2)
<223> OTHER INFORMATION: PALMITATE
<220> FEATURE:
<221> NAME/KEY: MOD_RES
<222> LOCATION: (45)..(45)
<223> OTHER INFORMATION: AMIDATION

<400> SEQUENCE: 41

Thr Lys Lys Thr Leu Arg Thr Gly Cys Arg Phe Gly Thr Cys Thr Val
1               5                   10                  15

Gln Lys Leu Ala His Gln Ile Tyr Gln Phe Thr Asp Lys Asp Lys Asp
            20                  25                  30

Asn Val Ala Pro Val Asp Pro Ser Ser Pro His Ser Tyr
        35                  40                  45

<210> SEQ ID NO 42
<211> LENGTH: 45
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (2)..(2)
<223> OTHER INFORMATION: PALMITATE
<220> FEATURE:
<221> NAME/KEY: MOD_RES
<222> LOCATION: (45)..(45)
<223> OTHER INFORMATION: ACETYLATION

<400> SEQUENCE: 42

Thr Lys Lys Thr Leu Arg Thr Gly Cys Arg Phe Gly Thr Cys Thr Val
1               5                   10                  15

Gln Lys Leu Ala His Gln Ile Tyr Gln Phe Thr Asp Lys Asp Lys Asp
            20                  25                  30

Asn Val Ala Pro Val Asp Pro Ser Ser Pro His Ser Tyr
        35                  40                  45

<210> SEQ ID NO 43
<211> LENGTH: 38
<212> TYPE: PRT
<213> ORGANISM: Artificial sequence
<220> FEATURE:
```

<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (38)..(38)
<223> OTHER INFORMATION: AMIDATION

<400> SEQUENCE: 43

Lys Cys Arg Phe Gly Thr Cys Thr Val Gln Lys Leu Ala His Gln Ile
1               5                   10                  15

Tyr Gln Phe Thr Asp Lys Asp Lys Asp Asn Ser Ala Pro Val Asp Pro
            20                  25                  30

Ser Ser Pro His Ser Tyr
        35

<210> SEQ ID NO 44
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (38)..(38)
<223> OTHER INFORMATION: AMIDATION

<400> SEQUENCE: 44

Lys Cys Arg Phe Gly Thr Cys Thr Val Gln Lys Leu Ala His Gln Ile
1               5                   10                  15

Tyr Gln Phe Thr Asp Lys Asp Lys Asp Asn Ser Ala Pro Val Asp Pro
            20                  25                  30

Ser Ser Pro His Ser Tyr
        35

<210> SEQ ID NO 45
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (38)..(38)
<223> OTHER INFORMATION: AMIDATION

<400> SEQUENCE: 45

Gly Cys Arg Phe Gly Thr Cys Thr Val Gln Lys Leu Ala His Gln Ile
1               5                   10                  15

Tyr Gln Phe Thr Asp Lys Asp Lys Asp Asn Ser Ala Pro Val Asp Pro
            20                  25                  30

Ser Ser Pro His Ser Tyr
        35

```
<210> SEQ ID NO 46
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (38)..(38)
<223> OTHER INFORMATION: AMIDATION

<400> SEQUENCE: 46

Lys Gly Cys Arg Phe Gly Thr Cys Thr Val Gln Lys Leu Ala His Gln
1               5                   10                  15

Ile Tyr Gln Phe Thr Asp Lys Asp Lys Asp Ser Ala Pro Val Asp Pro
            20                  25                  30

Ser Ser Pro His Ser Tyr
        35

<210> SEQ ID NO 47
<211> LENGTH: 37
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (37)..(37)
<223> OTHER INFORMATION: AMIDATION

<400> SEQUENCE: 47

Lys Gly Cys Arg Phe Gly Thr Cys Thr Val Gln Lys Leu Ala His Gln
1               5                   10                  15

Ile Tyr Gln Phe Thr Asp Lys Asp Lys Ser Ala Pro Val Asp Pro Ser
            20                  25                  30

Ser Pro His Ser Tyr
        35

<210> SEQ ID NO 48
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
```

```
<222> LOCATION: (1)..(1)
<223> OTHER INFORMATION: PALMITATE
<220> FEATURE:
<221> NAME/KEY: MOD_RES
<222> LOCATION: (36)..(36)
<223> OTHER INFORMATION: AMIDATION

<400> SEQUENCE: 48

Lys Gly Cys Arg Phe Gly Thr Cys Thr Val Gln Lys Leu Ala His Gln
1               5                   10                  15

Ile Tyr Gln Phe Thr Asp Lys Asp Ser Ala Pro Val Asp Pro Ser Ser
            20                  25                  30

Pro His Ser Tyr
        35

<210> SEQ ID NO 49
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 49

Lys Gly Cys Arg Phe Gly Thr Cys Thr Val Gln Lys Leu Ala His Gln
1               5                   10                  15

Ile Tyr Gln Phe Thr Pro Ala Gly Arg Gln Asp Ser Ala Pro Val Asp
            20                  25                  30

Pro Ser Ser Pro His Ser Tyr
        35

<210> SEQ ID NO 50
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 50

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Val Asp
            20                  25                  30
```

```
Pro Ser Ser Pro His Ser Tyr
        35

<210> SEQ ID NO 51
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 51

Lys Gly Cys Arg Phe Gly Thr Cys Thr Val Gln Lys Leu Ala His Gln
1               5                   10                  15

Ile Tyr Gln Phe Thr Asp Lys Asp Lys Gln Asp Ser Ala Pro Val Asp
            20                  25                  30

Pro Ser Ser Pro His Ser Tyr
        35

<210> SEQ ID NO 52
<211> LENGTH: 40
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (40)..(40)
<223> OTHER INFORMATION: AMIDATION

<400> SEQUENCE: 52

Val Gly Cys Val Leu Gly Thr Cys Gln Val Gln Asn Leu Ser His Arg
1               5                   10                  15

Leu Trp Gln Leu Met Gly Pro Ala Gly Arg Gln Asp Ser Ala Pro Val
            20                  25                  30

Asp Pro Ser Ser Pro His Ser Tyr
        35                  40

<210> SEQ ID NO 53
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (39)..(39)
<223> OTHER INFORMATION: AMIDATION

<400> SEQUENCE: 53
```

```
Phe Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35
```

<210> SEQ ID NO 54
<211> LENGTH: 52
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (52)..(52)
<223> OTHER INFORMATION: AMIDATION

<400> SEQUENCE: 54

```
Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50
```

<210> SEQ ID NO 55
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (39)..(39)
<223> OTHER INFORMATION: AMIDATION

<400> SEQUENCE: 55

```
Val Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ser Ser Pro His Ser Tyr
        35
```

<210> SEQ ID NO 56
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:

```
<221> NAME/KEY: MOD_RES
<222> LOCATION: (39)..(39)
<223> OTHER INFORMATION: AMIDATION

<400> SEQUENCE: 56

Val Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
            20                  25                  30

Pro Ser Ser Pro His Ser Tyr
        35

<210> SEQ ID NO 57
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (39)..(39)
<223> OTHER INFORMATION: AMIDATION

<400> SEQUENCE: 57

Val Gly Cys Arg Phe Gly Thr Cys Thr Val Gln Lys Leu Ala His Gln
1               5                   10                  15

Ile Tyr Gln Phe Thr Pro Ala Gly Arg Gln Asp Ser Ala Pro Val Asp
            20                  25                  30

Pro Ser Ser Pro His Ser Tyr
        35

<210> SEQ ID NO 58
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (39)..(39)
<223> OTHER INFORMATION: AMIDATION

<400> SEQUENCE: 58

Val Gly Cys Arg Phe Gly Thr Cys Thr Val Gln Lys Leu Ala His Leu
1               5                   10                  15

Trp Gln Leu Met Gly Pro Ala Gly Arg Gln Asp Ser Ala Pro Val Asp
            20                  25                  30

Pro Ser Ser Pro His Ser Tyr
        35

<210> SEQ ID NO 59
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
```

<223> OTHER INFORMATION: ACETYLATION
<220> FEATURE:
<221> NAME/KEY: MOD_RES
<222> LOCATION: (39)..(39)
<223> OTHER INFORMATION: AMIDATION

<400> SEQUENCE: 59

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
                20                  25                  30

Pro Ser Ser Pro His Ser Tyr
            35

<210> SEQ ID NO 60
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (39)..(39)
<223> OTHER INFORMATION: AMIDATION

<400> SEQUENCE: 60

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Val Asp
                20                  25                  30

Pro Ser Ser Pro His Ser Tyr
            35

<210> SEQ ID NO 61
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
    trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 61

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
                20                  25                  30

Lys Ser Ser Pro His Ser Tyr
            35

<210> SEQ ID NO 62
<211> LENGTH: 39

```
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 62

Lys Gly Cys Arg Phe Gly Thr Cys Thr Val Gln Lys Leu Ala His Leu
1               5                   10                  15

Trp Gln Leu Met Gly Pro Ala Gly Arg Gln Asp Ser Ala Pro Val Asp
                20                  25                  30

Pro Ser Ser Pro His Ser Tyr
                35

<210> SEQ ID NO 63
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 63

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
                20                  25                  30

Lys Ser Ser Pro His Ser Tyr
                35

<210> SEQ ID NO 64
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 64

Lys Gly Cys Arg Phe Gly Thr Cys Thr Val Gln Lys Leu Ala His Leu
1               5                   10                  15

Trp Gln Leu Met Gly Pro Ala Gly Arg Gln Asp Ser Ala Pro Val Asp
                20                  25                  30
```

Pro Ser Ser Pro His Ser Tyr
        35

<210> SEQ ID NO 65
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 65

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ser Ser Pro His Ser Tyr
        35

<210> SEQ ID NO 66
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 66

Lys Gly Cys Arg Phe Gly Thr Cys Thr Val Gln Lys Leu Ala His Leu
1               5                   10                  15

Trp Gln Leu Met Gly Pro Ala Gly Arg Gln Asp Ser Ala Pro Val Asp
            20                  25                  30

Pro Ser Ser Pro His Ser Tyr
        35

<210> SEQ ID NO 67
<211> LENGTH: 37
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES

<222> LOCATION: (37)..(37)
<223> OTHER INFORMATION: AMIDATION

<400> SEQUENCE: 67

Cys Arg Phe Gly Thr Cys Thr Val Gln Lys Leu Ala His Gln Ile Tyr
1               5                   10                  15

Gln Phe Thr Asp Lys Asp Lys Asp Asn Ser Ala Pro Val Asp Pro Ser
            20                  25                  30

Ser Pro His Ser Tyr
        35

<210> SEQ ID NO 68
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 68

Lys Gly Cys Arg Phe Gly Thr Cys Thr Val Gln Lys Leu Ala His Gln
1               5                   10                  15

Ile Tyr Gln Phe Thr Asp Lys Gly Arg Gln Asp Ser Ala Pro Val Asp
            20                  25                  30

Pro Ser Ser Pro His Ser Tyr
            35

<210> SEQ ID NO 69
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 69

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
            35

```
<210> SEQ ID NO 70
<211> LENGTH: 46
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (46)..(46)
<223> OTHER INFORMATION: AMIDATION

<400> SEQUENCE: 70

Lys Thr Lys Lys Thr Leu Arg Thr Gly Cys Arg Phe Gly Thr Cys Thr
1               5                   10                  15

Val Gln Lys Leu Ala His Gln Ile Tyr Gln Phe Thr Asp Lys Asp Lys
                20                  25                  30

Asp Asn Val Ala Pro Arg Ser Lys Ile Ser Pro Gln Gly Tyr
            35                  40                  45

<210> SEQ ID NO 71
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (38)..(38)
<223> OTHER INFORMATION: AMIDATION

<400> SEQUENCE: 71

Gly Cys Arg Phe Gly Thr Cys Thr Val Gln Lys Leu Ala His Gln Ile
1               5                   10                  15

Tyr Gln Phe Thr Asp Lys Asp Lys Asp Asn Val Ala Pro Arg Ser Lys
                20                  25                  30

Ile Ser Pro Gln Gly Tyr
            35

<210> SEQ ID NO 72
<211> LENGTH: 52
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (52)..(52)
<223> OTHER INFORMATION: AMIDATION

<400> SEQUENCE: 72

Tyr Arg Gln Ser Met Asn Asn Phe Gln Gly Leu Arg Ser Phe Gly Cys
1               5                   10                  15
```

-continued

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 73
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 73

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 74
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (38)..(38)
<223> OTHER INFORMATION: AMIDATION

<400> SEQUENCE: 74

Lys Gly Cys Asp Thr Ala Thr Cys Val Thr His Arg Leu Ala Gly Leu
1               5                   10                  15

Leu Ser Arg Ser Gly Gly Val Val Lys Asn Asn Phe Val Pro Thr Asn
            20                  25                  30

Val Gly Ser Lys Ala Phe
        35

<210> SEQ ID NO 75
<211> LENGTH: 31
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:

```
<221> NAME/KEY: MOD_RES
<222> LOCATION: (31)..(31)
<223> OTHER INFORMATION: AMIDATION

<400> SEQUENCE: 75

Thr Val Gln Lys Leu Ala His Gln Ile Tyr Gln Phe Thr Asp Lys Asp
1               5                   10                  15

Lys Asp Asn Val Ala Pro Arg Ser Lys Ile Ser Pro Gln Gly Tyr
            20                  25                  30

<210> SEQ ID NO 76
<211> LENGTH: 31
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (31)..(31)
<223> OTHER INFORMATION: AMIDATION

<400> SEQUENCE: 76

Thr Val Gln Lys Leu Ala His Gln Ile Tyr Gln Phe Thr Asp Lys Asp
1               5                   10                  15

Lys Asp Asn Ser Ala Pro Val Asp Pro Ser Ser Pro His Ser Tyr
            20                  25                  30

<210> SEQ ID NO 77
<211> LENGTH: 31
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (31)..(31)
<223> OTHER INFORMATION: AMIDATION

<400> SEQUENCE: 77

Thr Val Gln Lys Leu Ala His Gln Ile Tyr Gln Phe Thr Asp Lys Asp
1               5                   10                  15

Lys Asp Asn Ser Ala Pro Val Asp Pro Ser Ser Pro His Ser Tyr
            20                  25                  30

<210> SEQ ID NO 78
<211> LENGTH: 31
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (31)..(31)
```

<223> OTHER INFORMATION: AMIDATION

<400> SEQUENCE: 78

Lys Val Gln Lys Leu Ala His Gln Ile Tyr Gln Phe Thr Asp Lys Asp
1               5                   10                  15

Lys Asp Asn Ser Ala Pro Val Asp Pro Ser Ser Pro His Ser Tyr
            20                  25                  30

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

```
<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (36)..(36)
<223> OTHER INFORMATION: AMIDATION

<400> SEQUENCE: 92

Lys Gly Cys Arg Phe Gly Thr Cys Thr Val Gln Lys Leu Ala His Gln
1               5                   10                  15

Ile Tyr Gln Phe Thr Asp Lys Asp Ser Ala Pro Val Asp Pro Ser Ser
            20                  25                  30

Pro His Ser Tyr
        35

<210> SEQ ID NO 93
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (36)..(36)
<223> OTHER INFORMATION: AMIDATION

<400> SEQUENCE: 93

Lys Gly Cys Arg Phe Gly Thr Cys Thr Val Gln Lys Leu Ala His Gln
1               5                   10                  15

Ile Tyr Gln Phe Thr Asp Lys Asp Ser Ala Pro Val Asp Pro Ser Ser
            20                  25                  30

Pro His Ser Tyr
        35

<210> SEQ ID NO 94
<211> LENGTH: 36
```

<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (36)..(36)
<223> OTHER INFORMATION: AMIDATION

<400> SEQUENCE: 94

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Asp Pro Ser Ser
            20                  25                  30

Pro His Ser Tyr
        35

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 36
<212> TYPE: PRT
<213> ORGANISM: Artificial sequence
<220> FEATURE:
<223> OTHER INFORMATION: Synthetic polypeptide
<220> FEATURE:

```
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (36)..(36)
<223> OTHER INFORMATION: AMIDATION

<400> SEQUENCE: 101

Lys Gly Cys Arg Phe Gly Thr Cys Thr Val Gln Lys Leu Ala His Gln
 1               5                  10                  15

Ile Tyr Gln Phe Thr Asp Lys Asp Val Ala Pro Arg Ser Lys Ile Ser
            20                  25                  30

Pro Gln Gly Tyr
            35

<210> SEQ ID NO 102

<400> SEQUENCE: 102

000

<210> SEQ ID NO 103
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (36)..(36)
<223> OTHER INFORMATION: AMIDATION

<400> SEQUENCE: 103

Lys Gly Cys Arg Phe Gly Thr Cys Thr Val Gln Lys Leu Ala His Gln
 1               5                  10                  15

Ile Tyr Gln Phe Thr Asp Lys Asp Val Ala Pro Arg Ser Lys Ile Ser
            20                  25                  30

Pro Gln Gly Tyr
            35

<210> SEQ ID NO 104
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (38)..(38)
<223> OTHER INFORMATION: AMIDATION

<400> SEQUENCE: 104

Ala Cys Asp Thr Ala Thr Cys Val Thr His Arg Leu Ala Gly Leu Leu
 1               5                  10                  15
```

```
Ser Arg Phe Thr Asp Lys Asp Lys Asp Asn Val Ala Pro Arg Ser Lys
            20                  25                  30

Ile Ser Pro Gln Gly Tyr
        35

<210> SEQ ID NO 105
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 105

Phe Gly Cys Arg Phe Gly Thr Cys Thr Val Gln Lys Leu Ala His Arg
1               5                   10                  15

Leu Trp Gln Leu Met Gly Pro Asp Lys Asp Asn Val Ala Pro Arg Ser
            20                  25                  30

Lys Ile Ser Pro Gln Gly Tyr
        35

<210> SEQ ID NO 106

<400> SEQUENCE: 106

000

<210> SEQ ID NO 107

<400> SEQUENCE: 107

000

<210> SEQ ID NO 108
<211> LENGTH: 34
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (34)..(34)
<223> OTHER INFORMATION: AMIDATION

<400> SEQUENCE: 108

Ala Cys Asp Thr Ala Thr Cys Val Thr His Arg Leu Ala Gly Leu Leu
1               5                   10                  15

Ser Arg Ser Gly Gly Val Asn Phe Val Pro Thr Asn Val Gly Ser Lys
            20                  25                  30

Ala Phe

<210> SEQ ID NO 109

<400> SEQUENCE: 109

000
```

```
<210> SEQ ID NO 110
<211> LENGTH: 35
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (35)..(35)
<223> OTHER INFORMATION: AMIDATION

<400> SEQUENCE: 110

Lys Gly Cys Arg Phe Gly Thr Cys Thr Val Gln Lys Leu Ala His Gln
1               5                   10                  15

Ile Tyr Gln Phe Thr Asp Lys Asp Ala Pro Val Asp Pro Ser Ser Pro
            20                  25                  30

His Ser Tyr
        35

<210> SEQ ID NO 111

<400> SEQUENCE: 111

000

<210> SEQ ID NO 112
<211> LENGTH: 28
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (28)..(28)
<223> OTHER INFORMATION: AMIDATION

<400> SEQUENCE: 112

Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25

<210> SEQ ID NO 113

<400> SEQUENCE: 113

000

<210> SEQ ID NO 114
<211> LENGTH: 22
<212> TYPE: PRT
<213> ORGANISM: Artificial sequence
<220> FEATURE:
<223> OTHER INFORMATION: Synthetic polypeptide
<220> FEATURE:
```

```
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (22)..(22)
<223> OTHER INFORMATION: AMIDATION

<400> SEQUENCE: 114

Lys Val Gln Lys Leu Ala His Gln Ile Tyr Ser Ala Pro Val Asp Pro
1               5                   10                  15

Ser Ser Pro His Ser Tyr
            20

<210> SEQ ID NO 115
<211> LENGTH: 31
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (31)..(31)
<223> OTHER INFORMATION: AMIDATION

<400> SEQUENCE: 115

Val Thr His Arg Leu Ala Gly Leu Leu Ser Arg Phe Thr Asp Lys Asp
1               5                   10                  15

Lys Asp Asn Val Ala Pro Arg Ser Lys Ile Ser Pro Gln Gly Tyr
            20                  25                  30

<210> SEQ ID NO 116
<211> LENGTH: 31
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (31)..(31)
<223> OTHER INFORMATION: AMIDATION

<400> SEQUENCE: 116

Thr Val Gln Lys Leu Ala His Arg Leu Trp Gln Leu Met Gly Pro Asp
1               5                   10                  15

Lys Asp Asn Val Ala Pro Arg Ser Lys Ile Ser Pro Gln Gly Tyr
            20                  25                  30

<210> SEQ ID NO 117
<211> LENGTH: 31
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
```

```
<223> OTHER INFORMATION: PALMITATE
<220> FEATURE:
<221> NAME/KEY: MOD_RES
<222> LOCATION: (31)..(31)
<223> OTHER INFORMATION: AMIDATION

<400> SEQUENCE: 117

Val Thr His Arg Leu Ala Gly Leu Leu Ser Arg Phe Thr Asp Lys Asp
1               5                   10                  15

Lys Asp Asn Val Ala Pro Arg Ser Lys Ile Ser Pro Gln Gly Tyr
            20                  25                  30

<210> SEQ ID NO 118
<211> LENGTH: 31
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (31)..(31)
<223> OTHER INFORMATION: AMIDATION

<400> SEQUENCE: 118

Thr Val Gln Lys Leu Ala His Arg Leu Trp Gln Leu Met Gly Pro Asp
1               5                   10                  15

Lys Asp Asn Val Ala Pro Arg Ser Lys Ile Ser Pro Gln Gly Tyr
            20                  25                  30

<210> SEQ ID NO 119
<211> LENGTH: 28
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (28)..(28)
<223> OTHER INFORMATION: AMIDATION

<400> SEQUENCE: 119

Lys Val Gln Lys Leu Ala His Gln Ile Tyr Gln Phe Thr Asp Lys Asp
1               5                   10                  15

Val Ala Pro Arg Ser Lys Ile Ser Pro Gln Gly Tyr
            20                  25

<210> SEQ ID NO 120
<211> LENGTH: 29
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (29)..(29)
<223> OTHER INFORMATION: AMIDATION

<400> SEQUENCE: 120
```

```
Lys Val Gln Asn Leu Ser His Arg Leu Trp Gln Leu Met Gly Pro Ala
1               5                   10                  15

Gly Ser Ala Pro Val Asp Pro Ser Ser Pro His Ser Tyr
            20                  25
```

<210> SEQ ID NO 121
<211> LENGTH: 28
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (28)..(28)
<223> OTHER INFORMATION: AMIDATION

<400> SEQUENCE: 121

```
Lys Val Gln Lys Leu Ala His Gln Ile Tyr Gln Phe Thr Asp Lys Asp
1               5                   10                  15

Ser Ala Pro Val Asp Pro Ser Ser Pro His Ser Tyr
            20                  25
```

<210> SEQ ID NO 122
<211> LENGTH: 22
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (22)..(22)
<223> OTHER INFORMATION: AMIDATION

<400> SEQUENCE: 122

```
Lys Val Gln Lys Leu Ala His Gln Ile Tyr Ser Ala Pro Val Asp Pro
1               5                   10                  15

Ser Ser Pro His Ser Tyr
            20
```

<210> SEQ ID NO 123
<211> LENGTH: 21
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (21)..(21)
<223> OTHER INFORMATION: AMIDATION

<400> SEQUENCE: 123

```
Lys Val Gln Lys Leu Ala His Gln Ile Ser Ala Pro Val Asp Pro Ser
1               5                   10                  15

Ser Pro His Ser Tyr
            20
```

```
<210> SEQ ID NO 124
<211> LENGTH: 20
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (20)..(20)
<223> OTHER INFORMATION: AMIDATION

<400> SEQUENCE: 124

Lys Val Gln Lys Leu Ala His Gln Ser Ala Pro Val Asp Pro Ser Ser
1               5                   10                  15

Pro His Ser Tyr
            20

<210> SEQ ID NO 125
<211> LENGTH: 27
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (27)..(27)
<223> OTHER INFORMATION: AMIDATION

<400> SEQUENCE: 125

Lys Val Gln Lys Leu Ala His Gln Ile Tyr Gln Phe Thr Asp Lys Ser
1               5                   10                  15

Ala Pro Val Asp Pro Ser Ser Pro His Ser Tyr
            20                  25

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130
```

```
<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137
<211> LENGTH: 30
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (30)..(30)
<223> OTHER INFORMATION: AMIDATION

<400> SEQUENCE: 137

Val Thr His Arg Leu Ala Gly Leu Leu Ser Arg Ser Gly Gly Val Val
1               5                   10                  15

Lys Asn Asn Phe Val Pro Thr Asn Val Gly Ser Lys Ala Phe
            20                  25                  30

<210> SEQ ID NO 138

<400> SEQUENCE: 138

000

<210> SEQ ID NO 139
```

```
<211> LENGTH: 17
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (17)..(17)
<223> OTHER INFORMATION: AMIDATION

<400> SEQUENCE: 139

Lys Val Gln Lys Leu Ser Ala Pro Val Asp Pro Ser Ser Pro His Ser
1               5                   10                  15

Tyr

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143
<211> LENGTH: 37
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (37)..(37)
<223> OTHER INFORMATION: AMIDATION

<400> SEQUENCE: 143

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
                20                  25                  30

Gly Ser Lys Ala Phe
            35

<210> SEQ ID NO 144
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 144

Lys Thr Lys Lys Thr Leu Arg Thr
1               5
```

SUPERAGONIST POLYPEPTIDE ANALOGS OF ADRENOMEDULLIN AND INTERMEDIN PEPTIDE HORMONES

CROSS REFERENCE

This application is a 371 application and claims the benefit of PCT Application No. PCT/US2017/012171, filed Jan. 4, 2017, which claims benefit of U.S. Provisional Patent Application No. 62/274,638, filed Jan. 4, 2016, which applications are incorporated herein by reference in their entirety.

FIELD OF THE INVENTION

The present embodiments relate to superagonists and superantagonists of the adrenomedullin (ADM)/calcitonin gene-related peptide (CGRP)/intermedin (adrenomedullin 2, IMD) family of peptide hormones and therapeutic uses thereof.

BACKGROUND OF THE INVENTION

G protein-coupled receptors (GPCRs) are cell surface receptors and represent one of the largest protein families in the human genome. Based on phylogenetic criteria, the large superfamily of human GPCRs can be subdivided into the five main subfamilies: Glutamate, Rhodopsin, Adhesion, Frizzled/Taste and Secretin ('GRAFS' nomenclature), among which the Secretin family (resembling the class B GPCR family in the Kolakowski/NC-IUPHAR extended nomenclature system) is among the most studied subclass. So far, more than one-third of all drugs target GPCRs.

The canonical view of GPCR signal transduction is focused on the activation of intracellular heterotrimeric guanine nucleotide binding proteins (G proteins)(Lagerstrom et al. (2008) Nat Rev Drug Discov; 7:339-357). The ability of a ligand to elicit a receptor-mediated cellular response is addressed by the term 'efficacy' (Kenakin (2013) Br J Pharmacol 168:554-575; Rajagopal (2013) Nat Rev Drug Discov 12:483). Historically, the efficacy of a ligand is derived from concentration-effect curves and quantified by the efficacy concentration (EC50) and maximum effect ($E_{max}$) relative to $E_{max}$ of a standard compound such as the endogenous ligands (Langmead and Christopoulos (2013) Br J Pharmacol 169:353-356).

Drugs that induce the maximum response in a system may nevertheless differ in efficacy, because the fraction of receptors required to be agonist-bound can depend on the individual efficacy for receptor activation. Therefore, the response usually has a certain assay-dependent limit. GPCR ligands are usually classified according to their efficacy, i.e. the ability to elicit a receptor-mediated pharmacological response (Smith et al. (2011) Mol Cell Endocrinol 331:241-247).

Crystallographic efforts with GPCRs in their active state show that both agonist binding and binding of a G protein are important to capture the protein in a fully active state (Rasmussen et al. (2011) Nature 477:549-555). Moreover, recent studies show that GPCR agonists stabilize only a subset of possible conformational states (Kobilka and Deupi (2007) Trends Pharmacol Sci 28:397-406; Kenakin (2013) Br J Pharmacol 168:554-575). Therefore, diverse agonists of a given receptor protein may stabilize different subsets of conformations with distinct efficacies for the activation of specific signaling pathways (Kenakin (2013) Br J Pharmacol 168:554-575). Therefore, a 'strong' agonist could populate a set of conformations similar to the more uniform and fully active conformation generated by a highly efficacious agonist.

Consequently, supraphysiological efficacy of compounds stabilizing a more uniform conformation than the endogenous agonist represents a superagonist (Schrage et al. (2015) Br J Pharmacol doi: 10.1111/bph.13278). In the largest and most 'druggable' class of GPCRs (the rhodopsin-like class or class A), a few synthetic compounds have been described to exhibit greater intrinsic efficacy than the endogenous ligands. These compounds include those for Somatostatin sst4 receptor, ghrelin receptor, a2A-adrenoceptor, Thyrotropin-releasing hormone TRH1 receptor, and Muscarinic M2 cholinoceptor (Schrage et al. (2015) Br J Pharmacol doi: 10.1111/bph.13278). There are examples (Carlier et al. (2002) Bioorg Med Chem Lett 12:1985-1988; Ihara et al. (2004) Biosci Biotechnol Biochem 68:761-763) for supraphysiological agonist efficacy at ligand-gated ion channels as well. Examples include the GABA receptors.

The ADM/CGRP/IMD peptide family includes calcitonin gene-related peptides (CGRPα and CGRPβ), adrenomedullin (ADM), intermedin (IM), calcitonin (CT) and amylin. Among them, CGRPs, ADM and IMD are structurally similar and signal through receptor complexes consisting of two transmembrane components, the calcitonin receptor-like receptor (CLR) and one of the three receptor activity-modifying proteins (RAMP1, 2, and 3). Co-expression of the calcitonin receptor-like receptor (CLR) and receptor activity-modifying proteins (RAMPs) is required to generate functional receptors for CGRPs, ADM and IMD. Whereas CGRPs mainly act through the CLR/RAMP1 receptor, ADM has high affinity for CLR/RAMP2 and 3 receptors. On the other hand, IMD exhibits no distinct preference for the three CLR/RAMP receptors.

The 52-amino-acid ADM is produced in adrenal gland, lung, kidney, heart muscle and other organs; whereas CGRP peptides are neurotransmitters. The plasma levels of ADM, CGRPs, and IMD are in the picomolar range. Activation of the CLR/RAMP receptors leads to intracellular elevation of adenosine 3', 5'-cyclic monophosphate (cAMP) in the receptor-bearing cells. CLR/RAMP receptors are present on different cell types in almost all organs including endothelial cells. These peptides are thought to be metabolized by neutral endopeptidase and are predominantly cleared by the kidney, or in the lung where CLR/RAMP receptors are highly expressed [Gibbons C, Dackor R, Dunworth W, Fritz-Six K, Caron K M, Mol Endocrinol 21(4), 783-796 (2007)].

Although ADM and IMD were first characterized as potent vasotone regulators, subsequent investigations have revealed that the functions of these peptides go far beyond the hypotensive effects, and they exhibit pleiotropic effects in a variety of organs. Studies of transgenic mice have shown that ADM, CLR, and RAM P2 are essential for normal development of blood and lymphatic vasculatures during embryonic development and adulthood. Infusion of ADM or IMD has been shown to reduce vasoconstriction, peripheral vascular resistance, and edema, and to increase cardiac output and renal glomerular filtration in animals. These peptides have also been shown to have beneficial effects on heart failure and myocardial infarction in humans, sheep, and rodents; pulmonary arterial hypertension in humans, pigs, and rats. Furthermore, it is generally accepted that ADM and IMD are counter-regulatory hormones that are increased in diseased state as a compensatory response to injury and hypoxia. In addition, ADM has been shown to ameliorate acute or chronic lung injuries induced by lipopolysaccharide (LPS), elastase, monocrotaline, bleomycin, ischemia-reperfusion, and carrageenan in a variety of animal models.

In addition, exogenous ADM and IMD have been shown to stimulate the proliferation and migration of endothelial and lymphendothelial cells in vitor as well as to revascularize damaged lymphatic and blood vessels in a variety of animal models. Furthermore, these hormones exhibit neuroprotective, renoprotective, diuresis and/or natriuresis effects in animals with heart failure, myocardial infarction, stroke, resistant hypertension, pulmonary arterial hypertension, preeclampsia, secondary lymphedema, and diabetic ulcer, by improving endothelial cell survival, angiogenesis and vascular integrity, cardiac output, and renal glomerular filtration. Moreover, ADM can mobilize and enhance the survival, differentiation, and the angiogenic potency of a variety of stem/progenitor cells.

CGRPs are sensory neuropeptides with potent vasodilatory, cardiotonic, and pain transmission action as described in U.S. Pat. No. 4,530,838 to Evans, et al. CGRP is present in both the central and peripheral nervous systems and is concentrated in those areas of the body receiving sensory input from the dorsal horn with limited amounts associated with autonomic input. In the brain, the peptide is present in the nuclei of sensory and motor cranial nerves and in cell bodies in the hypothalamus, preoptic area, ventromedial thalamus, hippocampus, and the like (Poyner, D. 1992, Pharmac. Ther. 56:23-51).

In addition, ADM/CGRP/IMD family peptides are known to have potent stimulatory effects on the proliferation of endothelial cells that serve as starter materials for blood vessels, angiogenesis, and vascular remodeling. Because ADM, CGRP, and IMD are among the most potent known vasodilators in humans, these peptides may be functionally important for maintaining high flow/low resistance circulation and feto-placental tissue development during normal physiology and pregnancy.

Agonists at the receptor level to CGRP, ADM, or IMD have been postulated to be useful in pathophysiologic conditions where endothelial dysfunction, insufficient vessel development, and aberrant vasodilation regulation has occurred. CLR/RAMP receptor superagonists could be of use as a tool for stimulating vascular CLR/RAMP receptors and thus stimulating tissue regeneration in pathological conditions such as heart failure, myocardial infarction, resistant hypertension, malignant hypertension, vasospasm, stroke, vasospasm, bronchopulmonary dysplasia, pulmonary arterial hypertension, lymphedema, wound healing, acute lung injury, pressure ulcer, age-related macular degeneration, multiple sclerosis, Alzheimer's disease, Parkinson's disease, epilepsy, retinopathy, organ preservation, eclampsia, and preeclampsia.

The physiological functions of the hormone peptides in the CT/CGRP family are determined by receptor-binding specificity and the tissue expression profiles of individual ligands and their respective receptors and have been shown to be involved in cardiovascular morphogenesis, sensory neurotransmission, inflammatory reactions, nociceptive behavior and glucose homeostasis (see, e.g., Hay, et al. 2001, Trends Pharmacol. Sci. 22:57-59; Shindo, et al. 2001, Circulation 104: 1964-1971; Zhang et al. 2001, Pain 89:265-273; Salmon et al. (1999) Neuroreport 10:849-854; Salmon, et al. 2001, Nat. Neurosci. 4: 357-358; and Mulder, et al. 2000, Am. /. Physiol. 278:E684-E691).

Inhibitors at the receptor level to CGRP and ADM are postulated to be useful in pathophysiologic conditions where excessive CGRP and/or ADM receptor activation has occurred. Some of these include neurogenic vasodilation, neurogenic inflammation, migraine, cluster headache and other headaches, thermal injury, circulatory shock, menopausal flushing, and asthma. CGRP receptor activation has particularly been implicated in the pathogenesis of migraine headache (Edvinsson L. 2001, CNS Drugs 15(10):745-53; Williamson, D. J. 2001 Microsc. Res. Tech. 53: 167-178.; Grant, A. D. 2002, Brit. J Pharmacol. 135:356-362). Headache associated with migraines is thought to be a result of profound cerebral vasodilation associated with migraine events (Moskowitz 1992, Trends Pharmacol. Sci. 13:307-311). Migraine patients exhibit elevated basal CGRP levels compared to controls (Ashina, et al., 2000, Pain 86(1-2)133-8), and serum levels of CGRP are elevated during migraine (Goadsby, et al. 1990, Ann. Neurol. 28:183-7). Treatment with anti-migraine therapeutic candidates returns CGRP levels to normal coincident with alleviation of headache (Gallai, et al. 1995, Cephalalgia 15:384-90); whereas intravenous CGRP administration produces headache in migraineurs (Lassen, et al. 2002, Cephalalgia 22(1):54-61). Thus, CGRP antagonists could be useful for blocking cerebrovascular CGRP receptors and thus blocking migraine.

Both small molecule and peptide antagonists of the CGRP receptor, such as intravenous olcegepant (BIBN4096 BS, Boehringer Ingelheim) and oral telcagepant (MK-0974, Merck & Co., Inc.) have been shown to be effective in clinical trials for the treatment of migraines. (See, Tepper and Stillman, 2008, Headache 48(8): 1259-1268; and Durham and Vause 2010, CNS Drugs 24(7):539-548.) However, select small molecule CGRP antagonist such as MK-3207 has been associated with asymptomatic liver test abnormalities in some patients.

Peptide antagonists of the CGRP receptor include peptides comprising the sequence of CGRP but lacking at least the first seven amino acids of the 37-amino-acid CGRP sequence (e.g., CGRP (8-37), CGRP (28-37), [Tyr°]CGRP (28-37), CGRP (12-37), h-a-CGRP (9-37), h-a-CGRP (10-37), h-a-CGRP (11-37), [Ala 9]-h-a-CGRP (8-37), [Ala 10]-h-a-CGRP (8-37), [Ala n]-h-a-CGRP (8-37), [Ala 12]-h-a-CGRP (8-37), h-a-CGRP (19-37), h-a-CGRP (23-37) and acetyl-h-a-CGRP (19-37); Mimeault, M. et al., 1992, Med. Chem. 35:2163-2168; Rovero, P. et al. 1992, Peptides 13:1025-1027). While a number of CGRP receptor peptide antagonists have been shown to effectively compete with CGRP in vitro, these antagonists have not performed as well in in vivo models of migraine-like pathologies due to low bioactivities.

Inhibitors at the receptor level to ADM include ADM22-52. Tertiary structure analyses indicated that the binding domain of ADM family peptides is characterized by an unstructured string. Because (1) ADM acts as a mitogenic factor for tumor cells and surrounding vessels in tumors with a lung, breast, colon, brain, pancreas, endometrium, ovary, kidney, or prostate origin, (2) ADM expression in tumors is associated with the aggressiveness of tumors, distant metastasis and poor patient prognosis, and (3) blockage of CLR/RAMP receptor signaling reduces growth, microvessel density, tumor-associated macrophage-induced angiogenesis, and metastasis of tumor xenografts, CLR/RAMP2 and/or CLR/RAMP3 receptor antagonists are antiangiogenic drug candidates for cancer therapy.

Overall, four approaches have been taken to block CLR/RAMP receptor signaling. These strategies include the use of (1) synthetic peptide antagonists (e.g., CGRP8-37 and ADM22-52, which are specific for CGRP-mediated CLR/RAMP1 and ADM-mediated CLR/RAMP2 signaling, respectively), (2) small molecule CGRP receptor antagonist (e.g., telcagepant), (3) anti-ligand antibodies (e.g., anti-CGRP or anti-ADM antibody), and (4) anti-receptor antibodies (e.g., anti-CLR or anti-RAMP antibody). However, existing therapeutic candidates are associated with efficacy or safety concerns. First, peptide antagonists such as CGRP8-37 and ADM22-52 have extremely short half-lives and low potencies, and are receptor-specific. Second, the small molecule CLR/RAMP1 receptor antagonists suffer liver toxicity in humans. Third, the anti-ligand and anti-receptor antibodies are specific for one of the ligands or receptor components; therefore, they only act on a small subgroup of targets. Fourth, the antibodies have limited access to CLR/RAMP receptors in the central nervous system. Therefore, a pan-specific or CLR/RAMP receptor1-, 2-, or 3-specific super-antagonist represents excellent anti-CLR/RAMP receptor therapeutic drug candidates because peptide antagonists such as CGRP8-37 has been shown to cross the blood-brain barrier (BBB) efficiently when compared to small molecule CLR/RAMP1 antagonist and anti-CGRP antibodies. In addition, because the newly invented super-antagonists are rather lipophilic, they could have better access to the brain compartment compared to wild-type analogs.

The most widely studied CLR/RAMP receptor agonist, ADM, is known to be safe, effective and well tolerated in early clinical trials for the acute treatment of heart failure and pulmonary hypertension. However, due to limited potency of the agonist, pharmacological effect is inadequate.

Publications, each of which are herein specifically incorporated by reference, include:
Hong et al. (2012) Br J Pharmacol 166:110-120
Watkins et al. (2013) Br J Pharmacol 170:1308-1322
Booe et al. (2015) Mol Cell 58:1040-1052
Hinson et al. (2000) Endocr Rev 21:138-167 (2000)
Takei et al. (2004) FEBS Lett 556:53-58.
McLatchie et al. (1998). Nature 393: 333-339
Bell, D. & McDermott, B. J. (2008) Br J Pharmacol 153 Suppl 1, S247-262
Muff, R. et al. (1998). FEBS Lett 441, 366-368
Hay et al. (2005) Mol Pharmacol 67:1655-1665
Robinson et al. (2009) J Pharmacol Exp Ther 331:513-521
Yin et al. (2009) J Biol Chem 284:12328-12338
van Der Lee et al. (2008) J Biomol Screen 13:986-998

SUMMARY OF THE INVENTION

Compositions and methods are provided that relate to adrenomedullin and intermedin analogs that exhibit super-agonistic or superantagonist activity on CLR/RAMP receptors (i.e., CLR/RAMP1, 2, and 3). Based on the CLR/RAMP receptor signaling and a human lymphatic endothelial cell system, it is shown herein that analogs of adrenomedullin and intermedin that contain chimeric sequences and N-terminal acylation, which optionally comprise a mini-PEG moiety, exhibit superior agonistic receptor-activation activities toward CLR/RAMP1, CLR/RAMP2, and/or CLR/RAMP3 receptor in term of EC50 or maximum intrinsic activity when compared to adrenomedullin, CGRP, or intermedin. Such chimeric peptides may be referred to herein as pan-specific superagonists.

In some embodiments of the invention, adrenomedullin analogs are provided that contain N-terminal mini-PEG and acylation moieties, which analogs exhibit superagonistic activity toward CLR/RAMP2 and/or CLR/RAMP3 receptor, when compared to wild type ligands. Such analogs may be referred to herein as CLR/RAMP2-receptor specific super-agonists.

In other embodiments, antagonistic analogs comprising chimeric sequences of adrenomedullin and intermedin with N-terminal acylation are provided, which exhibit superior antagonistic activities toward CLR/RAMP1, CLR/RAMP2, and/or CLR/RAMP3 receptors in term of IC50 when compared to known CLR/RAMP receptor antagonist. Such chimeric peptides may be referred to herein as pan-specific, CLR/RAMP1-specific, or CLR/RAMP2-specific superantagonists.

Without being limited by the mechanism of action, the superagonism and superantagonism exhibited by these analogs may in part be explained by the formation of stable ligand-receptor complex when compared to wild type ligands.

It has been surprisingly found that certain select amino acids in the N-terminal portion of the ADM and in the C-terminal portion of the intermedin, as disclosed and described herein, are responsible for the specificity and potency of peptide agonist activity. It is shown herein that substituting certain amino acids and modification in the N-terminal portion of the ADM can tune the activity from a normal agonist to a superagonist of CLR/RAMP receptors. Additional substitutions or modifications can provide additional desirable characteristics to the peptides of the present invention.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 2. Stimulation of human lymphatic endothelial cell survival in medium with 0.1% FBS by superagonists. Treatments of the primary human lymphatic endothelia cells (HLEC) with superagonists of CLR/RAMP receptors (SEQ ID NOS: 28, 30, 33, 38, 39, 40, and 69) significantly promote the HLEC survival at nanomolar ranges. For in vitro cell survival assay, HLECs were incubated in endothelial cell basal medium supplemented with 0.1% fetal bovine serum (FBS) and different concentrations of the agonist (30, 100, and 300 nM). The cells were cultured for 72 hrs, and cell viability was assayed with the MTS assay (Promega). By contrast, the normal agonists (SEQ ID NOS: 52, 53, 54, and 59) have negligible effects on HLEC proliferation under

DETAILED DESCRIPTION OF THE EMBODIMENTS

Definitions

Figure 1:
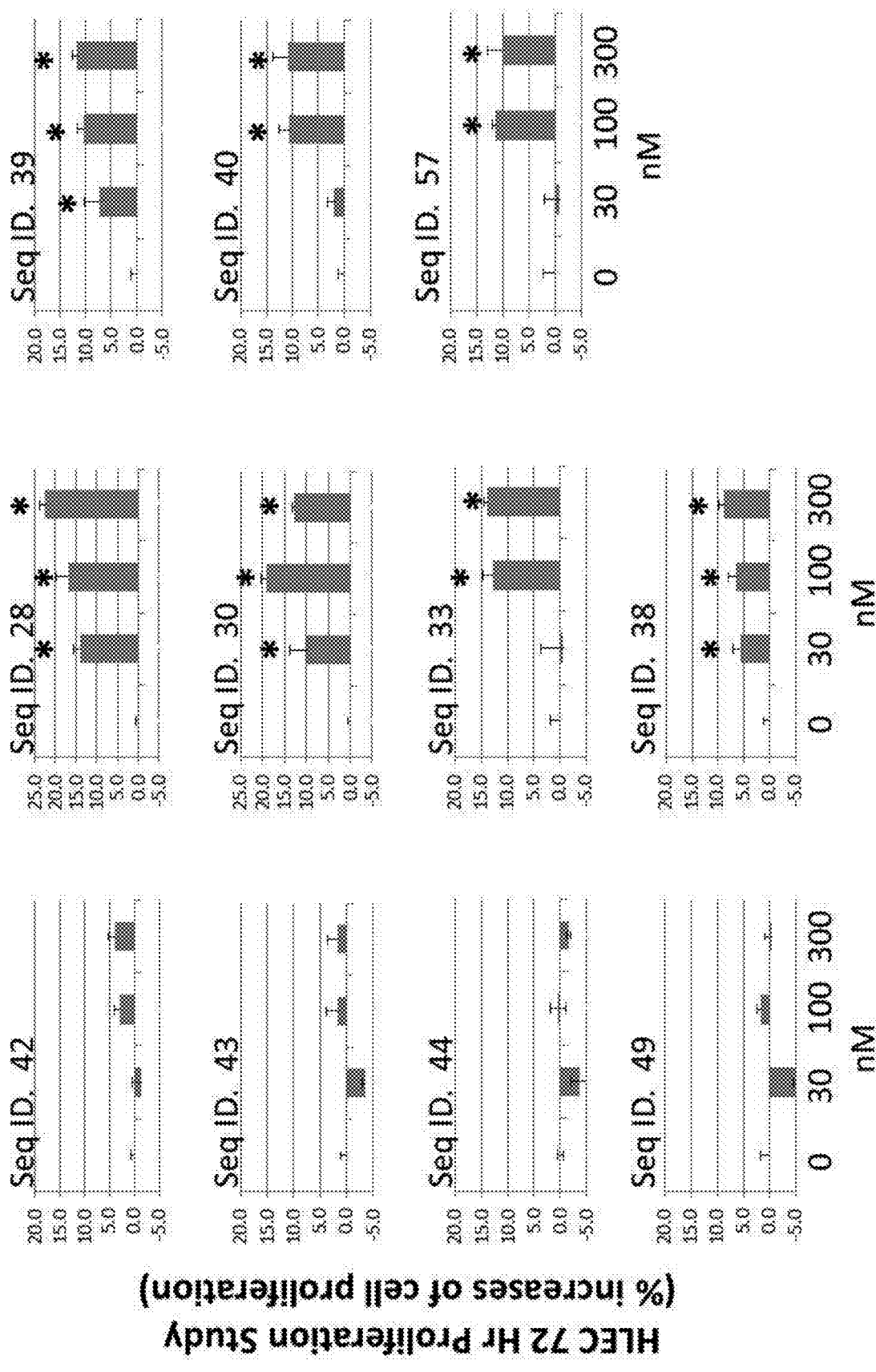
FIG. 1. Stimulation of human lymphatic endothelial cell proliferation in medium with 2% FBS by superagonists. Treatments of the primary human lymphatic endothelia cells (HLEC) with superagonists of CLR/RAMP receptors (SEQ ID NOS: 28, 30, 33, 38, 39, 40, and 69) significantly promote the HLEC proliferation at nanomolar ranges. For in vitro cell growth assay, HLECs were incubated in endothelial cell basal medium supplemented with 2% fetal bovine serum (FBS) and different concentrations of the agonist (30, 100, and 300 nM). The cells were cultured for 72 hrs, and cell viability was assayed with the MTS assay (Promega). By contrast, the normal agonists (SEQ ID NOS: 52, 53, 54, and 59) have negligible effects on HLEC proliferation under identical culture condition. Significant differences in % of cell proliferation are indicated by asterisks above the bar graph.

The following definitions are set forth to illustrate and define the meaning and scope of the various terms used to describe the embodiments.

As used herein, "agonist" refers to a biologically active ligand that binds to its complementary biologically active receptor and activates the latter either to cause a biological response in the receptor or to enhance preexisting biological activity of the receptor. An antagonist refers to a biologically active ligand that binds to a biologically active receptor and decreases the response. As used herein, "antagonist" refers to a biologically active ligand which inhibits the physiological response of the receptor.

As used herein, a superagonist is an agonist that has a greater biological activity than the native ligand, including without limitation the wild-type human intermedin, adrenomedullin or calcitonin gene-related peptide (CGRP). Reference may be made to the activity of a specific ligand/receptor pair, for example the calcitonin receptor-like receptor (CLR) and one of the three receptor activity-modifying proteins (RAMP1, 2, and 3). Co-expression of the calcitonin receptor-like receptor (CLR) and receptor activity-modifying proteins (RAMPs) is required to generate functional receptors for CGRPs, ADM and IMD. Whereas CGRPs mainly act through the CLR/RAMP1 receptor, ADM has high affinity for CLR/RAMP2 and 3 receptors. IMD exhibits no distinct preference for the three CLR/RAMP receptors. A peptide may be a superagonist for a specific receptor, relative to the native ligand for the receptor, or may be a superagonist with respect to multiple receptors, and any native ligand for one of the receptors.

In some embodiments a superagonist has activity that is greater than about 105%, 110%, 125%, 150%, 175%, 2-fold, 3-fold, 5-fold or more relative to a native ligand for the receptor or receptors.

Specific superagonist. A specific superagonist has high activity for a selected receptor, where the superagonist may be greater than about 5-fold, greater than about 10-fold, greater than about 20-fold or more, active against one member of the CLR/RAMP receptor family. In some embodiments a superagonist is specific for CLR/RAMP1 relative to CLR/RAMP2. In other embodiments a superagonist is specific for CLR/RAMP2 relative to CLR/RAMP1.

A superantagonist, or antagonist herein inhibits the biological activity of one or more receptors, particularly a receptor activated by ADM, IMD and CGRPs. A superantagonist may inhibit the activity to a degree greater than the inhibition of a native ligand. An antagonist or superantagonist may inhibit receptor activity by 105%, 110%, 125%, 150%, 175%, 2-fold, 3-fold, 5-fold or more, for example in the presence of a native ligand. A superantagonist or antagonist may be pan-specific.

A pan-specific superagonist, agonist, or antagonist has activity for two or more receptors. In some embodiments the receptors include two or more of CLR/RAMP1, CLR/RAMP2 and CLR/RAMP3. In some embodiments the receptors are CLR/RAMP1, CLR/RAMP2 and/or CLR/RAMP3.

Mini-peg. A mini-PEG moiety may be defined as CAS number: 166108-71-0; Fmoc-NH-(PEG)-COOH, or Fmoc-8-amino-3,6-dioxaoctanoic acid; Molecular weight: 385.42 g/mol; having a structure:

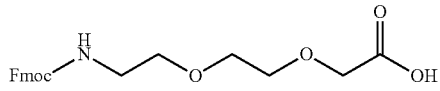

In a coupling reaction, mini-PEG behaves similarly to amino acids: the free acid end of mini-PEG will react with free amino group of the last N-terminus amino acid (in our case, the Lys residue) to form a peptide bond. In the following deprotecting procedure, the protecting group Fmoc was cleaved off to expose the free amino group of mini-PEG.

Native adrenomedullin, intermedin or calcitonin gene-related peptide (CGRP). As used herein, the term refers to the common wild-type counterparts of these peptides as known in the art. Included are the wild-type human peptides, although other mammalian counterparts may also find use, e.g. non-human primates, apes, canines, equines, murines, felines, lagomorphs, bovines, ovines, porcines, and the like.

As used herein, "pharmaceutically acceptable salt" refers to the non-toxic alkali metal, alkaline earth metal, and ammonium salts commonly used in the pharmaceutical industry including the sodium, potassium, lithium, calcium, magnesium, barium, ammonium, and protamine zinc salts. The term also includes non-toxic acid addition salts, which are generally prepared by reacting the CLR/RAMP receptor superagonists disclosed herein with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like. Thus, the term refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable salts as prodrugs, see Bundgaard, H. ed., 1985 *Design of Prodrugs,* Elsevier Science Publishers, Amsterdam.

As used herein, "pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H. ed. 1985 *Design of Prodrugs,* Elsevier Science Publishers, Amsterdam. The alcohol component of the ester will generally comprise (i) a $C_2$-$C_{12}$ aliphatic alcohol that can or cannot contain one or more double bonds and can or cannot contain branched carbons or (ii) a $C_7$-$C_{12}$ aromatic or heteroaromatic alcohols.

As used herein, "C-terminal amide" refers to an amide moiety which replaces the C-terminal hydroxyl moiety usually present at the carboxy-terminus of a polypeptide, such that the polypeptide ends with a carboxamide (i.e., C(=O)—NH2 rather than a C-terminal carboxy (i.e. C(=O)—OH) moiety. These amides are typically formed from the corresponding carboxylic acid and an amine. Generally, amide formation can be accomplished via conventional synthetic techniques. See, for example, Mark, et al. 1980 *Encyclopedia of Chemical Technology*, John Wiley & Sons, New York.

As used herein, "pharmaceutically acceptable carrier" refers to a carrier medium which does not interfere with the effectiveness of the biological activity of the active ingredients and which is not toxic to the host or patient.

As used herein, "stereoisomer" refers to an entity having the same molecular weight, chemical composition, and bonding sequence as another, but having its atoms grouped differently in space about one or more chiral centers. That is, stereoisomers of the same chemical formula will contain identical chemical moieties located in different spatial orientations about at least one chiral center. When pure, stereoisomers have the ability to rotate plane-polarized light. The peptides disclosed herein may have one or more asymmetrical carbon atoms and therefore include various stereoisomers. All stereoisomers are included within the scope of the embodiments.

As used herein, "therapeutically" or "pharmaceutically-effective amount" as applied to the compositions as disclosed herein refers to the amount of composition sufficient to induce a desired biological result. That result can be alleviation of the signs, symptoms, or causes of a disease, or any other desired alteration of a biological system.

As used herein, the terms "peptide residue" and "peptidic structure" are intended to include peptides comprised of naturally-occurring L-amino acids and the corresponding D-amino acids, as well as peptide derivatives, peptide analogues and peptidomimetics of the naturally-occurring L-amino acid, structures. Approaches to designing peptide analogues, derivatives and mimetics are known in the art. For example, see Veber and Freidinger 1985 *TINS* p. 392; Evans, et al. 1987 *J. Med. Chem.* 30:229. Peptidomimetics that are structurally similar to therapeutically useful peptides may be used to produce an equivalent or enhanced therapeutic or prophylactic effect, by methods known in the art and further described in the following references: Spatola, A. F. 1983 in: *Chemistry and Biochemistry of Amino Acids, Peptides, and Proteins*, B. Weinstein, eds., Marcel Dekker, New York, p. 267; Holladay, et al. 1983 *Tetrahedron Lett.* 24:4401-4404.

Systematic substitution of one or more amino acids of a consensus sequence with a D-amino acid of the same type (for example, D-lysine in place of L-lysine) may be used to generate more stable peptides. In addition, constrained peptides comprising a consensus sequence or a substantially identical consensus sequence variation may be generated by methods known in the art (Rizo, et al. 1992 *Ann. Rev. Biochem.* 61:387, incorporated herein by reference in their entireties); for example, by adding internal cysteine residues capable of forming intramolecular disulfide bridges which cyclize the peptide, adding cyclic lactam bridge, or the use of flexible 6-aminohexanoic acid (Ahx), rigid aminoisobutyric acid (Aib) or D-amino acid residues to alter the stability of the helix.

As used herein, a "derivative" of a compound, for example, a peptide or amino acid, refers to a form of that compound in which one or more reactive groups in the compound have been derivatized with a substituent group. Examples of peptide derivatives include peptides in which an amino acid side chain, the peptide backbone, or the amino- or carboxy-terminus has been derivatized (for example, peptidic compounds with methylated amide linkages or hydroxylated amino acids or amino acid residues).

As used herein an "analogue" of a compound refers to a compound which retains chemical structures of the reference compound necessary for functional activity of that compound yet which also contains certain chemical structures which differ from the reference compound. As used herein, a "mimetic" of a compound refers to a compound in which chemical structures of the referenced compound necessary for functional activity of that compound have been replaced with other chemical structures that mimic the conformation of the referenced compound. Examples of peptidomimetics include peptidic compounds in which the peptide backbone is substituted with one or more benzodiazepine molecules, peptides in which all L-amino acids are substituted with the corresponding D-amino acids and "retro-inverso" peptides (see U.S. Pat. No. 4,522,752 by Sisto, James, G. L. et al. 1993 *Science* 260:1937-1942, and Goodman et al. 1981 *Perspectives in Peptide Chemistry* pp. 283-294). Other derivatives include C-terminal hydroxymethyl derivatives, O-modified derivatives (for example, C-terminal hydroxymethyl benzyl ether) and N-terminally modified derivatives including substituted amides such as alkylamides and hydrazides.

As used herein, the term "amino acid structure" is intended to include the amino acid, as well as analogues, derivatives and mimetics of the amino acid that maintain the functional activity of the compound. For example, the term "phenylalanine structure" is intended to include phenylalanine as well as pyridylalanine and homophenylalanine. The term "leucine structure" is intended to include leucine, as well as substitution with valine, isoleucine or other natural or non-natural amino acid having an aliphatic side chain, such as norleucine.

The amino- and/or carboxy-terminus of the peptide compounds disclosed herein can be standard amino and carboxy termini as seen in most proteins. Alternatively, the amino- and/or carboxy-terminus of the peptide compound can be chemically altered by the addition or replacement of a derivative group. Amino-derivative groups which can be present at the N-terminus of a peptide compound include acetyl, aryl, aralkyl, acyl, epoxysuccinyl and cholesteryl groups. Carboxy-derivative groups which can be present at the C-terminus of a peptide compound include alcohol, aldehyde, epoxysuccinate, acid halide, carbonyl, halomethane, diazomethane groups and carboxamide. Carboxamide is preferred.

As used herein, "imaging agent" refers to materials, which when covalently attached to a compound, permit detection of the compound, including but not limited to, detection in vivo in a patient to whom a CLR/RAMP receptor superagonist has been administered. Suitable imaging agents are well known in the art and include, by way of example, radioisotopes, fluorescent labels (for example, fluorescein), and the like. Selection of the label relative to such factors is well within the skill of the art. Covalent attachment of the detectable label to the peptide or peptidomimetic is accomplished by conventional methods well known in the art. For example, when the $^{125}$I radioisotope is employed as the imaging agent, covalent attachment of $^{125}$I to the peptide or the peptidomimetic can be achieved by incorporating the amino acid tyrosine into the peptide or peptidomimetic and then iodinating the peptide (see, for example, Weaner, et al. 1994 Synthesis and Applications of Isotopically Labelled Compounds; pp. 137-140).

As used herein the term "therapeutic agent" means an agent capable of having a desired therapeutic effect for a specific disease indication, including without limitation, a heart failure or blood pressure-reducing agent.

As used herein, "modified" refers to a polypeptide which retains the overall structure of a related polypeptide but which differs by at least one residue from that related polypeptide. As used herein a "modified C-terminus" is a C-terminus of a polypeptide that has a chemical structure other than a standard peptide carboxy group, an example of such a modified C-terminus being a C-terminal carboxamide.

As used herein, "pharmaceutically acceptable carrier" refers to a carrier medium which does not interfere with the effectiveness of the biological activity of the active ingredients and which is not toxic to the host or patient.

As used herein, the terms "peptide residue" and "peptidic structure" are intended to include peptides comprised of naturally-occurring L-amino acids and the corresponding D-amino acids, as well as peptide derivatives, peptide analogues and peptidomimetics of the naturally-occurring L-amino acid structures. Approaches to designing peptide analogues, derivatives and mimetics are known in the art (see Farmer, P. S. in: Drug Design E. J. Ariens, ed. Academic Press, New York, 1980, vol. 10, pp. 119-143; Ball J. B. & Alewood, P. F. 1990 /. Mol. Recognition 3:55; Luthman, et al. 1996 A Textbook of Drug Design and Development, 14:386-406, 2nd Ed., Harwood Academic Publishers; Joachim Grante, Angew. 1994 Chem. Int. Ed. Engl. 33: 1699-1720). Peptidomimetics that are structurally similar to therapeutically useful peptides may be used to produce an equivalent or enhanced therapeutic or prophylactic effect, by methods known in the art (see Spatola, A. F. 1983 in: Chemistry and Biochemistry of Amino Acids, Peptides, and Proteins, B. Weinstein, eds., Marcel Dekker, New York, p. 267; Spatola, A. F. 1983 Vega Data, Vol. 1, Issue 3, Peptide Backbone Modifications (general review); Jennings-White, et al. 1982 Tetrahedron Lett. 23:2533; Holladay, et al. 1983 Tetrahedron Lett. 24:4401-4404; and Hruby, 1982 Life Sci. 31: 189-199).

In addition, constrained peptides comprising a consensus sequence or a substantially identical consensus sequence variation may be generated by methods known in the art (Rizo, et al. 1992 Ann. Rev. Biochem. 61:387); for example, by adding internal cysteine residues or organic linkers capable of forming intramolecular bridges which cyclize the peptide, adding cyclic lactam bridge, or the use of flexible 6-aminohexanoic acid (Ahx), rigid aminoisobutyric acid (Aib) or D-amino acid residues to alter the stability of the helix.

Synthetic or non-naturally occurring amino acids refer to amino acids which do not naturally occur in vivo but which, nevertheless, can be incorporated into the peptide structures described herein.

The modified peptides described herein can be prepared by, for example, by using standard solid phase techniques. (See Merrifield, 1963. Am. Chem. Soc. 85:2149; J. M. Stewart and J. D. Young, 1984 Solid Phase Peptide Syntheses 2nd Ed., Pierce Chemical Company). These procedures can also be used to synthesize peptides in which amino acids other than the 20 naturally occurring, genetically encoded amino acids are substituted at one, two, or more positions of any of the modified peptides as disclosed herein. For instance, naphthylalanine can be substituted for tryptophan, facilitating synthesis. Other synthetic amino acids that can be substituted into the peptides of the present embodiments include L-hydroxypropyl, L-3, 4-dihydroxy-phenylalanyl, d amino acids such as L-d-hydroxylysyl and D-d-methylalanyl, L-a-methylalanyl, β-amino acids, and isoquinolyl. D amino acids and non-naturally occurring synthetic amino acids can also be incorporated into the peptides of the present embodiments (see Roberts, et al. 1983 Unusual Amino/Acids in Peptide Synthesis 5:341-449). In some embodiments, the naturally occurring side chains of the 20 genetically encoded amino acids, or any other side chain as disclosed herein can be transposed to the nitrogen of the amino acid, instead of the α-carbon as typically found in peptides.

Some embodiments provide modified peptide agonists that have 60%-99% amino acid sequence identity with a full-length polypeptide sequence as disclosed herein (e.g., SEQ ID NOS: 28-51, 69-70, 92, 94, 101, 103, and 110) or any other specifically defined fragment of a full-length polypeptide sequence as disclosed herein.

"Percent (%) amino acid sequence identity" with respect to the polypeptide sequences identified herein is defined as the percentage of amino acid residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

Variations in the sequence of the agonist or antagonist peptides described herein, can be made, for example, using any of the techniques and guidelines for conservative and non-conservative mutations set forth, for instance, in U.S. Pat. No. 5,364,934 (Drayna et al., issued Nov. 15, 1994). Variations may be a substitution, deletion or insertion of the agonist or antagonist peptides that results in a change in the amino acid sequence of the agonist or antagonist peptides as compared with the reference agonist or antagonist peptide sequences.

Stabilized superagonistic and superantagonistic peptide derivatives are provided where the sequence and/or side chains of the peptide derivatives are altered. The bioactivity of the derivatives toward CLR/RAMP receptors is superior when compared to wt ADM, CGRP, or IMD. The stabilized superagonistic peptides also show superior pharmacological action as compared to wt peptides on the basis of their specific action on endothelial cell proliferation and/or viability in vitro.

Optionally, these modified peptide derivatives are covalently linked to a heterologous moiety, which may comprise a polymer, an Fc, an FcRn binding ligand, immunoglobulin, albumin, a collagen-binding motif, a RGD motif, and an albumin-binding ligand, or by N-methylation. A covalently linked polymer may be selected from the group consisting of optionally substituted, saturated, or mono- or di-unsaturated, linear or branched C3-C100 carboxylic acids, preferably C4-C30 carboxylic acids (lipidation), a polyethyleneglycol (PEG) moiety, a polypropylenglycol (PPG) moiety, a PAS moiety, which is an amino acid sequence comprising mainly alanine and serine residues or comprising mainly alanine, serine, and proline residues, the amino acid sequence forming random coil conformation under physiological conditions [US No. 2010/0292130 and WO 2008/155134], and a hydroxyethylstarch (HES) moiety [WO 02/080979], a Fc, a FcRn binding ligand, albumin and an albumin-binding ligand as well as an XTEN moiety (see Schellenberger, et al., 2009, Nature Biotechnology 27(12): 1186-1192).

Where the covalent linkage is to PEG, the PEG molecular weight may be between about 1 kDa and about 100 kDa for ease in handling and manufacturing. For example, the PEG may have an average molecular weight of about 200, 500, 1000, 2000, 4000, 8000, 16,000, 32,000, 64,000, or 100,000 kDa. In some embodiments, the PEG may have a branched structure (U.S. Pat. No. 5,643,575; Morpurgo et al. Appl. Biochem. Biotechnol. 56:59-72 (1996); Vorobjev et al, Nucleosides Nucleotides 18:2745-2750 (1999); and Caliceti et al, Bioconjug. Chem. 10:638-646 (1999)).

Optionally, modified peptide derivatives comprise one or more substitutions of disulfide bonds with lactam bridges to increase the metabolic stability of the peptides. Cystathiones are resistant towards thiol reduction. Therefore, substitutions of disulfides with thioethers, or selenosulfide, diselenide and ditelluride bridges can provide protection against reduction [Knerr et al., ACS Chem Biol, 6(7), 753-760, 2011; Muttenthaler et al. J Med Chem., 53(24), 8585-8596, 2010]. Peptide disulfide bond mimics based on diaminodiacids can also be used to improve the stability of analogs (Cui et al., Angew Chem, 125, 9737-9741, 2013). The disulfide bridge can also be modified either by the insertion of linkers or bridges of a different nature.

Polymer matrices that contain a drug molecule in a noncovalently bound state can be injectable as solution, hydro gels, micro particles or micelles [D. H. Lee et al, J. Contr. Rel., 92, 291-299, 2003]. Permanent PEGylation of peptides or proteins to enhance their solubility, reduce immunogenicity and increase half live by reducing renal clearance is known in the art [Caliceti P., Veronese F. M., Adv. Drug Deliv. Rev., 55, 1261-1277, 2003; T. Peleg-Shulman et al., J. Med. Chem., 47, 4897-4904, 2004].

Optionally, modified peptide derivatives are modified by the addition of one or more alkane, cholesterol, or PEG-cholesterol moieties to increase the metabolic stability of the peptides. Stapled peptides, via the introduction of a synthetic brace (staple), can be synthesized using ring-closing metathesis to lock a peptide in a specific conformation and reduce conformational entropy.

The present invention also includes prodrugs of the compounds of formula (I), (II), and (III), i.e. compounds which themselves can be biologically active or inactive, but are converted (for example metabolically or hydrolytically) into compounds of formula (I), (II), and (III) in the body. Prodrugs may be based on masking amine functionalities, or masking the phenolic group of a tyrosine (the internal nucleophile assisted cleavage of a carbamate on the phenolic group); and the like.

Polymer based prodrugs are provided that comprise superagonistic or superantagonistic peptides described herein. A prodrug is any compound that undergoes biotransformation before exhibiting its pharmacological effects. Carrier-linked prodrug (Carrier prodrug) comprises a temporary linkage of a given active substance with a transient carrier group that produces improved physicochemical or pharmacokinetic properties and that can be removed in vivo, by a biochemical cleavage. PEG-based carrier prodrugs need enzymatic activation of the linker between the active drug and the carrier, mostly initiated by enzymatic hydrolysis. Commonly used cascading linkers attach an amine functionality in the peptide or protein. In cascading linkers a masking group is removed as the rate limiting step in the cascade. This activates the linker to decompose in a second position to release the peptide or protein. Commonly the masking group can be removed by an enzymatic mechanism [R. B. Greenwald et al. in WO 2002/089789, Greenwald, et al., J. Med. Chem. 1999, 42, 3657-3667, F. M. H. DeGroot et al. in WO 2002/083180 and WO 2004/043493, and D. Shabat et al. in WO 2004/019993]. An alternative not relying on enzymatic activation (see WO 2005/099768) utilizes a masking group on a phenol, which removed in a purely pH dependent manner by the attack of an internal nucleophile. This activates the linker for further decomposition (see U.S. Pat. No. 8,680,315). Upon pH triggered decomposition the drug is released. Another approach optimized for phenols, e.g. tyrosine, is based on a carbamate that is pH dependently attacked by a nucleophilic amine under release of the phenol and generation of a cyclic urea attached to the macromolecule as described in WO 2013/064455.

The pharmacokinetic properties of peptides can be adjusted by lipidation. Lipidation can occur to the N-terminus or to the side chain functionalities of amino acids within the peptide sequence. Lipidation is described in publications and patents (Zhang et al. Curr Med 19:1602-18, 2012; Gerauer et al. Wiley Encyclopedia of Chemical Biology, Volume 2, 520-530, 2009, (Hrsg. Begley, T. P.). John Wiley & Sons, Hoboken, N.J. Lipidation of an ADM sequence is described in WO 2012/138867. Labeled ADM derivatives for use as imaging and also therapeutic agent are known [J. Depuis et al. in CA 2567478 and WO 2008/138141]. In these ADM derivatives a complexating cage like molecular structure capable of binding radioactive isotopes was attached to the N terminus of ADM in a direct manner or via a spacer unit potentially also including short PEG spacers. The diagnostic or therapeutic value of theses drugs arises from the targeted delivery of the radioactive molecule.

The present invention also encompasses all suitable isotopic variants of the compounds of formula (I), (II), and (III) according to the invention. An isotopic variant of a compound is understood to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound may be beneficial, for example, for the examination of the mechanism of action or of the active compound distribution in the body. In addition, the incorporation of isotopes, for example of deuterium, can lead to particular therapeutic benefits as a consequence of greater metabolic stability of the compound, for example an extension of the half-life in the body or a reduction in the active dose required.

Peptide Compositions and Formulations

Provided herein are compounds of the formula (I), (II), and (II) and the salts thereof, solvates thereof and solvates of the salts thereof. The compounds may be specifically set forth as working examples.

The peptides described herein are optionally provided as a minaturized molecular mass that facilitates the permeation and diffusion of molecules in vivo, and the access to the central nervous system, thereby improving the utility in the treatment of diseases. The generation of miniaturized receptor agonists or antagonists not only facilitates the diffusion of the peptides within extracellular fluid, but also allows the molecules to enter limited space that is too small to allow the entrance of a larger analog. Prior ADM or IMD analogs were 39 and 40 amino-acid long, respectively; and CGRP analogs were 37 amino acids in length. The peptides provided herein comprise examples of miniaturized superagonists of 35-36 amino-acid in length, and miniaturized super-antagonists of 17-28 amino-acid in length. The miniaturized analogs are also unique in that no CLR/RAMP receptor ligands that contain a truncation in the middle of the continuous sequences of the wild type peptides have been previously described.

Agonists and Superagonists

In some embodiments, a CLR/RAMP receptor superagonist is provided, having the structure of Formula I:

$$B^a\text{—}C^a\text{-}D^a \qquad (I)$$

wherein $B^a$ is a modified N-terminal fragment of adrenomedullin peptide family member comprising from twenty to twenty eight amino acid residues, wherein two amino acid residues of the N-terminal fragment are cysteine (Cys), and wherein the C-terminal residue of the fragment is threonine (Thr). $B^a$ may be represented by the structure: ($B^0$—$B^1$—$B^2$—C—$B^4$—$B^5$-G-$B^7$—C—$B^9$—$B^{10}$—$B^{11}$—$B^{12}$—$B^{13}$—$B^{14}$—$B^{15}$—$B^{16}$—$B^{17}$—$B^{18}$—$B^{19}$—$B^{20}$—$B^{21}$);

$C^a$ is a central core consist of 3-12 amino acids; and $D^a$ is a modified C-terminal fragment of intermedin (IMD) comprising 3-6 amino acid residues with a C-terminal amide, where at least one amino acid of $D^a$ is selected from histidine (His), proline (P), serine (Ser), and tyrosine (Tyr).

In some embodiments, $B^a$ is characterized by two cysteines present in the sequence that form a disulfide bond. Residues between the two cys residues involved in the disulfide bond are unconstrained in sequence. The aforementioned disulfide bond stabilizes the structure of $B^a$—$C^a$-$D^a$, facilitating both formation of an alpha-helix, and binding of $B^a$—$C^a$-$D^a$ to the transmembrane component of a target receptor.

Introduction of a mini-PEG together with an acylation modification at the N-terminus, or an acylation modification in the absence of mini-PEG at the N-terminus of a peptide of Formula I results in a superagonist activity of the molecule in interactions with a CLR/RAMP1 or a CLR/RAMP2 receptor when compared to the wild-type ADM (SEQ ID NOS: 53-54), IMD (SEQ ID NO: 52), or a chimeric peptide with inappropriate sequences (SEQ ID NOS: 55-68). Such modifications yield a molecule that occupies the receptor and activates the signal transduction pathway at a greater than about 5-fold increase in receptor-activation potency when compared with the wild-type ADM, IMD, or chimeric ligands in the absence of such acylation and/or pegylation. In some embodiments, a superagonist comprises acylation modification in the absence of mini-PEG.

Addition of residues N-terminal to the first cysteine of $B^a$—$C^a$-$D^a$ may not affect the superagonistic characteristics of the polypeptide. In some embodiments the peptide is joined to an amino acid residue or polypeptide at the residues N-terminal to the first cysteine of the peptide of Formula I. The peptide of formula I may be joined to a polypeptide, e.g. a serum polypeptide such as albumin, an immunoglobulin, including an immunoglobulin constant region, and the like.

In some embodiments, a CLR/RAMP receptor superagonist of Formula I comprises, consists or consists essentially of an amino acid sequence selected from the group consisting of (where "pal" signifies a palmitate moiety, and "ace" signifies acetylated terminus):

(SEQ ID NO: 28)
mini-PEG-K(PAL)GCRFGTCTVQKLAHQIYQFTDKDKDNSAPVDPSSP
HSY-NH₂

(SEQ ID NO: 29)
mini-PEG-K(PAL)GCRFGTCTVQKLAHQIYQFTPAGRQDSAPVDPSSP
HSY-NH₂

(SEQ ID NO: 30)
Pal-KGCRFGTCTVQKLAHQIYQFTDKDKDNSAPVDPSSPHSY-NH₂

(SEQ ID NO: 31)
Pal-KGCRFGTCTVQKLAHQIYQFTPAGRQDSAPVDPSSPHSY-NH₂

(SEQ ID NO: 32)
Ace-K(PAL)GCRFGTCTVQKLAHQIYQFTDKDKDNSAPVDPSSPHSY-
NH₂

(SEQ ID NO: 33)
Ace-K(PAL)GCRFGTCTVQKLAHQIYQFTPAGRQDSAPVDPSSPHSY-
NH₂

(SEQ ID NO: 34)
Pal-KGCRFGTCTVQKLAHQIYQFTDKDKDNVAPVDPSSPHSY-NH₂, (SEQ ID NO: 35)
Pal-KGCRFGTCTVQKLAHQIYQFTDKDKQDSAPVDPSSPHSY-NH₂, (SEQ ID NO: 36)
Pal-KGCRFGTCTVQKLAHQIYQFTDKGRQDSAPVDPSSPHSY-NH₂, (SEQ ID NO: 37)
Pal-K(Pal)GCRFGTCTVQKLAHQIYQFTDKDKDNSAPVDPSSPHSY-
NH₂, (SEQ ID NO: 38)
Pal-KIKKTLRTGCRFGTCTVQKLAHQIYQFTDKDKDNSAPVDPSSPHS
Y-NH₂, (SEQ ID NO: 39)
Ace-TK(Pal)KTLRTGCRFGTCTVQKLAHQIYQFTDKDKDNSAPVDPSS
PHSY-NH₂;

(SEQ ID NO: 40)
Pal-KIKKTLRTGCRFGTCTVQKLAHQIYQFTDKDKDNVAPVDPSSPHS
Y-NH₂, (SEQ ID NO: 41)
Ace-TK(Pal)KTLRTGCRFGTCTVQKLAHQIYQFTDKDKDNVAPVDPSS
PHSY-NH₂.

(SEQ ID NO: 42)
miniPEG-TK(Pal)KTLRTGCRFGTCTVQKLAHQIYQFTDKDKDNVAPV
DPSSPHSY-NH₂.

(SEQ ID NO: 43)
miniPEG-K(PAL)CRFGTCTVQKLAHQIYQFTDKDKDNSAPVDPSSPHS
Y-NH₂.

(SEQ ID NO: 44)
Pal-KCRFGTCTVQKLAHQIYQFTDKDKDNSAPVDPSSPHSY-NH₂.

(SEQ ID NO: 45)
Pal-GCRFGTCTVQKLAHQIYQFTDKDKDNSAPVDPSSPHSY-NH₂.

```
                                            (SEQ ID NO: 46)
miniPEG-K(PAL)GCRFGTCTVQKLAHQIYQFTDKDKDSAPVDPSSPHS
Y-NH2.

(SEQ ID NO: 47)
miniPEG-K(PAL)GCRFGTCTVQKLAHQIYQFTDKDKSAPVDPSSPHS
Y-NH2.

(SEQ ID NO: 48)
miniPEG-K(PAL)GCRFGTCTVQKLAHQIYQFTDKDSAPVDPSSPHSY-
NH2.

(SEQ ID NO: 49)
miniPEG-K(PAL)GCRFGTCTVQKLAHQIYQFTPAGRQDSAPVDPSSPH
SY-NH2.

(SEQ ID NO: 50)
miniPEG-K(PAL)GCRFGTCTVQKLAHQIYQFTDKDKDNVAPVDPSSPH
SY-NH2.

(SEQ ID NO: 51)
miniPEG-K(PAL)GCRFGTCTVQKLAHQIYQFTDKDKQDSAPVDPSSPH
SY-NH2

(SEQ ID NO: 69)
mini-PEG-K(PAL)GCRFGTCTVQKLAHQIYQFTDKDKDNVAPRSKISP
QGY-NH2

(SEQ ID NO: 70)
miniPEG-K(PAL)TKKTLRTGCRFGTCTVQKLAHQIYQFTDKDKDNVAP
RSKISPQGY-NH2

(SEQ ID NO: 92)
Pal-KGCRFGTCTVQKLAHQIYQFTDKDSAPVDPSSPHSY-NH2.

(SEQ ID NO: 94)
miniPEG-K(PAL)GCRFGTCTVQKLAHQIYQFTDKDKDNVDPSSPHSY-
NH2

(SEQ ID NO: 101)
miniPEG-K(PAL)GCRFGTCTVQKLAHQIYQFTDKDVAPRSKISPQGY-
NH2

(SEQ ID NO: 103)
Pal-KGCRFGTCTVQKLAHQIYQFTDKDVAPRSKISPQGY-NH2

(SEQ ID NO: 110)
Pal-KGCRFGTCTVQKLAHQIYQFTDKDAPVDPSSPHSY-NH2
```

The peptides may comprise fragments derived from ADM and/or IMD, as evident by an alignment of the sequences.

In some embodiments, one or more amino acid residues are fused N-terminally to $B^1$, thereby generating a polypeptide with an N-terminal extension of residues with respect to $B^1$. In some embodiments the extension does not affect the bioactivity of the superagonist.

In some embodiments the superagonist of Formula I, as disclosed herein, comprises a central core $C^\alpha$ comprising 3 to 12 amino acid residues. The length of the central core is constrained not by the number of residues but by the steric considerations that require $B^\alpha$ and $D^\alpha$ to be positioned so that they may interact with a target receptor at the cell membrane surface. In some embodiments of the CLR/RAMP receptor superagonist having the structure of Formula I, the central core comprises a fragment of adrenomedullin or intermedin from any of a range of species, including without limitation mammalian species. In some embodiments, $C^\alpha$ has sequence identity of at least 60%, of at least 85%, of at least 90%, of at least 95%, of at least 99%, or 100% with the sequence DKDKDNVAPRSK (SEQ ID NO:18), DKDKDNSAPVDP (SEQ ID NO:19), PAGRQDSAPVDP (SEQ ID NO:20), DKDKDNVAPVDP (SEQ ID NO:21), DKDKQDSAPVDP (SEQ ID NO:22), DKGRQDSAPVDP (SEQ ID NO:23), DKDKDSAPVDP (SEQ ID NO:24), DKDKSAPVDP (SEQ ID NO:25), or DKDSAPVDP (SEQ ID NO:26). In some embodiments, $C^\alpha$ has an 60% or greater sequence identity with any of SEQ ID NO:18-26.

$D^\alpha$ is a C-terminal fragment of IMD peptide comprising 3, 4, 5, 6, or more amino acid residues from the C-terminus of intermedin. $D^\alpha$ has a C-terminal amide. At least one amino acid of $D^\alpha$ is selected from proline (Pro), histidine (His), tyrosine (Tyr), and serine (Ser). Like $C^\alpha$ above, $D^\alpha$ is constrained not by its sequence but by its ability to interact with both CLR/RAMP1 and CLR/RAMP2 receptors. In the case of $D^\alpha$ that requirement is that it interacts with a target receptor at a site in its extracellular domain such that when the agonist binds the receptors become activated.

In some embodiments $D^\alpha$ comprises at least one tyrosine residue. In some embodiments the C-terminus of $D^\alpha$ is modified so that it comprises an amidated carboxy (—C(=O)NH$_2$) moiety.

In some embodiments a CLR/RAMP2 receptor-specific superagonist comprises, consists or consists essentially of the peptide of SEQ ID NO:69, 70, 94, 202, 103 or 110.

In some embodiments herein a CLR/RAMP receptor superagonist is provided herein that retains the sequence of an agonist that binds the CLR/RAMP receptors at the cellular membrane, but that differs at least one amino acid residue from the agonist sequence. In a preferred embodiment, the chimeric superagonists derived from ADM and IMD are part of the structure used to increase efficacy of the superagonist or superantagonist.

In some embodiments $B^\alpha$ is selected from the group consisting of the peptide of SEQ ID NO:1-16. In some embodiments a CLR/RAMP receptor superagonist of Formula I comprises a first peptide fragment having from about nineteen amino acid residues or more from an ADM sequence, including without limitation human ADM, a second peptide fragment having from about three amino acid residues or more from ADM and IMD, including without limitation human ADM and IMD, and a third peptide fragment from IMD, including without limitation human IMD. In some embodiments a CLR/RAMP receptor superagonist of Formula I, comprises a contiguous second and third peptide fragment.

Antagonists and Superantagonists

Certain select amino acids in the N-terminal portion of the ADM/CGRP/IMD family peptides are responsible for the peptide agonist activity. Truncation or substituting of certain amino acids in the N-terminal portion of these peptides can tune the activity from an agonist to an antagonist. It has been discovered that additional substitutions or modifications can provide additional desirable characteristics to the antagonists. For example, the blockage of CGRP signaling may be useful for preventing the development or progression of migraine headache; whereas the blockage of CLR/RAMP2 signaling represents an anti-angiogenesis approach to reduce tumor growth and cancer progression. However, existing CLR/RAMP receptor antagonists are associated with efficacy concerns. Peptide antagonists such as CGRP8-37 and ADM22-52 have extremely short half-lives and low potencies, and are receptor-specific.

In some embodiments, a CLR/RAMP receptor superantagonist is provided, said antagonist having the structure of Formula II:

$$B^b\text{—}C^b\text{-}D^b \quad (II)$$

wherein $B^b$ is an N-terminal fragment of adrenomedullin peptide family member comprising from twelve to thirteen amino acid residues, wherein $B^b$ may be represented by the structure: ($B^0$—$B^1$—$B^2$—$B^3$—$B^4$—$B^5$—$B^6$—$B^7$—$B^8$—$B^9$—$B^{10}$—$B^{11}$—$B^{12}$);
$C^b$ is a central core consisting of from about 3, about 4, about 5, about 6, about 7, about 8, about 9, about 10, about 11, about 12 amino acids; and
$D^b$ is a modified C-terminal fragment of intermedin (IMD) comprising of from about 3, about 4, about 5, about 6 amino acid residues with a C-terminal amide, where at least one amino acid of the C-terminal fragment is selected from histidine (His), proline (P), serine (Ser), tyrosine (Tyr).

In some embodiments a pan-specific, CLR/RAMP1-specific, and CLR/RAMP2-specific receptor superantagonist comprises, consists or consists essentially of:

```
                                           (SEQ ID NO: 77)
Pal- TVQKLAHQIYQFTDKDKDNSAPVDPSSPHSY-NH2

(SEQ ID NO: 78)
miniPEG-K(Pal)VQKLAHQIYQFTDKDKDNSAPVDPSSPHSY-NH2

(SEQ ID NO: 112)
miniPEG-K(Pal)VQKLAHQIYQFTDKDSAPVDPSSPHSY-NH2

(SEQ ID NO: 114)
miniPEG-K(Pal)VQKLAHQIYSAPVDPSSPHSY-NH2

(SEQ ID NO: 119)
Pal-KVQKLAHQIYQFTDKDVAPRSKISPQGY-NH2

(SEQ ID NO: 120)
Pal-KVQNLSHRLWQLMGPAGSAPVDPSSPHSY-NH2

(SEQ ID NO: 121)
Pal-KVQKLAHQIYQFTDKDSAPVDPSSPHSY-NH2

(SEQ ID NO: 122)
Pal-KVQKLAHQIYSAPVDPSSPHSY-NH2

(SEQ ID NO: 123)
Pal-KVQKLAHQISAPVDPSSPHSY-NH2

(SEQ ID NO: 124)
Pal-KVQKLAHQSAPVDPSSPHSY-NH2

(SEQ ID NO: 125)
Pal-KVQKLAHQIYQFTDKSAPVDPSSPHSY-NH2

(SEQ ID NO: 139)
Pal-KVQKLSAPVDPSSPHSY-NH2.
```

In some embodiments a CLR/RAMP receptor superantagonist comprises an amino acid sequence having greater than 60%, greater than 70%, greater than 870%, greater than 90%, greater than 95% sequence identity to the amino acid sequence of SEQ ID NO: 77-78, 112, 114, 119, 120-125, or 139 wherein said peptide retains antagonist activity. A CLR/RAMP receptor superantagonist may comprise a stereoisomer, derivative, or peptidomimetics to the amino acid sequence of SEQ ID NO: 77-78, 112, 114, 119, 120-125, or 139.

In some embodiments of the CLR/RAMP receptor superantagonists having the structure of Formula II, the antagonist comprises a third peptide fragment ($D^b$) having 6 amino acid residues or less, wherein said third peptide fragment has a sequence from ADM or IMD. In some embodiments of the CLR/RAMP receptor superantagonists having the structure of Formula II, the second peptide fragment and the third peptide fragment are contiguous.

In some embodiments of the modified superantagonist having the structure of Formula II or III, the sequence comprises a fragment of an ADM or IMD from any of a range of species. In some embodiments, the analogs can have a 60%, 65%, 70%, 75%, 80%, 85%, 90%, or 95% sequence identity with the SEQ ID NOS: 77-78, 112, 114, 119, 120-125, or 139.

In some embodiments of a CLR/RAMP receptor superantagonist having the structure of Formula II: $B^b$ is a modified N-terminal fragment of ADM and IMD peptide family member comprising from four to thirteen amino acid residues; $C^b$ is a central core comprising from three to six amino acid residues; and $D^b$ is a C-terminal fragment of IMD comprising from three to six amino acid residues with a C-terminal amide, where at least one amino acid of the C-terminal fragment is histidine (His), proline (P), serine (Ser), or tyrosine (Tyr), or pharmaceutically acceptable salt thereof. The length of the $B^b$, $C^b$, and $D^b$ is constrained not by the number of residues per se but by the steric considerations that allow the analogs to interact with a target receptor at the cell membrane surface and at an extracellular domain (i.e., a functional requirement), respectively, in competition with wild type ADM/CGRP/IMD family peptides.

In some embodiments, said CLR/RAMP receptor superantagonists have a loss of the activation activity of the molecule in interactions with a CLR/RAMP receptor or with a member of the calcitonin/CGRP family of receptors as compared to the wild-type molecule, but may not affect the binding to the receptor. As a result, said CLR/RAMP receptor superantagonists represent a molecule which can occupy the receptor, but which antagonize rather than activates the signal transduction pathway by making the receptor unavailable for binding by signal-transducing agonists or by repelling the hydrophilicity of ligands.

In some embodiments, superantagonists have the structure of Formula II, wherein the $B^b$ fragment comprises: ($B^0$—$B^1$—$B^2$—$B^3$—$B^4$—$B^5$—$B^6$—$B^7$—$B^8$—$B^9$—$B^{10}$—$B^{11}$—$B^{12}$ (SEQ ID NO: 16), where: $B^0$ can be selected from the group consisting of a natural amino acid or absent; $B^1$, $B^2$, $B^3$, $B^4$, $B^5$, $B^6$, $B^7$, $B^8$, $B^9$, $B^{10}$, $B^{11}$, and $B^{12}$ can be selected from the group consisting of valine (Val), leucine (Leu), alanine (Ala), isoleucine (Ile), cysteine (Cys), serine (Ser), and tyrosine (Tyr), arginine (Arg), asparagine (Asn), aspartic acid (Asp), glutamic acid (Glu), glutamine (Gln), histidine (His), lysine (Lys), and tyrosine (Tyr), phenylalanine (F), or absent.

In some embodiments a superantagonist has a structure of Formula III:

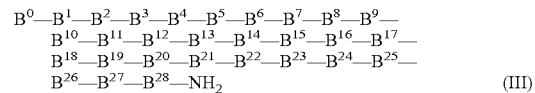

$$B^0\text{—}B^1\text{—}B^2\text{—}B^3\text{—}B^4\text{—}B^5\text{—}B^6\text{—}B^7\text{—}B^8\text{—}B^9\text{—}$$
$$B^{10}\text{—}B^{11}\text{—}B^{12}\text{—}B^{13}\text{—}B^{14}\text{—}B^{15}\text{—}B^{16}\text{—}B^{17}\text{—}$$
$$B^{18}\text{—}B^{19}\text{—}B^{20}\text{—}B^{21}\text{—}B^{22}\text{—}B^{23}\text{—}B^{24}\text{—}B^{25}\text{—}$$
$$B^{26}\text{—}B^{27}\text{—}B^{28}\text{—}NH_2 \quad (III)$$

where: $B^0$ is selected from the group consisting of an empty residue, acylated histidine (acy-His), acylated arginine (acy-Arg), acylated lysine (acy-Lys), acylated serine (acy-Ser), acylated threonine (acy-Thr), acylated tyrosine (acy-Tyr), acylated aspartic acid (acy-Asp), acylated glutamic acid (acy-Glu), acylated glutamine (acy-Gln), acylated asparagine (acy-Asn); acylated valine (acy-Val), acylated alanine (acy-Ala), acylated glycine (acy-Gly), acylated isoleucine (acy-Ile), acylated leucine (acy-Leu), acylated phenylalanine (acy-Phe), acylated tryptophan (acy-Trp), acylated proline (acy-Pro), acylated methionine (acy-Met), acylated cysteine (acy-Cys), double acylated histidine (acy-His(acy)), ace-histidine(acy) (ace-His(acy)), mini-PEG-acylated-histidine (mini-PEG-His(acy)), double acylated arginine (acy-Arg(acy)), ace-arginine (acy) (ace-Arg(acy)), mini-PEG-acylated-arginine (mini-PEG-Arg(acy)), lysine (Lys), double acylated lysine (acy-Lys(acy)), ace-lysine(acy) (ace-Lys(acy)), and mini-PEG-acylated-lysine (mini-PEG-Lys(acy);

$B^1$ is selected from the group consisting of an empty residue, Val, Ala, Gly, Ile, and Leu $B^2$ is selected from the group consisting of an empty residue, Gln, Glu, Asp, and Asn;

$B^3$ is selected from the group consisting of an empty residue, His, Arg, Lys, Gln, and Asp;

$B^4$ is selected from the group consisting of an empty residue, Val, Ala, Gly, Ile, and Leu;

$B^5$ is selected from the group consisting of an empty residue, Val, Ala, Gly, Ile, Leu, Ser, Th, and Tyr;

$B^6$ is selected from the group consisting of an empty residue, His, Arg, and Lys;

$B^7$ is selected from the group consisting of an empty residue, Gln, and Asn, His, Arg, and Lys;

$B^8$ is selected from the group consisting of an empty residue, Val, Ala, Gly, Ile, and Leu;

$B^9$ is selected from the group consisting of an empty residue, Trp, Phe, Ser, Thr, and Tyr;

$B^{10}$ is selected from the group consisting of an empty residue, Gln, Glu, Asp, and Asn;

$B^{11}$ is selected from the group consisting of an empty residue, Trp, Phe, Val, Ala, Gly, Ile, and Leu;

$B^{12}$ is selected from the group consisting of an empty residue, Ser, Thr, and Tyr; Met, Trp, and Phe;

$B^{13}$ is selected from the group consisting of an empty residue, Gln, Glu, Asp, and Asn, Val, Ala, Gly, Ile, and Leu;

$B^{14}$ is selected from the group consisting of an empty residue, His, Arg, Lys, Val, Ala, Gly, Ile, Leu, and Pro;

$B^{15}$ is selected from the group consisting of an empty residue, Gln, Glu, Asp, Asn, Val, Ala, Gly, Ile, and Leu;

$B^{16}$ is selected from the group consisting of an empty residue, Val, Ala, Gly, Ile, and Leu;

$B^{17}$ is selected from the group consisting of an empty residue, Ser, Thr, and Tyr;

$B^{18}$ is selected from the group consisting of an empty residue, Val, Ala, Gly, Ile, and Leu;

$B^{19}$ is selected from the group consisting of an empty residue, Val, Ala, Gly, Ile, Leu, and Pro;

$B^{20}$ is selected from the group consisting of an empty residue, His, Arg, Lys, Val, Ala, Gly, Ile, and Leu;

$B^{21}$ is selected from the group consisting of an empty residue, Ser, Thr, Tyr, Gln, Glu, Asp, and Asn;

$B^{22}$ is selected from the group consisting of an empty residue, His, Arg, Lys, Val, Ala, Gly, Ile, Leu, and Pro;

$B^{23}$ is selected from the group consisting of an empty residue, Ser, Thr, Tyr, Val, Ala, Gly, Ile, and Leu;

$B^{24}$ is selected from the group consisting of an empty residue, Ser, Thr, and Tyr;

$B^{25}$ is selected from the group consisting of an empty residue, Val, Ala, Gly, Ile, Leu, and Pro;

$B^{26}$ is selected from the group consisting of an empty residue, His, Arg, Lys, Gln, Glu, Asp, and Asn;

$B^{27}$ is selected from the group consisting of an empty residue, Val, Ala, Gly, Ile, Leu, Ser, Thr, and Tyr;

$B^{28}$ is selected from the group consisting of an empty residue, Ser, Thr, and Tyr.

A superantagonist may be provided as a pharmaceutical composition comprising one of superantagonist peptides. The pharmaceutical composition can be used in a method for treating headache, migraine, arthritis pain, tumor-associated pain, neuropathic pain, endometriosis, morphine tolerance, macular degeneration, tumor angiogenesis, tumor metastasis, or angioedema in an individual, the method comprising administering to an individual an effective amount of a CLR/RAMP receptor superantagonist. Some embodiments provide a pharmaceutical composition comprising a pharmaceutically acceptable excipient and the superantagonist as disclosed and described herein.

Some embodiments provide a method of treating a headache or a tumor in an individual, the method comprising administering to the individual an effective amount of the superantagonist as disclosed and described herein. In some embodiments, the method can further comprise identifying a subject suffering from headache or tumor. In some embodiments, the headache is a migraine.

Some embodiments provide a method of treating a condition associated with aberrant levels of CGRP comprising the administration of the superantagonist as disclosed and described herein, to an individual, the method comprising administering to the individual an effective amount of a superantagonist as disclosed and described herein. In some embodiments, the condition is a migraine.

General Peptide Modification

In some embodiments, one or more residues are fused N-terminally to $B^b$ of the agonist in formula I and antagonist in formula II and III, thereby generating a polypeptide with an N-terminal extension of residues with respect to the analogs. In some embodiments this extension affects the stability of the agonist or the antagonist after administration.

In some embodiments, addition of residues N-terminal or C-terminal to $B^b$ of the agonist or antagonist, for example, an XTENS sequence comprising Ala, Glu, Gly, Pro, Ser and Thr, may extend the stability of the analog (Schellenberger et al., 2009, Nature Biotechnology 27 (12): 1186-1192). In some embodiments the addition of residues N-terminal or C-terminal may increase the half-life of an administered drug. These changes are contemplated herein; a person having ordinary skill in the art will know how this can be done.

Some embodiments provide a method of identifying a CLR/RAMP receptor binding ligand by providing the superantagonist bound to a CLR/RAMP receptor, providing a test compound or library of test compounds, and identifying compounds which are capable of dissociating the superantagonist from the CLR/RAMP receptor. Such compounds identified by this method may be further screened against other CLR/RAMP receptor binding agents to identify selective CLR/RAMP receptor binding ligands.

In some embodiments of the invention a CLR/RAMP receptor superagonist or superantagonist peptide is provided in which the peptide comprises, consists or consists essentially of an amino acid sequence having at least 60%, at least 70%, at least 80%, at least 90%, at least 95% or more sequence identity to the amino acid sequence of SEQ ID NOS: 28-51, 69-70, 77-78, 92, 94, 101, 103, 110, 112, 114, 119, 120-125, and 139, wherein said peptide retains agonist or antagonist activity.

Also provided are therapeutic agents, e.g. drugs, therapeutic polypeptides, etc. that are linked to a CLR/RAMP receptor superagonist or superantagonist of the invention, where the CLR/RAMP receptor superagonist or superantagonist acts as a targeting moiety for the therapeutic agent. Also provided are methods of delivering the therapeutic agent linked to a CLR/RAMP receptor superagonist or superantagonist of the invention, the method comprising administering an effective dose of the linked therapeutic agent to an individual in need thereof. In some embodiments, the therapeutic agent is an imaging agent. Labeled CLR/RAMP receptor liganid (e.g., adrenomedullin derivatives for use as imaging and also therapeutic agent is described by J. Depuis et al. in CA 2567478 and WO 2008/138141). In these ADM derivatives a complexating cage like molecular structure capable of binding radioactive isotopes was attached to the N terminus of ADM in a direct manner or via a spacer unit potentially also including short PEG spacers. The diagnostic or therapeutic value of theses drugs arises from the targeted delivery of the radioactive molecule.

Some embodiments provide a method of identifying a CLR/RAMP receptor by providing a CLR/RAMP receptor superagonist or superantagonist bound to a CLR/RAMP receptor, providing a test compound or library of test compounds, and for imaging CLR/RAMP receptors in vivo.

In some embodiments, a heterologous moiety is linked to the superagonist or superantagonist. In some embodiments the heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. The skilled person is aware that an amino acid polymer also may form random coil conformation when residues other than alanine, serine, and proline are added as a minor constituent in the PAS sequence. The amino acids different from alanine, serine and proline may be selected from the group consisting of Arg, Asn, Asp, Cys, Gin, Glu, Gly, His, He, Leu, Lys, Met, Phe, Thr, Trp, Tyr, and Val. Under physiological conditions, the PAS sequence stretch forms a random coil conformation and thereby can mediate an increased in vivo and/or in vitro stability. In other embodiments, the PAS sequences that form random coil domain are biologically inert, especially with respect to proteolysis in blood plasma, immunogenicity, isoelectric point/electrostatic behavior, binding to cell surface receptors or internalization, but are still biodegradable, which provides clear advantages over synthetic polymers such as PEG.

Non-limiting examples of the PAS sequences forming random coil conformation comprise an amino acid sequence selected from the group consisting of ASPAAPAPASPAAPAPSAPA, AAPASPAPAAPSAPAPAAPS, and AS AAAP AAAS AAAS AP S AAA, or any combinations thereof (see US Pat. Publ. No. 2010/0292130 A1 and PCT Appl. Publ. No. WO 2008/155134 A1).

In certain embodiments, a heterologous moiety that is linked to the superagonist or superantagonist is hydroxyethyl starch (HES) or a derivative thereof. HES is a derivative of naturally occurring amylopectin and is degraded by alpha amylase in the body, and exhibits advantageous biological properties. It is used as a blood volume replacement agent and in hemodilution therapy in the clinics (Sommermeyer et al., Krankenhauspharmazie, 8(8), 271-278 (1987); and Weidler et al, Arzneim.—Forschung/Drug Res., 41, 494-498 (1991)).

In certain embodiments, a heterologous moiety linked to the superagonist or superantagonist is a mixture of hydroxyethyl starches having different mean molecular weights and/or different degrees of substitution and/or different ratios of C2: C6 substitution.

In certain embodiments, a heterologous moiety that is linked to the superagonist or superantagonist is a polysialic acid (PSAs) or a derivative thereof. Polysialic acids (PSAs) are naturally occurring unbranched polymers of sialic acid produced by certain bacterial strains and in mammals in certain cells Roth J., et al. (1993) in Polysialic Acid: From Microbes to Man, eds Roth J., Rutishauser U., Troy F. A. (Birkhauser Verlag, Basel, Switzerland), pp 335-348. Sialic acid may also be found in alternating copolymers with monomers other than sialic acid. Polysialic acids have important biological functions including the evasion of the immune and complement systems by pathogenic bacteria and the regulation of glial adhesiveness of immature neurons during fetal development (wherein the polymer has an anti-adhesive function; Cho and Troy, P.N.A.S., USA, 91 (1994) 11427-11431). Various methods of attaching or conjugating polysialic acids to a peptide or polypeptide have been described (see U.S. Pat. No. 5,846,951; WO-A-0187922, and US 2007/0191597 A1).

In certain embodiments, the heterologous moiety that is linked to the superagonist or superantagonist is a glycine-rich homo-amino-acid polymer (HAP). The HAP sequence can comprise a repetitive sequence of glycine, which has at least 50 amino acids, at least 100 amino acids, 200 amino acids, or 500 amino acids in length. In one embodiment, the HAP sequence is capable of extending half-life of a moiety fused to or linked to the HAP sequence. Non-limiting examples of the HAP sequence includes, but are not limited to (Gly)n, (Gly4Ser)n or S(Gly4Ser)n, wherein n is 1-200.

In certain aspects, a compound of the invention is covalently linked to at least one heterologous moiety that is or comprises an XTEN polypeptide or fragment, variant, or derivative thereof. As used here "XTEN polypeptide" refers to extended length polypeptides with non-naturally occurring, substantially non-repetitive sequences that are composed mainly of small hydrophilic amino acids, with the sequence having a low degree or no secondary or tertiary structure under physiologic conditions. As a heterologous moiety, XTENs can serve as a half-life extension moiety. In addition, XTEN can provide desirable properties including but are not limited to enhanced pharmacokinetic parameters and solubility characteristics.

In certain aspects, an XTEN moiety can increase pharmacokinetic properties such as longer in vivo half-life or increased area under the curve (AUC), so that a compound or conjugate of the invention stays in vivo and has procoagulant activity for an increased period of time compared to a compound or conjugate with the same but without the XTEN heterologous moiety (See International Patent Publication Nos. WO 2010091122 A1, WO 2010144502 A2, WO 2010144508 A1, WO 2011028228 A1, WO 2011028229 A1, or WO 2011028344 A2).

Within the meaning of the present invention, the term "Fc" is to be understood as immunoglobulin constant region or a portion thereof, such as an Fc region or a FcRn binding partner. In certain embodiments, the compound or conjugate is linked to one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region in a biologically active peptide derivative of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In certain embodiments, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain). In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

An Fc in a biologically active peptide derivative of the invention can include, for example, a change (e.g., a substitution) at one or more of the amino acid positions disclosed in Int'l. PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; U.S. Pat. Publ. Nos. US US2007/0237766, US2007/0237767, US2007/0243188, US2007/0248603, US2007/0286859, US2008/0057056. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

An Fc region used in the invention may also comprise an art recognized amino acid substitution which alters its glycosylation. For example, the Fc has a mutation leading to reduced glycosylation (e.g., N- or O-linked glycosylation) or may comprise an altered glycoform of the wild-type Fc moiety (e.g., a low fucose or fucose-free glycan). In certain embodiments, the compound or conjugate of the invention is linked to a heterologous moiety comprising albumin or a functional fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. 2008/0194481 A1, 2008/0261877 A1, or 2008/0153751 A1 or PCT Appl. Publ. Nos. 2008/033413 A2, 2009/058322 A1, or 2007/021494 A2.

In one embodiment, the heterologous moiety is albumin, a fragment, or a variant thereof which is further linked to a heterologous moiety selected from the group consisting of an immunoglobulin constant region or portion thereof (e.g., an Fc region), a PAS sequence, HES, and PEG.

In certain embodiments, the heterologous moiety is an albumin binding moiety, which comprises an albumin binding peptide, a bacterial albumin binding domain, an albumin-binding antibody fragment, or any combinations thereof.

For example, the albumin binding protein can be a bacterial albumin binding protein, an antibody or an antibody fragment including domain antibodies (see U.S. Pat. No. 6,696,245). An albumin binding protein, for example, can be a bacterial albumin binding domain, such as the one of streptococcal protein G (Konig, T. and Skerra, A. (1998) J. Immunol. Methods 218, 73-83). Other examples of albumin binding peptides that can be used as conjugation partner are, for instance, those as described in US patent application 2003/0069395 or Dennis et al. (Dennis et al. (2002) J. Biol. Chem. 277, 35035-35043). Examples of albumin-binding peptides include a series of peptides having the core sequence DICLPRWGCLW (See, Dennis et al, 2002. J. Biol. Chem 277:35035-35043), albumin-binding antibody fragments are disclosed in Muller and Kontermann, Curr. Opin. Mol. Ther. 9:319-326 (2007), and Holt et al, Prot. Eng. Design Sci., 21:283-288 (2008).

The described superagonist and superantagonist may exist in a cyclized form with an intramolecular disulfide bond between the thiol groups of additional cysteines. Other embodiments include analogs of these disulfide derivatives in which one of the sulfurs has been replaced by a C ¾ group or other isostere for sulfur. These analogs can be made via an intramolecular or intermolecular displacement, using methods known in the art.

Alternatively, the amino-terminus of the peptide can be capped with an alpha-substituted acetic acid, wherein the alpha substituent is a leaving group, such as an oc-haloacetic acid, for example, oc-chloroacetic acid, oc-bromoacetic acid, or oc-iodoacetic acid. The peptides of the present embodiments can be cyclized or dimerized via displacement of the leaving group by the sulfur of the cysteine or homocysteine residue. See, for example, Andreu, et al. 1994, Meth. Mol. Bio. 35(7):91-169; Barker, et al. 1992, Med. Chem. 35:2040-2048; and Or, et al. 1991, Org. Chem. 56:3146-3149).

According to an embodiment of the present invention, the compounds of formula (I), (II), or (III) can be further modified by N-methylation of at least one amide bond. The influence of N-methylation on the metabolic stability of peptides has been described for various peptides. For example, cyclosporine is a naturally occurring, cyclic, multiply N-methylated peptide that exhibits an excellent pharmacokinetic profile. N-methylation in general blocks enzymatic degradation—by proteases as they are unable to cleave N-methylated peptide bonds. Multiple N-methylation was shown to improve the metabolic stability and intestinal permeability of peptides [Chatterjee J, Gilon C, Hoffman A, Kessler H, N-methylation of peptides: a new perspective in medicinal chemistry, Acc Chem Res., 41(10), 1331-1342, 2008]. Cyclization combined with Af-methylation was used to modulate physicochemical properties of peptides, including metabolic stability, membrane permeability and oral bioavailability [Chatterjee J, Laufer B, Kessler H, Synthesis of Af-methylated cyclic peptides, Nat Protoc, 7(3), 432-444, 2012]. Dong Q G, Zhang Y, Wang M S, Feng J, Zhang H H, Wu Y G, Gu T J, Yu X H, Jiang C L, Chen Y, Li W, Kong W, Improvement of enzymatic stability and intestinal permeability of deuterohemin-peptide conjugates by specific multi-site Af-methylation, Amino Acids., 43(6), 2431-2441, 2012, describe that Af-Methylation at selected sites showed high resistance against proteolytic degradation. In diluted serum and intestinal preparation 50- to 140-fold higher half-life values were observed. However, Linde Y, Ovadia O, Safrai E, Xiang Z, Portillo F P, Shalev D E, Haskell-Luevano C, Hoffman A, Gilon C, Structure-activity relationship and metabolic stability studies of backbone cyclization and Af-methylation of melanocortin peptides, Biopolymers., 90(5), 671-682, 2008, describe that cyclic Af-methylated analogues of the a-melanocyte stimulating hormone were more stable, however less biologically active than the parent peptide. It will be understood that two or more such modifications can be coupled in one peptidomimetic structure.

In some embodiments, the modified peptide agonists or antagonists as disclosed and described herein may also represent a prodrug: a prodrug is any compound that undergoes biotransformation before exhibiting its pharmacological effects. Prodrugs could also include a carrier-linked prodrug, a cascade prodrug.

Methods of Use

The present invention further provides a method for treatment and/or prevention of disorders, in particular the disorders mentioned above, using an active amount of the compounds according to the invention, including without limitation endothelial, cardiovascular, pulmonary, lymphatic, edematous and/or inflammatory disorders. Some embodiments provide a method of treating a condition associated with aberrant levels of CGRP, ADM, or IMD comprising the administration of the CLR/RAMP receptor superagonist as disclosed and described herein, to an individual, the method comprising administering to the individual an effective amount of a CLR/RAMP receptor superagonist as disclosed and described herein.

For the present invention, the term "treatment" or "treating" includes inhibiting, delaying, relieving, mitigating, arresting, reducing, or causing the regression of a disease, disorder, condition, or state, the development and/or progression thereof, and/or the symptoms thereof. The term "prevention" or "preventing" includes reducing the risk of having, contracting, or experiencing, a disease, disorder, condition, or state, the development and/or progression thereof, and/or the symptoms thereof. The term prevention includes prophylaxis. Treatment or prevention of a disease, disorder, condition, or state may be partial or complete.

In light of the pharmacologic activities of CLR/RAMP agonists and antagonists, numerous clinical indications are evident, and include without limitation hypertension, for example pregnancy hypertension; preeclampsia; eclampsia; malignant hypertension, pulmonary arterial hypertension, hypertension associated with diabetes, etc.; heart failure, stroke, myocardial infarction; cardiac hypertrophy; osteoarthritis; bronchopulmonary dysplasia (BPD); chronic obstructive pulmonary disease (COPD); emphysema; lung fibrosis; ulcerative colitis; wound healing; diabetic ulcer; lymphedema; rheumatoid arthritis; neuroprotection, and the like For example, clinical indications for which a superagonist of the invention may find use include particularly the treatment of malignant hypertension. The peptides of the invention provide for a decrease in blood pressure, e.g. systolic pressure of at least about 5%, at least about 10%, at least about 15%, at least about 20% or more, without affecting heart rate.

In methods of use, an effective dose of a peptide of the invention is administered alone or in a cocktail of peptides, or combined with additional active agents for the treatment of a condition as listed above. The effective dose may be from about 1 ng/kg weight, 10 ng/kg weight, 100 ng/kg weight, 1 µg/kg weight, 10 µg/kg weight, 25 µg/kg weight, 50 µg/kg weight, 100 µg/kg weight, 250 µg/kg weight, 500 µg/kg weight, 750 µg/kg weight, 1 mg/kg weight, 5 mg/kg weight, 10 mg/kg weight, 25 mg/kg weight, 50 mg/kg weight, 75 mg/kg weight, 100 mg/kg weight, 250 mg/kg weight, 500 mg/kg weight, 750 mg/kg weight, and the like. The dosage may be administered multiple times as needed, e.g. every 30 minutes, every hour, every 2 hours, every 4 hours, every 6 hours, every 8 hours, every 12 hours, every 18 hours, daily, every 2 days, every 3 days, weekly, and the like. The dosage may also be administered as a continuous infusion, e.g. in acute treatment methods.

The peptides of the invention find use in reducing hypertension associated with preeclampsia and eclampsia, and may be administered for a period of time sufficient to stabilize the subject and allow for safe delivery of the pregnancy.

Preeclampsia is new-onset hypertension and proteinuria after 20 wk gestation. Eclampsia is unexplained generalized seizures in patients with preeclampsia. Diagnosis is clinical and by urine protein measurement. Conventional treatment is usually with IV Mg sulfate and delivery at term. Preeclampsia affects 3 to 7% of pregnant women. Preeclampsia and eclampsia develop after 20 wk gestation; up to 25% of cases develop postpartum, most often within the first 4 days but sometimes up to 6 wk postpartum. Untreated preeclampsia usually smolders for a variable time, then suddenly progresses to eclampsia, which occurs in 1/200 patients with preeclampsia. Untreated eclampsia is usually fatal.

Preeclampsia may be asymptomatic or may cause edema or excessive weight gain. Nondependent edema, such as facial or hand swelling (the patient's ring may no longer fit her finger), is more specific than dependent edema. Reflex reactivity may be increased, indicating neuromuscular irritability, which can progress to seizures (eclampsia). Petechiae may develop, as may other signs of coagulopathy.

Diagnosis is of new-onset hypertension (BP >140/90 mm Hg) plus new unexplained proteinuria >300 mg/24 h after 20 wk. Diagnosis is suggested by symptoms or presence of hypertension, defined as systolic BP >140 mm Hg, diastolic BP >90 mm Hg, or both. Except in emergencies, hypertension should be documented in >2 measurements taken at least 4 h apart. Urine protein excretion is measured in a 24-h collection. Proteinuria is defined as >300 mg/24 h. Alternatively, proteinuria is diagnosed based on a protein:creatinine ratio ≥0.3 or a dipstick reading of 1+ (used only if other quantitative methods are not available). Absence of proteinuria on less accurate tests (e.g., urine dipstick testing, routine urinalysis) does not rule out preeclampsia.

In the absence of proteinuria, preeclampsia is also diagnosed if pregnant women have new-onset hypertension plus new onset of any of the following: Thrombocytopenia (platelets <100,000/µL); Renal insufficiency (serum creatinine >1.1 mg/dL or doubling of serum creatinine in women without renal disease), Impaired liver function (aminotransferases >2 times normal), Pulmonary edema, Cerebral or visual symptoms.

Hypertension is a disease which, if untreated, strongly predisposes to atherosclerotic cardiovascular disease. It is estimated that as many as 1 in 4 adult Americans have hypertension. Hypertension is approximately twice as common in persons with diabetes as in those without. The prevalence of hypertension increases with age.

Hypertension should not be diagnosed on the basis of a single measurement. Initial elevated readings should be confirmed on at least two subsequent visits over one week or more with average diastolic blood pressure of 90 mmHg or greater or systolic blood pressure of 140 mmHg or greater required for diagnosis of hypertension. Special care is warranted in diagnosing hypertension in persons with diabetes because of greater variability of blood pressure and a much greater likelihood of isolated systolic hypertension. A goal blood pressure of less than 130/85 mmHg is recommended for these patients.

In addition to dietary changes, pharmacological treatment may be required to control high blood pressure. The subject peptides may be administered to reduce arterial blood pressure. In addition, a secondary effect of reducing hypertension is reduction of edema and inflammatory exudate volume.

Pharmaceutical compositions containing peptides of the invention are useful as cardioprotective agents, e.g. to ameliorate ischemic injury or myocardial infarct size consequent to myocardial ischemia. The development of new therapeutic agents capable of limiting the extent of myocardial injury, i.e., the extent of myocardial infarction, following acute myocardial ischemia is a major concern of modern cardiology. There has also been interest in the development of therapies capable of providing additional myocardial protection which could be administered in conjunction with thrombolytic therapy, or alone, since retrospective epidemiological studies have shown that mortality during the first few years following infarction appears to be related to original infarct size.

Myocardial ischemia is the result of an imbalance of myocardial oxygen supply and demand and includes exertional and vasospastic myocardial dysfunction. Exertional ischemia is generally ascribed to the presence of critical atherosclerotic stenosis involving large coronary arteries resulting in a reduction in subendocardial flow. Vasospastic ischemia is associated with a spasm of focal variety, whose onset is not associated with exertion or stress. The spasm is better defined as an abrupt increase in vascular tone.

The compounds of this invention can be normally administered orally or parenterally, in the treatment of patients in need of cardioprotective therapy. The dosage regimen is that which insures maximum therapeutic response until improvement is obtained and thereafter the minimum effective level that gives relief. Thus, in general, the dosages are those that are therapeutically effective in producing a cardioprotective effect, i.e., amelioration of ischemic injury or myocardial infarct size consequent to myocardial ischemia. It is also anticipated that the peptides would be useful as an injectable dosage form which may be administered in an emergency to a patient suffering from myocardial ischemia, etc.

The peptides of the invention also find use in the reduction of edema, for example in lymphedema, rheumatoid arthritis, edema secondary to brain tumors or irradiation for cancer, edema resulting from stroke, head trauma or spinal cord injury, post-surgical edema, asthma and other respiratory diseases and cystoid macular edema of the eye.

On the basis of their pharmacological properties, the compounds according to the invention can be employed for treatment and/or prevention of cardiovascular diseases, in particular heart failure, especially chronic and acute heart failure, worsening heart failure, diastolic and systolic (congestive) heart failure, acute decompensated heart failure, cardiac insufficiency, coronary heart disease, angina pectoris, myocardial infarction, ischemia reperfusion injury, ischemic and hemorrhagic stroke, arteriosclerosis, atherosclerosis, hypertension, especially essential hypertension, malignant essential hypertension, secondary hypertension, renovascular hypertension and hypertension secondary to renal and endocrine disorders, hypertensive heart disease, hypertensive renal disease, pulmonary hypertension, especially secondary pulmonary hypertension, pulmonary hypertension following pulmonary embolism with and without acute cor pulmonale, primary pulmonary hypertension, and peripheral arterial occlusive disease.

The compounds according to the invention are furthermore suitable for treatment and/or prevention of pulmonary disorders, such as chronic obstructive pulmonary disease, asthma, acute and chronic pulmonary edema, allergic alveolitis and pneumonitis due to inhaled organic dust and particles of fungal, actinomycetic or other origin, acute chemical bronchitis, acute and chronic chemical pulmonary edema, neurogenic pulmonary edema, acute and chronic pulmonary manifestations due to radiation, acute and chronic interstitial lung disorders, acute lung injury/acute respiratory distress syndrome (ALI/ARDS) in adult or child including newborn, ALI/ARDS secondary to pneumonia and sepsis, aspiration pneumonia and ALI/ARDS secondary to aspiration, ALI/ARDS secondary to smoke gas inhalation, transfusion-related acute lung injury (TRALI), ALI/ARDS or acute pulmonary insufficiency following surgery, trauma or burns, ventilator induced lung injury (VILI), pulmonary fibrosis, and mountain sickness.

The compounds according to the invention are furthermore suitable for treatment and/or prevention of gestational [pregnancy-induced] edema and proteinuria with and without hypertension (pre-eclampsia and eclampsia).

The compounds according to the invention are furthermore suitable for treatment and/or prevention of chronic kidney diseases, renal insufficiency, diabetic nephropathy, hypertensive chronic kidney disease, glomerulonephritis, rapidly progressive and chronic nephritic syndrome, unspecific nephritic syndrome, nephrotic syndrome, hereditary nephropathies, acute and chronic tubulo-interstitial nephritis, acute kidney injury, acute kidney failure, traumatic and post procedural kidney injury, cardiorenal syndrome, and protection and functional improvement of kidney transplants.

The compounds are moreover suitable for treatment and/or prevention of diabetes mellitus and its consecutive symptoms, such as e.g. diabetic macro- and microangiopathy, diabetic nephropathy and neuropathy.

The compounds according to the invention can be used for treatment and/or prevention of disorders of the central and peripheral nervous system such as migraine, cluster headache, epilepsy, stroke, vasospasm, viral and bacterial meningitis and encephalitis (e.g. Zoster encephalitis), traumatic and toxic brain injury, primary or secondary malignant neoplasm of the brain and spinal cord, radiculitis and polyradiculitis, Guillain-Barre syndrome [acute or postinfective polyneuritis, Miller Fisher Syndrome], Parkinson's disease, acute and chronic polyneuropathies, pain, cerebral edema, Alzheimer's disease, degenerative diseases of the nervous system and demyelinating diseases of the central nervous system such as but not restricted to multiple sclerosis.

The compounds according to the invention are furthermore suitable for treatment and/or prevention of portal hypertension and liver fibrosis [cirrhosis] and its sequelae such as esophageal varices and ascites, for the treatment and/or prevention of pleural effusions secondary to malignancies or inflammations and for the treatment and/or prevention of primary and secondary lymphedema and of edema secondary to varices.

The compounds according to the invention are furthermore suitable for treatment and/or prevention of inflammatory disorders of the gastrointestinal tract such as inflammatory bowel disease, Crohn's disease, ulcerative colitis, and toxic and vascular disorders of the intestine. The compounds according to the invention are furthermore suitable for treatment and/or prevention of sepsis, hemorrhagic shock, or multi organ failure (MOF), traumatic shock, and angioneurotic edema [Giant urticaria, Quincke's edema].

The compounds according to the invention are furthermore suitable for treatment of edematous ocular disorders or ocular disorders associated with disturbed vascular function, including, but not being limited to, age-related macular degeneration (AMD), diabetic retinopathy, in particular diabetic macula edema (DME), subretinal edema, and intraretinal edema. In the context of the present invention, the term age-related macular degeneration (AMD) encompasses both wet (or exudative, neovascular) and dry (or non-exudative, non-neovascular) manifestations of AMD. The compounds according to the invention are furthermore suitable for treatment of ocular hypertension (glaucoma).

The compounds according to the invention can moreover be used for treatment and/or prevention of operation-related states of ischemia and consecutive symptoms thereof after surgical interventions, in particular interventions on the heart using a heart-lung machine, interventions on the carotid arteries, aorta, or with instrumental opening or penetration of the skull cap. The compounds are furthermore suitable for general treatment and/or prevention in the event of surgical interventions with the aim of accelerating wound healing and shortening the reconvalescence time. They are further suited for the promotion of wound healing.

The compounds are furthermore suitable for treatment and/or prevention of disorders of bone density and structure such as but not restricted to osteoporosis, osteomalacia and hyperparathyroidism-related bone disorders.

The present invention further provides for the use of the compounds according to the invention for preparing a medicament for treatment and/or prevention of disorders, in particular the disorders mentioned above.

The invention further provides medicaments comprising a compound according to the invention and one or more further active ingredients, in particular for treatment and/or prevention of the disorders mentioned above. Exemplary and preferred active ingredient combinations are:

ACE inhibitors, angiotensin receptor antagonists, beta-2 receptor agonists, phosphodiesterase inhibitors, glucocorticoid receptor agonists, diuretics, or angiotensin converting enzyme-2 or acetylsalicylic acid (aspirin). In a preferred embodiment of the invention, the compounds according to the invention are administered in combination with an ACE inhibitor, such as, by way of example and preferably, enalapril, quinapril, captopril, lisinopril, ramipril, delapril, fosinopril, perindopril, cilazapril, imidapril, benazepril, moexipril, spirapril or trandopril. In a preferred embodiment of the invention, the compounds according to the invention are administered in combination with an angiotensin receptor antagonist, such as, by way of example and preferably, losartan, candesartan, valsartan, telmisartan or embusartan.

In an embodiment of the invention, the compounds according to the invention are administered in combination with a beta-2 receptor agonist, such as, by way of example and preferably, salbutamol, pirbuterol, salmeterol, terbutalin, fenoterol, tulobuterol, clenbuterol, reproterol or formoterol.

In an embodiment of the invention, the compounds according to the invention are administered in combination with a phosphodiesterase (PDE) inhibitor, such as, by way of example and preferably, milrinone, amrinone, pimobendan, cilostazol, sildenafil, vardenafil or tadalafil.

In an embodiment of the invention, the compounds according to the invention are administered in combination with a glucocorticoid receptor agonist, such as, by way of example and preferably, cortisol, cortisone, hydrocortisone, prednisone, methyl-prednisolone, prednylidene, deflazacort, fluocortolone, triamcinolone, dexamethasone or betamethasone.

In an embodiment of the invention, the compounds according to the invention are administered in combination with diuretics, such as, by way of example and preferably, furosemide, torasemide and hydrochlorothiazide.

In an embodiment of the invention, the compounds according to the invention are administered in combination with natriuretic peptides, such as nesiritide (human B-type natriuretic peptide (hBNP)) and carperitide (alpha-human atrial natriuretic polypeptide (hANP)).

In an embodiment of the invention, the compounds according to the invention are administered in combination with urodilatin, a derivative of ANP still under development for acute heart failure.

In an embodiment of the invention, the compounds according to the invention are administered in combination with LCZ696 (Entresto), a neprilysin (enkephalinase, neutral endopeptidase, NEP, also involved in the metabolism of ADM) inhibitor.

In an embodiment of the invention, the compounds according to the invention is used to stimulate the propagation of endothelial or lymphendothelial cell from humans or animals in vitro or in vivo. Endothelial dysfunction is a leading cause of micro and macrovascular complications in a variety of life-threatening diseases, including atherosclerosis, cardiomyopathy, stoke, resistant hypertension, preeclampsia, pulmonary arterial hypertension, and diabetic ulcers. Endothelial dysfunction represents an early event along the natural course of these diseases. The function of vascular endothelium includes the synthesis of substances that modulate vascular tone, the inhibition of platelet aggregation, and control of proliferation of vascular cells. Damage to the endothelium can lead to increased endothelium-derived contracting factors, reduced nitric oxide production, and breakdown of endothelial barriers, leading to hypertension, atherosclerosis, thrombosis, inflammation, vascular resistance, vascular leakage, edema, and functional impairment in many organs. Because of this there has been a significant interest in finding methods to ameliorate endothelial dysfunction. In the last decades, the development of several classes of antihypertensive and vasoprotective drugs including, angiotensin converting enzyme (ACE) inhibitors, angiotensin-receptor antagonists (ARBs), mineralocorticoid receptor antagonists, beta-blockers, diuretics, and calcium channel antagonists, has dramatically improved the outcomes of patients with some of the endothelial dysfunction-associated diseases by reducing oxidative stress, endothelin activity, plasminogen activator activity, or platelet activation. In addition, statins and anti-diabetes drug metformin, and inhibitor of xanthine oxidase such as allopurinol have been shown to improve endothelial functions in patients. However, the progression of many of the endothelial dysfunction-associated diseases cannot be prevented by existing drugs, which were mainly developed to block signaling processes, not to actively stimulate endothelial functions. The present invention can be used applied to prevent or treat endothelial dysfunction in a variety of diseases, and to facilitate efficient propagation of endothelial cells, which can be applied for the treatment of endothelial dysfunction in its own right.

Formulations

Formulations and medicaments are provided that comprise at least one compound according to the invention, normally together with one or more inert, nontoxic, pharmaceutically suitable excipients and to the use thereof for the aforementioned purposes. For this purpose, they can be administered in a suitable way, for example by the parenteral, pulmonary, nasal, sublingual, lingual, buccal, dermal, transdermal, conjunctival, optic route or as implant or stent. The active agent can be a single peptide disclosed herein; or may be formulated as a cocktail of one or more peptides, e.g. 1, 2, 3, 4, 5, 6, 7 8, 9, 10 or more different peptides, e.g. a peptide comprising, consisting or consisting essentially of the structure of a peptide sequence of Table 1; or comprising, consisting or consisting essentially of an amino acid sequence having at least 60%, at least 70%, at least 80%, at least 90%, at least 95% or more sequence identity to the amino acid sequence of SEQ ID NOS: 28-51, 69-70, 92, 94, 101, 103, and 110, wherein said peptide retains agonist or superagonist activity. The peptide may be provided as a pharmaceutical acceptable salt.

Some embodiments include pharmaceutical compositions comprising, as an active ingredient, at least one of the instant modified peptides (D-amino acids or peptidomimetics) disclosed herein in association with a pharmaceutical carrier or diluent. These pharmaceutical compositions can be administered by any means, as known to those of skill in the art, and include, without limitation, oral, pulmonary, parenteral (intramuscular, intraperitoneal, intravenous, or subcutaneous injection), inhalational (via a fine powder formulation, or aerosol), transdermal, intranasal or sublingual routes of administration and can be formulated in dosage forms appropriate for each route of administration. The compounds can also be administered in sustained or controlled release dosage forms, including without limitation, depot injections, osmotic pumps, transdermal (including electrotransport) patches, and the like, for prolonged and/or timed, pulsed administration at a predetermined rate.

The pharmaceutical compositions of the present embodiments may be manufactured in a manner that is itself known, e.g., by means of conventional mixing, dissolving, granulating, dragee-making, levigating, emulsifying, encapsulating, entrapping or tabletting processes. Pharmaceutical compositions for use in accordance with the present embodiments thus may be formulated in conventional manner using one or more physiologically acceptable carriers comprising excipients and auxiliaries which facilitate processing of the active compounds into preparations which can be used pharmaceutically. Any of the well-known techniques, carriers, and excipients may be used as suitable and as understood in the art.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For administration by inhalation, the instant compounds for use according to the present embodiments are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. As an example, preparations for administration by inhalation may be prepared according to the teaching of Quay, et al., U.S. Pat. No. 7,812,120 B2.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eye drops, or in gellan gum; ophthalmic ointments; ophthalmic suspensions, such as microparticulates, drug-containing small polymeric particles that are suspended in a liquid carrier medium, lipid-soluble formulations; and ocular inserts. All of the above-mentioned references are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in, many respects nasal secretions to ensure maintenance of normal ciliary action, such compositions include, for example and without limitation, the nasal solutions disclosed by Azria, et al., in U.S. Pat. No. 5,733,569. Pharmaceutical formulations for intraauricular delivery include suspensions and ointments for topical application in the ear. Common solvents for such aural formulations include glycerin and water.

In addition to the formulations described previously, the instant compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Non-limiting examples of methods of administration include, among others, (a) administration though non-oral pathways such as intraocular, intranasal or intraauricular, which administration includes administration as an aqueous suspension, an oily preparation or the like or as a drip, spray, salve, ointment or the like; (b) administration via injection, subcutaneously, intraperitoneally, intravenously, intramuscularly, intradermally, intraorbitally or the like, including infusion pump delivery; (c) administration locally such as by injection directly intracranially, e.g., by depot implantation; as well as (e) administration topically; as deemed appropriate by those of skill in the art for bringing the peptide of the present embodiments into contact with living tissue.

The exact formulation, route of administration and dosage for the pharmaceutical compositions of the present embodiments can be chosen by the individual physician in view of the patient's condition. Typically, the dose range of the composition administered to the patient can be from about 0.000001 to 100 mg/kg of the patient's body weight. The dosage may be a single one or a series of two or more given in the course of one or more days, as is needed by the patient. In instances where human dosages for compounds have been established for at least some condition, the present embodiments will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an intravenous, subcutaneous, or intramuscular dose of each active ingredient at an exemplary range of between 0.001 mg and 100 mg, or an exemplary range of between 0.005 mg and 5 mg. In cases of administration of a pharmaceutically acceptable salt, dosages may be calculated as the free base. In some embodiments, the composition is administered 0.1 to 4 times per day or as a single acute dose, for example to ameliorate hypertension. Alternatively the compositions as described herein may be administered by continuous intravenous infusion, preferably at a dose of each active ingredient up to 1000 mg per day. As will be understood by those of skill in the art, in certain situations it may be necessary to administer the peptides disclosed herein in amounts that exceed, or even far exceed, the above-stated, exemplary dosage range in order to effectively and aggressively treat particularly aggressive diseases or infections. In some embodiments, the peptides will be administered for a period of continuous therapy, for example for a week or more, or for months or years.

In cases of local administration or selective uptake, the effective local concentration of the drug may not be related to plasma concentration. The amount of the instant composition administered may be dependent on the subject being treated, on the subject's weight, the severity of the affliction, and the manner of administration.

Compounds disclosed herein can be evaluated for efficacy and toxicity using known methods. The results of such studies are often predictive of efficacy in animals, such as mammals, or more specifically, humans. Alternatively, the efficacy of particular compounds in an animal model, such as mice, rats, rabbits, or monkeys, may be determined using known methods.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose".

The compositions described herein can also be microencapsulated by, for example, the method of Tice and Bibi (in: *Treatise on Controlled Drug Delivery*, ed. A. Kydonieus, Marcel Dekker, N.Y. 1992, pp. 315-339).

The agonist peptides and peptidomimetics described herein are effective in treating CLR/RAMP receptor-mediated conditions when administered at an exemplary dosage range of, for example, from about 0.01 µg to about 50 mg/kg of body weight per day. The specific dose employed is regulated by the particular condition being treated, the route of administration as well as by the judgment of the attending clinician depending upon factors such as the severity of the condition, the age and general condition of the patient, and the like. Such doses can be readily determined by those of skill in the art.

Injectables can be prepared in conventional forms, either as liquid solutions, suspensions, solid forms suitable for solution or suspension in liquid prior to injection, emulsions, or lyophilized powder in association with a pharmaceutically acceptable parenteral vehicle. Examples of such vehicles are water, saline, Ringer's solution, dextrose solution, and 5% human serum albumin. Liposomes and non-aqueous vehicles such as fixed oils may also be used. The vehicle or lyophilized powder may contain additives that maintain isotonicity (for example, sodium chloride, mannitol) and chemical stability (for example, buffers and preservatives). The formulation is sterilized by commonly used techniques. For example, a parenteral composition suitable for administration by injection is prepared by dissolving 1.5% by weight of active ingredient in 0.9% sodium chloride solution.

The compounds can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, poly anhydrides, polyglycolic acid, collagen, polyorthoesters, polylactic acid (PLA), polylactic, polyglycolic copolymers (PLG), or poly(lactic-co-glycolic acid) (PLGA). Many methods for the preparation of such formulations are generally known to those skilled in the art.

Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized. The compositions may take such forms as suspensions, solutions or emulsions in oily or aqueous vehicles, and may contain formulatory agents such as suspending, stabilizing and/or dispersing agents. Aqueous injection suspensions may contain substances which increase the viscosity of the suspension, such as sodium carboxymethyl cellulose, sorbitol, or dextran.

For transmucosal administration, penetrants appropriate to the barrier to be permeated may be used in the formulation. Suitable lipophilic solvents or vehicles include fatty oils such as sesame oil, or other organic oils such as soybean, grapefruit or almond oils, or synthetic fatty acid esters, such as ethyl oleate or triglycerides, or liposomes.

For administration by inhalation, the instant compounds for use according to the present embodiments are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. As an example, preparations for administration by inhalation may be prepared according to the teaching of Quay, et al., U.S. Pat. No. 7,812,120 B2, issued Oct. 12, 2010.

The compositions described herein can also be microencapsulated by, for example, the method of Tice and Bibi (in: Treatise on Controlled Drug Delivery, ed. A. Kydonieus, Marcel Dekker, N.Y. 1992, pp. 315-339).

Further disclosed herein are various pharmaceutical compositions well known in the pharmaceutical art for uses that include intraocular, intranasal, and intraauricular delivery. Pharmaceutical compositions for intraocular delivery include aqueous ophthalmic solutions of the active compounds in water-soluble form, such as eye drops, or in gellan gum (Shedden et al, 2001, Clin. Ther., 23(3):440-50) or hydrogels (Mayer et al., 1996, Ophthalmologica, 210(2): 101-3); ophthalmic ointments; ophthalmic suspensions, such as microparticulates, drug-containing small polymeric particles that are suspended in a liquid carrier medium (Joshi, A., 1994. Ocul. Pharmacol, 10(1):29-45), lipid-soluble formulations (Aim et al, 1989 Prog. Clin. Biol. Res., 312:447-58), and microspheres (Mordenti, 1999, Toxicol. Sci., 52(1):101-6); and ocular inserts.

Pharmaceutical compositions for intranasal delivery may also include drops and sprays often prepared to simulate in many respects nasal secretions to ensure maintenance of normal ciliary action, such compositions include, for example and without limitation, the nasal solutions disclosed by Azria, et al., in U.S. Pat. No. 5,733,569, issued Mar. 31, 1998. As disclosed in Remington's Pharmaceutical Sciences, 18th Ed., Mack Publishing Co., Easton, Pa. (1990), and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Non-limiting examples of methods of administration include, among others, (a) administration via injection, subcutaneously, intraperitoneally, intravenously, intramuscularly, intradermally, intraorbitally or the like, including infusion pump delivery; (b) administration locally such as by injection directly intracranially, e.g., by depot implantation; as well as (c) administration topically; as deemed appropriate by those of skill in the art for bringing the peptide of the present embodiments into contact with living tissue.

Typically, the dose range of the composition administered to the patient can be from about 0.000001 to 100 mg/kg of the patient's body weight. The dosage may be a single one or a series of two or more given in the course of one or more days, as is needed by the patient. Dosage amount and interval may be adjusted individually to provide plasma levels of the active moiety which are sufficient to maintain the modulating effects, or minimal effective concentration (MEC). Dosage intervals can also be determined using MEC value. Compositions should be administered using a regimen which maintains plasma levels above the MEC for 10-90% of the time.

Throughout the specification, any recitation of a particular compound should be understood to encompass that compound and any (other) pharmaceutically acceptable salt thereof.

Some embodiments provide a CLR/RAMP receptor superagonist or superantagonist having the structure selected from the following peptide sequences, listed in Table 1.

TABLE 1

List of synthetic CLR/RAMP receptor agonist and antagonist sequences

| Sequence | |
|---|---|
| $B^0-B^1-B^2-C-B^4-B^5-G-B^7-C-B^9-B^{10}-B^{11}-B^{12}-B^{13}-B^{14}-B^{15}-B^{16}-B^{17}-B^{18}-B^{19}-B^{20}-B^{21}$ | (SEQ ID NO: 1) |
| miniPEG-K(PAL)GCRFGTCTVQKLAHQIYQFT- | (SEQ ID NO: 2) |
| miniPEG-K(PAL)GCRFGTCTVQKLAHLWQLM- | (SEQ ID NO: 3) |
| Pal-KGCRFGTCTVQKLAHQIYQFT- | (SEQ ID NO: 4) |
| Pal-KGCRFGTCTVQKLAHLWQLM- | (SEQ ID NO: 5) |

TABLE 1-continued

List of synthetic CLR/RAMP receptor agonist and antagonist sequences

| | |
|---|---|
| Ace-K(PAL)GCRFGTCTVQKLAHQIYQFT- | (SEQ ID NO: 6) |
| Ace-K(PAL)GCRFGTCTVQKLAHLWQLM- | (SEQ ID NO: 7) |
| Pal-K(Pal)GCRFGTCTVQKLAHQIYQFT- | (SEQ ID NO: 8) |
| Pal-KTKKTLRTGCRFGTCTVQKLAHQIYQFT- | (SEQ ID NO: 9) |
| Ace-TK(Pal)KTLRTGCRFGTCTVQKLAHQIYQFT- | (SEQ ID NO: 10) |
| Ace-TK(Pal)KTLRTGCRFGTCTVQKLAHQIYQFT- | (SEQ ID NO: 11) |
| min iPEG-TK(Pal)KTLRTGC RFGTCTVQKLAHQIYQFT- | (SEQ ID NO: 12) |
| miniPEG-K(PAL)CRFGTCTVQKLAHQIYQFT- | (SEQ ID NO: 13) |
| Pal-KCRFGTCTVQKLAHQIYQFT- | (SEQ ID NO: 14) |
| Pal-GCRFGTCTVQKLAHQIYQFT- | (SEQ ID NO: 15) |
| Pal-CRFGTCTVQKLAHQIYQFT- | (SEQ ID NO: 16) |
| $C^1$-$C^2$-$C^3$-$C^4$-$C^5$-$C^6$-$C^7$-$C^8$-$C^9$-$C^{10}$-$C^{11}$-$C^{12}$ | (SEQ ID NO: 17) |
| DKDKDNVAPRSK- | (SEQ ID NO: 18) |
| DKDKDNSAPVDP- | (SEQ ID NO: 19) |
| PAGRQDSAPVDP- | (SEQ ID NO: 20) |
| DKDKDNVAPVDP- | (SEQ ID NO: 21) |
| DKDKQDSAPVDP- | (SEQ ID NO: 22) |
| DKGRQDSAPVDP- | (SEQ ID NO: 23) |
| DKDKDSAPVDP- | (SEQ ID NO: 24) |
| DKDKSAPVDP- | (SEQ ID NO: 25) |
| DKDSAPVDP- | (SEQ ID NO: 26) |
| $D^1$-$D^2$-$D^3$-$D^4$-$D^5$-$D^6$-$NH_2$ | (SEQ ID NO: 27) |

Pan-specific superagonist peptide sequence

| | |
|---|---|
| miniPEG-K(PAL)GCRFGTCTVQKLAHQIYQFTDKDKDNSAPVDPSSPHSY-$NH_2$ | (SEQ ID NO: 28) |
| miniPEG-K(PAL)GCRFGTCTVQKLAHQIYQFTPAGRQDSAPVDPSSPHSY-$NH_2$ | (SEQ ID NO: 29) |
| Pal-KGCRFGTCTVQKLAHQIYQFTDKDKDNSAPVDPSSPHSY-$NH_2$ | (SEQ ID NO: 30) |
| Pal-KGCRFGTCTVQKLAHQIYQFTPAGRQDSAPVDPSSPHSY-$NH_2$ | (SEQ ID NO: 31) |
| Ace-K(PAL)GCRFGTCTVQKLAHQIYQFTDKDKDNSAPVDPSSPHSY-$NH_2$ | (SEQ ID NO: 32) |
| Ace-K(PAL)GCRFGTCTVQKLAHQIYQFTPAGRQDSAPVDPSSPHSY-$NH_2$ | (SEQ ID NO: 33) |
| Pal-KGCRFGTCTVQKLAHQIYQFTDKDKDNVAPVDPSSPHSY-$NH_2$ | (SEQ ID NO: 34) |
| Pal-KGCRFGTCTVQKLAHQIYQFTDKDKQDSAPVDPSSPHSY-$NH_2$ | (SEQ ID NO: 35) |
| Pal-KGCRFGTCTVQKLAHQIYQFTDKGRQDSAPVDPSSPHSY-$NH_2$ | (SEQ ID NO: 36) |
| Pal-K(Pal)GCRFGTCTVQKLAHQIYQFTDKDKDNSAPVDPSSPHSY-$NH_2$ | (SEQ ID NO: 37) |
| Pal-KTKKTLRTGCRFGTCTVQKLAHQIYQFTDKDKDNSAPVDPSSPHSY-$NH_2$ | (SEQ ID NO: 38) |
| Ace-TK(Pal)KTLRTGCRFGTCTVQKLAHQIYQFTDKDKDNSAPVDPSSPHSY-$NH_2$ | (SEQ ID NO: 39) |
| Pal-KTKKTLRTGCRFGTCTVQKLAHQIYQFTDKDKDNVAPVDPSSPHSY-$NH_2$ | (SEQ ID NO: 40) |
| Ace-TK(Pal)KTLRTGCRFGTCTVQKLAHQIYQFTDKDKDNVAPVDPSSPHSY-$NH_2$ | (SEQ ID NO: 41) |
| miniPEG-TK(Pal)KTLRTGCRFGTCTVQKLAHQIYQFTDKDKDNVAPVDPSSPHSY-$NH_2$ | (SEQ ID NO: 42) |

TABLE 1-continued

List of synthetic CLR/RAMP receptor agonist and antagonist sequences

| | |
|---|---|
| miniPEG-K(PAL)CRFGTCTVQKLAHQIYQFTDKDKDNSAPVDPSSPHSY-NH$_2$ | (SEQ ID NO: 43) |
| Pal-KCRFGTCTVQKLAHQIYQFTDKDKDNSAPVDPSSPHSY-NH$_2$ | (SEQ ID NO: 44) |
| Pal-GCRFGTCTVQKLAHQIYQFTDKDKDNSAPVDPSSPHSY-NH$_2$ | (SEQ ID NO: 45) |
| miniPEG-K(PAL)GCRFGTCTVQKLAHQIYQFTDKDKDSAPVDPSSPHSY-NH$_2$ | (SEQ ID NO: 46) |
| miniPEG-K(PAL)GCRFGTCTVQKLAHQIYQFTDKDKSAPVDPSSPHSY-NH$_2$ | (SEQ ID NO: 47) |
| miniPEG-K(PAL)GCRFGTCTVQKLAHQIYQFTDKDSAPVDPSSPHSY-NH$_2$ | (SEQ ID NO: 48) |
| miniPEG-K(PAL)GCRFGTCTVQKLAHQIYQFTPAGRQDSAPVDPSSPHSY-NH$_2$ | (SEQ ID NO: 49) |
| miniPEG-K(PAL)GCRFGTCTVQKLAHQIYQFTDKDKDNVAPVDPSSPHSY-NH$_2$ | (SEQ ID NO: 50) |
| miniPEG-K(PAL)GCRFGTCTVQKLAHQIYQFTDKDKQDSAPVDPSSPHSY-NH$_2$ | (SEQ ID NO: 51) |
| Pal-KGCRFGTCTVQKLAHQIYQFTDKDSAPVDPSSPHSY-NH$_2$ | (SEQ ID NO: 92) |

Wild-type IMD, ADM, and CGRP

| | |
|---|---|
| Ace-VGCVLGTCQVQNLSHRLWQLMGPAGRQDSAPVDPSSPHSY-NH$_2$ | (SEQ ID NO: 52) |
| Ace-FGCRFGTCTVQKLAHQIYQFTDKDKDNVAPRSKISPQGY-NH$_2$ | (SEQ ID NO: 53) |
| Ace-YRQSMNNFQGLRSFGCRFGTCTVQKLAHQIYQFTDKDKDNVAPRSKISPQGY-NH$_2$ | (SEQ ID NO: 54) |
| ACNTATCVTHRLAGLLLSRSGGMVKSNFVPINVGSKAF-NH$_2$ | (SEQ ID NO: 143) |

Inactive or low potency agonistic chimeric peptide sequence

| | |
|---|---|
| Ace-VGCRFGTCTVQKLAHQIYQFTDKDKDNVAPRSKSSPHSY-NH$_2$ | (SEQ ID NO: 55) |
| Ace-VGCRFGTCTVQKLAHQIYQFTDKDKDNSAPVDPSSPHSY-NH$_2$ | (SEQ ID NO: 56) |
| Ace-VGCRFGTCTVQKLAHQIYQFTPAGRQDSAPVDPSSPHSY-NH$_2$ | (SEQ ID NO: 57) |
| Ace-VGCRFGTCTVQKLAHLWQLMGPAGRQDSAPVDPSSPHSY-NH$_2$ | (SEQ ID NO: 58) |
| Ace-KGCRFGTCTVQKLAHQIYQFTDKDKDNSAPVDPSSPHSY-NH$_2$ | (SEQ ID NO: 59) |
| Ace-KGCRFGTCTVQKLAHQIYQFTDKDKDNVAPVDPSSPHSY-NH$_2$ | (SEQ ID NO: 60) |
| miniPEG-K(PAL)GCRFGTCTVQKLAHQIYQFTDKDKDNVAPRSKSSPHSY-NH$_2$ | (SEQ ID NO: 61) |
| miniPEG-K(PAL)GCRFGTCTVQKLAHLWQLMGPAGRQDSAPVDPSSPHSY-NH$_2$ | (SEQ ID NO: 62) |
| Pal-KGCRFGTCTVQKLAHQIYQFTDKDKDNVAPRSKSSPHSY-NH$_2$ | (SEQ ID NO: 63) |
| Pal-KGCRFGTCTVQKLAHLWQLMGPAGRQDSAPVDPSSPHSY-NH$_2$ | (SEQ ID NO: 64) |
| Ace-K(PAL)GCRFGTCTVQKLAHQIYQFTDKDKDNVAPRSKSSPHSY-NH$_2$ | (SEQ ID NO: 65) |
| Ace-K(PAL)GCRFGTCTVQKLAHLWQLMGPAGRQDSAPVDPSSPHSY-NH$_2$ | (SEQ ID NO: 66) |
| Pal-CRFGTCTVQKLAHQIYQFTDKDKDNSAPVDPSSPHSY-NH$_2$ | (SEQ ID NO: 67) |
| miniPEG-K(PAL)GCRFGTCTVQKLAHQIYQFTDKGRQDSAPVDPSSPHSY-NH$_2$ | (SEQ ID NO: 68) |
| Ace-KGCRFGTCTVQKLAHQIYQFTDKDSAPVDPSSPHSY-NH$_2$ | (SEQ ID NO: 93) |
| Pal-ACDTATCVTHRLAGLLSRFTDKDKDNVAPRSKISPQGY-NH$_2$ | (SEQ ID NO: 104) |
| Pal-FGCRFGTCTVQKLAHRLWQLMGPDKDNVAPRSKISPQGY-NH$_2$ | (SEQ ID NO: 105) |
| Pal-ACDTATCVTHRLAGLLSRSGGVNFVPTNVGSKAF-NH$_2$ | (SEQ ID NO: 108) |

CLR/RAMP2-specific superagonist peptide sequence

| | |
|---|---|
| miniPEG-K(PAL)GCRFGTCTVQKLAHQIYQFTDKDKDNVAPRSKISPQGY-NH$_2$ | (SEQ ID NO: 69) |
| miniPEG-K(PAL)TKKTLRTGCRFGTCTVQKLAHQIYQFTDKDKDNVAPRSKISPQGY-NH$_2$ | (SEQ ID NO: 70) |

TABLE 1-continued

List of synthetic CLR/RAMP receptor agonist and antagonist sequences

| Sequence | SEQ ID NO |
|---|---|
| miniPEG-K(PAL)GCRFGTCTVQKLAHQIYQFTDKDKDNVDPSSPHSY-NH$_2$ | 94 |
| miniPEG-K(PAL)GCRFGTCTVQKLAHQIYQFTDKDVAPRSKISPQGY-NH$_2$ | 101 |
| Pal-KGCRFGTCTVQKLAHQIYQFTDKDVAPRSKISPQGY-NH$_2$ | 103 |
| Pal-KGCRFGTCTVQKLAHQIYQFTDKDAPVDPSSPHSY-NH$_2$ | 110 |

Low potency CLR/RAMP1- or CLR/RAMP2-specific peptide sequence

| Sequence | SEQ ID NO |
|---|---|
| Pal-GCRFGTCTVQKLAHQIYQFTDKDKDNVAPRSKISPQGY-NH$_2$ | 71 |
| Pal-YRQSMNNFQGLRSFGCRFGTCTVQKLAHQIYQFTDKDKDNVAPRSKISPQGY-NH$_2$ | 72 |
| Pal-K(Pal)GCRFGTCTVQKLAHQIYQFTDKDKDNVAPRSKISPQGY-NH$_2$ | 73 |
| Ace-K(Pal)GCDTATCVTHRLAGLLSRSGGVVKNNFVPTNVGSKAF-NH$_2$ | 74 |

Pan-specific super-antagonist peptide sequence

| Sequence | SEQ ID NO |
|---|---|
| Pal-TVQKLAHQIYQFTDKDKDNSAPVDPSSPHSY-NH$_2$ | 77 |
| miniPEG-K(Pal)VQKLAHQIYQFTDKDKDNSAPVDPSSPHSY-NH$_2$ | 78 |
| MiniPEG-K(Pal)VQKLAHQIYQFTDKDSAPVDPSSPHSY-NH$_2$ | 112 |
| Pal-KVQKLAHQIYQFTDKDSAPVDPSSPHSY-NH$_2$ | 121 |
| Pal-KVQKLAHQIYQFTDKSAPVDPSSPHSY-NH$_2$ | 125 |

Wild type antagonistic peptide sequence

| Sequence | SEQ ID NO |
|---|---|
| Ace-TVQKLAHQIYQFTDKDKDNVAPRSKISPQGY-NH$_2$ | 75 |
| Ace-VTHRLAGLLSRSGGVVKNNFVFINVGSKAF-NH$_2$ | 137 |

Low potency antagonistic peptide sequence

| Sequence | SEQ ID NO |
|---|---|
| Ace-TVQKLAHQIYQFTDKDKDNSAPVDPSSPHSY-NH$_2$ | 76 |
| Ace-VTHRLAGLLSRFTDKDKDNVAPRSKISPQGY-NH$_2$ | 115 |
| Ace-TVQKLAHRLWQLMGPDKDNVAPRSKISPQGY-NH$_2$ | 116 |
| Pal-VTHRLAGLLSRFTDKDKDNVAPRSKISPQGY-NH$_2$ | 117 |
| Pal-TVQKLAHRLWQLMGPDKDNVAPRSKISPQGY-NH$_2$ | 118 |

CLR/RAMP1-specific super-antagonist peptide sequence

| Sequence | SEQ ID NO |
|---|---|
| MiniPEG-K(Pal)VQKLAHQIYSAPVDPSSPHSY-NH$_2$ | 114 |
| Pal-KVQNLSHRLWQLMGPAGSAPVDPSSPHSY-NH$_2$ | 120 |
| Pal-KVQKLAHQIYSAPVDPSSPHSY-NH$_2$ | 122 |
| Pal-KVQKLAHQISAPVDPSSPHSY-NH$_2$ | 123 |
| Pal-KVQKLAHQSAPVDPSSPHSY-NH$_2$ | 124 |
| Pal-KVQKLSAPVDPSSPHSY-NH$_2$ | 139 |

CLR/RAMP2-specific super-antagonist peptide sequence

| Sequence | SEQ ID NO |
|---|---|
| Pal-KVQKLAHQIYQFTDKDVAPRSKISPQGY-NH$_2$ | 119 |

Preparation of Peptides and Peptidomimetics

Solid Phase Synthesis. The CLR/RAMP receptor super-agonists, agonists, suerantagonists and antagonists described herein can be prepared by classical methods known in the art, for example, by using standard solid phase techniques. See, for example, Merrifield, 1963 *J. Am. Chem. Soc.* 85:2149. These solid phase peptide synthesis procedures are well known in the art and further described by J. M. Stewart and J. D. Young, 1984 *Solid Phase Peptide Syntheses* 2nd Ed., Pierce Chemical Company.

Synthetic Amino Acids. These procedures can also be used to synthesize peptides in which amino acids other than the 20 naturally occurring, genetically encoded amino acids are substituted at one, two, or more positions of any of the peptides of the invention as disclosed herein. For instance, naphthylalanine can be substituted for tryptophan, facilitating synthesis. Other synthetic amino acids that can be substituted into the peptides of the present embodiments include L-hydroxypropyl, L-3,4-dihydroxy-phenylalanyl, d amino acids such as L-d-hydroxylysyl and D-d-methylalanyl, L-α-methylalanyl, β-amino acids, and isoquinolyl. D amino acids and non-naturally occurring synthetic amino acids can also be incorporated into the peptides of the present embodiments (see, for example, Roberts, et al. 1983 *Unusual Amino/Acids in Peptide Synthesis* 5:341-449).

In some embodiments, the naturally occurring side chains of the 20 genetically encoded amino acids, or any other side chain as disclosed herein can be transposed to the nitrogen of the amino acid, instead of the α-carbon as typically found in peptides.

In some embodiments, the amino acid sequence of a CLR/RAMP receptor superagonist can be modified, relative to the sequence of SEQ ID NOS: 28-51, 69-70, 92, 94, 101, 103, and 110 such that the modification reduces the susceptibility to enzymatic proteolysis. In some embodiments this modification comprises N-terminal addition of a sequence comprising all or part of the human serum albumin or immunoglobulin proteins. In some embodiments, peptides of the invention comprise one or more D-amino acid residues. In some embodiments, the amino acid sequence of a peptide of the invention is modified, relative to the sequence of SEQ ID NOS: 28-51, 69-70, 92, 94, 101, 103, and 110, such that the modification includes replacement of one or more L-amino acids residues with corresponding D-amino acids residues.

In some embodiments, the amino acid sequence of peptides of the invention are modified, relative to the sequence of SEQ ID NOS: 28-51, 69-70, 92, 94, 101, 103, and 110 such that the modification is substitution of one or more amino acids with a conservative amino acid.

Naturally occurring residues may be divided into classes based on common side chain properties:
hydrophobic: norleucine (Nor), Met, Ala, Val, Leu, De;
neutral hydrophilic: Cys, Ser, Thr, Asn, Gln;
acidic: Asp, Glu;
basic: His, Lys, Arg;
residues that influence chain orientation: Gly, Pro; and
aromatic: Trp, Tyr, Phe.

Conservative amino acid substitutions may involve exchange of a member of a class with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acids.

In some embodiments, conservative substitutions can include the substitution of one non-polar (hydrophobic) amino acid residue such as isoleucine, valine, leucine norleucine, alanine, or methionine for another, the substitution of one polar (hydrophilic) amino acid residue for another such as between arginine and lysine, between glutamine and asparagine, between threonine and serine, the substitution of one basic amino acid residue such as lysine, arginine or histidine for another, or the substitution of one acidic residue, such as aspartic acid or glutamic acid for another (Table 3). The phrase "conservative amino acid substitution" also includes the use of a chemically derivatized residue in place of a non-derivatized residue, provided that such polypeptide displays the requisite agonist activity.

Examples of amino acid residue substitutions that can be useful in accordance with the present embodiments include the following:

| Original Residue | Substitutions |
|---|---|
| Ala | Val, Leu, Ile, Aib |
| Arg | Lys, Gln, Asn, homoarginine |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, 1,4-Diamino-butyric Acid, Gln, Asn, ornithine |
| Met | Leu, Phe, Ile |
| Phe | Leu, Val, Ile, Ala, Tyr |
| Pro | Ala |
| Ser | Thr, Ala, Cys |
| Thr | Ser, Val, Ile |
| Trp | Tyr, Phe |
| Tyr | Trp, Phe, Thr, Ser |
| Val | Ile, Met, Leu, Phe, Ala, Norleucine |

In some embodiments, a basic moiety of an amino acid as disclosed herein, such as the guanidine of Arg, can be replaced by a base bioisostere.

One can also readily modify the peptides of the instant embodiments by other methods for making peptide derivatives of the compounds of the present embodiments are described in Hruby, et al. 1990 *Biochem. J.* 268:249-262. Thus, the peptides as disclosed herein also serve as a basis to prepare peptidomimetics with similar biological activity.

Terminal Modifications

Those of skill in the art recognize that a variety of techniques are available for constructing peptidomimetics with the same or similar desired biological activity as the corresponding CLR/RAMP receptor superagonist but with more favorable activity than the reference peptide with respect to solubility, stability, and susceptibility to hydrolysis and proteolysis. See, for example, Morgan, et al. 1989 *Ann. Rep. Med. Chem.* 24:243-252. The following describes methods for preparing peptidomimetics modified at the N-terminal amino group, the C-terminal carboxyl group, and/or changing one or more of the amido linkages in the peptide to a non-amido linkage. It being understood that two or more such modifications can be coupled in one peptidomimetic structure (for example, modification at the C-terminal carboxyl group and inclusion of a —$CH_2$-carbamate linkage between two amino acids in the peptide).

N-Terminal Modifications

Peptides typically are synthesized as the free acid but, as noted above, could be readily prepared as the amide or ester. One can also modify the amino and/or carboxy terminus of the peptide compounds to produce other useful compounds. Amino terminus modifications include methylation (i.e., —$NHCH_3$ or —$NH(CH_3)_2$), acetylation, adding a benzyloxycarbonyl group, or blocking the amino terminus with any blocking group containing a carboxylate functionality defined by RCOO—, where R is selected from the group consisting of naphthyl, acridinyl, steroidyl, and similar groups.

Amino terminus modifications are as recited above and include alkylating, acetylating, adding a carbobenzoyl group, forming a succinimide group, etc. See, for example, Murray, et al. 1995 *Burger's Medicinal Chemistry and Drug Discovery* 5th ed., Vol. 1, Manfred E. Wolf, ed., John Wiley and Sons, Inc.

The N-terminus may also be modified through the addition of at least one residues N-terminal to the $B^a$ fragment. Techniques for assessing the impact of N-terminal extensions to peptides are known in the art in, for example, Schellenberger, et al., 2009, *Nature Biotechnology* 27(12): 1186-1192.

C-Terminal Modifications

Carboxy terminus modifications include replacing the free acid with a carboxamide group or forming a cyclic lactam at the carboxy terminus to introduce structural constraints. In preparing peptidomimetics wherein the C-terminal carboxyl group is replaced by the amide —$C(O)NR^3R^4$, a benzhydrylamine resin is used as the solid support for peptide synthesis. Upon completion of the synthesis, hydrogen fluoride treatment to release the peptide from the support results directly in the free peptide amide (i.e., the C-terminus is —$C(O)NH_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide. Side chain protection is then removed in the usual fashion by treatment with hydrogen fluoride to give the free amides, alkylamides, or dialkylamides.

In addition to the foregoing N-terminal modifications, the modified peptide agonists described herein, including peptidomimetics, can advantageously be modified with or covalently coupled to one or more of a variety of hydrophilic polymers. It has been found that when the peptide compounds are derivatized with a hydrophilic polymer, their solubility and circulation half-lives are increased and their immunogenicity is masked. In some embodiments, the CLR/RAMP receptor superagonists as disclosed and described herein can be derivatized with or coupled to such polymers using any of the methods set forth in Zallipsky, S. 1995 *Bioconjugate Chem* 6:150-165; Monfardini, C, et al. 1995 *Bioconjugate Chem* 6:62-69.

Backbone Modifications

Other methods for making peptide derivatives of the compounds are described in Hruby, et al. 1990 *Biochem. J.* 268(2):249-262. Thus, the peptide compounds also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis. See Morgan, et al. 1989 *Ann. Rep. Med. Chem.* 24:243-252, incorporated herein by reference in its entirety.

Disulfide Bond Formation

The compounds may exist in a cyclized form with one or more intramolecular disulfide bond between the thiol groups of the cysteines.

Other embodiments include analogs of these disulfide derivatives in which one of the sulfurs has been replaced by a $CH_2$ group or other isostere for sulfur. These analogs can be made via an intramolecular or intermolecular displacement, using methods known in the art.

Alternatively, the amino-terminus of the peptide can be capped with an alpha-substituted acetic acid, wherein the alpha substituent is a leaving group, such as an α-haloacetic acid, for example, α-chloroacetic acid, α-bromoacetic acid, or α-iodoacetic acid. The peptides of the present embodiments can be cyclized or dimerized via displacement of the leaving group by the sulfur of the cysteine or homocysteine residue. See, for example, Andreu, et al. 1994, *Meth. Mol. Bio.* 35(7):91-169.

In some embodiments, the peptides of the invention as disclosed and described herein as well as their fusion proteins may also be prepared by recombinant DNA techniques well known in the art. The fusion proteins may include, but are not limited to, those with human serum albumin, immunoglobulin, Fc, Fc derivatives, microglobulin, or other serum proteins.

Other Utility

The compounds described herein can be used as reagents for selectively detecting CLR/RAMP receptors on living cells, fixed cells, in biological fluids, in tissue homogenates, in human bodies, etc. An antibody that specifically binds to one or more of the peptides described herein can be generated by methods known to one of skill in the art, which antibody may be used, for example, in the detection and analysis of the peptides described herein.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Based on evidence that CLR/RAMP receptors modulates a number of central nervous system (CNS) and peripheral vascular activities, many analogs of adrenomedullin, CGRPs and intermedin have been synthesized and studied. Thus far, known synthetic analogs of these peptide hormones exhibit receptor-activation activities either comparative or inferior to wild type ligands. Likewise, synthetic antagonistic analogs of these peptide hormones (e.g., CGRP8-37 and ADM22-52; Rovero, P. et al. 1992, *Peptides* 13:1025-1027) exhibit mild bioactivities and are mainly specific for one of the three CLR/RAMP receptors (i.e., CLR/RAMP1, 2, and 3 receptors). No pan-specific superagonist or antagonist as well as CLR/RAMP2-specific superagonist is present.

In humans and other mammals, including rodents, there are three CLR/RAMP receptors for adrenomedullin, CGRPs, and intermedin. These are CLR/RAMP1, 2, and 3 receptors, which are expressed throughout the vascular system. It has been reported that CGRPs are selective agonists for CLR/RAMP1 whereas adrenomedullin interact with high affinity with CLR/RAMP2. On the other hand, intermedin is a low potency ligand and does not exhibit specific preference among CLR/RAMP1, 2, and 3 receptors. Given the interesting physiological and pharmacology characteristics of these peptide hormones, we sought to identify ligands that exhibit superior agonistic or antagonistic activity toward both CLR/RAMP1 and 2 receptors as well as ligands that exhibit superior agonistic activity toward CLR/RAMP2 receptor. We designed and synthesized a series of systematically modified derivatives of adrenomedullin and intermedin, and characterized their signaling in comparison with the parent compounds. Findings indicate that activities of chimeric analogs with N-terminal acylation together with or without mini-PEG modification are significantly superior to the physiological transmitters, CGRP, ADM, or IMD. In addition, adrenomedullin analog with both N-terminal acylation and mini-PEG modifications exhibit superagonistic activity toward CLR/RAMP2 receptors specifically.

In addition, molecule comprising the sequence of ADM and IMD was shown to compete for CGRP and ADM interaction with CLR/RAMP1, 2, and/or 3 receptors with high potency when compared to general CLR/RAMP1 receptor antagonist CGRP8-38 and/or CLR/RAMP2 receptor antagonist ADM22-52. Also, select superantagonistic analogs exhibit CLR/RAMP1- or CLR/RAMP2-specific antagonistic activities. The analog thus represents a pan-specific or selective superantagonist which binds to its complementary biologically active receptor and inhibits the physiological response of the receptor stronger than the physiological ligands.

EXAMPLE 1

Using a receptor activation assay, the dose-dependent stimulatory response of peptide agonists of the present invention on a CLR/RAMP1 receptor, a CLR/RAMP2, or a CLR/RAMP3 receptor complex was determined. A cell line carrying the recombinant CLR/RAMP1, CLR/RAMP2, or a CLR/RAMP3 receptor was employed in the assay. Peptide agonist activities were tested, in duplicate, at 10 different concentrations, starting with 1.0 µM and serially diluted 3-fold, in DMSO. Human β-CGRP, a known CLR/RAMP1 receptor agonist, was used as a positive control in the CLR/RAMP1 assays, and ADM, a known CLR/RAMP2 receptor agonist was used as a positive control in the CLR/RAMP2 assays. The CLR/RAMP1 cAMP, CLR/RAMP2 arrestin assays, and CLR/RAMP3 cAMP (DiscoveRx, Fremont, Calif.) were used. The assays were performed in duplicate at a single concentration, and EC50 and IC50 determinations were performed in duplicate using 10 point dose response curves, 3-fold dilutions at a starting concentration.

Results

The pharmacology of superagonistic activity of synthetic analogs was studied in cells stably express CLR/RAMP1 (1321N1 cells), CLR/RAMP2 (CHO-K1 cells), or CLR/RAMP3 (CHO-K1 cells) receptors. In receptor activation assays using 0.03-1000 nM doses of wild type ligands and modified analogs, the half-maximally effective concentration ($EC_{50}$) of adrenomedullin in CLR/RAMP2 receptor is approximately 13-26 nM, and the $EC_{50}$ of CLR/RAMP1-specific β-CGRP in CLR/RAMP1 receptor is approximately 1-1.5 nM (Table 2).

Additional control of wild-type ADM peptides (SEQ ID NOS: 53 and 54) and IMD peptide (SEQ ID NO: 52) showed that these peptides are low potency ligands for CLR/RAMP1 receptor. The $EC_{50}$ for the wild-type ADM peptides are between 9-12 nM whereas the $EC_{50}$ for wild-type IMD was 70 nM. Comparison of the bioactivity of synthetic analogs showed that six principle chimeric peptides of ADM and IMD (SEQ ID NOS: 55-60) have low potency or are inactive in stimulating CLR/RAMP1 and/or CLR/RAMP2 receptors.

Surprisingly, a mini-PEG and a palmitoylation modifications at the N-terminus of select peptides (SEQ ID NOS: 28-29) increased the potency of these peptides by 10 to 1000 folds. Additional testing showed that select modification with palmitoylation in these peptides and additional chimeric peptides also led to significant increases in potency (SEQ ID NOS: 30-51 and 92). The $EC_{50}$ for stimulating CLR/RAMP1 and 2 receptors by most of these synthetic peptides are at high picomolar ranges (i.e., <1 nM).

Importantly, several of these synthetic peptides (SEQ ID NOS: 28, 30, 31, 34, and 36) also exhibited a >110% maximum activity in CLR/RAMP2 receptor when compared to adrenomedullin. In addition, some of these potent agonistic peptides represent miniaturized agonists. For example, SEQ ID NOS: 48 and 92 contain only 36 amino acids, which are much smaller than the 39- or 40-amino-acid wild type peptides. Furthermore, some of these agonistic peptides also exhibit superagonistic activities toward CLR/RAMP3. While the $EC_{50}$ of ADM for CLR/RAMP receptor was approximately 0.4 nM (Table 2), the $EC_{50}$ of SEQ ID NOS: 28 and 48 were 0.06-0.07 nM. These data thus suggested that these synthetic agonists are pan-specific superagonists for CLR/RAMP1, 2, and/or 3 receptors.

The increases in potency for these synthetic ligands are specific and unique to these ligands. Other chimeric peptides with the N-terminal mini-PEG and/or palmitoylation modifications (SEQ ID NOS: 61-68), nonacylated truncated chimeric peptide (SEQ ID NO: 93), acylated chimeric CGRP-ADM peptide (SEQ ID NO: 104), acylated chimeric ADM-IMD-ADM peptide (SEQ ID NO: 105), and acylated truncated CGRP (SEQ ID NO: 108) did not exhibit increases in potency for CLR/RAMP1 and 2 receptors.

Taking advantage of these observations, we then sought to identify superagonist that is selective for CLR/RAMP2 receptor, and tested additional synthetic analogs (SEQ ID NOS: 71-74). The results showed that a palmitoylation modification of CGRP (SEQ ID NO: 74) did not affect the characteristics of CGRP activity. Likewise, palmitoylation at the N-terminus of ADM peptides with different lengths (SEQ ID NOS: 71-73) only moderately increased the potency of these peptides on CLR/RAMP1 and 2 receptors. By contrast, a specific modification with both a mini-PEG motif and a palmitoylation (SEQ ID NO: 69-70) of ADM peptide decreased the $EC_{50}$ to low nanomolar or subnanomolar concentration and maintained a preference for CLR/RAMP2 receptor. We also showed that the mini-PEG and palmitoylation modification of ADM (SEQ ID NO: 69) increases the maximum activity of CLR/RAMP2 receptor to 147%. In addition, we discovered that select ADM and chimeric analogs with truncation in the middle of the sequences generated miniaturized CLR/RAMP2-specific analogs (SEQ ID NOS: 94, 101, 103, and 110). These data show that these ligands represent CLR/RAMP2-specific superagonists.

The results of these experiments with the positive control values are listed in Table 2. The results demonstrate the surprisingly high potency of the selected peptides, for example, many have $EC_{50}$ concentrations in the high picomolar range compared to the high nanomolar $EC_{50}$ concentration of wild type-peptides.

These findings suggested that these superagonists are more efficacious agonists than wild type ligands in stimulating cellular functions. Indeed, functional tests using cultured human lymphatic endothelial cells (HLEC) showed that these superagonists exhibited a higher intrinsic efficacy than wild type ADM and IMD in stimulating HLEC cell survival and proliferation. Quantification of cell survival and proliferation using MTS assay showed that synthetic analogs (SEQ ID NO: 28, 30, 33, 38, 39, 40, and 69) dose-dependently stimulated HLEC cell proliferation and survival at 30-100 nM range (FIGS. 1 and 2). By contrast, wild-type ADM (SEQ ID NOS: 53 and 54), wild-type IMD (SEQ ID NO: 52), and a principle chimeric peptide (SEQ ID NO: 59) have minimal effects on HLEC cell proliferation and survival at this dosage range (FIGS. 1 and 2). These data thus demonstrated the relative intrinsic efficacies of these novel analogs are superior to known CLR/RAMP receptor ligands in stimulating receptor signaling and the receptor-mediated cell survival and proliferation.

TABLE 2

List of agonistic activity of synthetic CR/RAMP receptor agonists

| | Identity | | | | | |
|---|---|---|---|---|---|---|
| | CLR/RAMP1 | | CLR/RAMP2 | | CLR/RAMP3 | |
| | EC50 (nM) | Max Activity % of positive control | EC50 (nM) | Max Activity % of positive control | EC50 (nM) | Max Activity % of positive control |
| Wild type ADM positive | | | 13-26 | 100 | 0.4 | 104 |
| Wild type CGRP-β positive | 1-1.5 | 100 | | | | |
| Pan-specific superagonists | | | | | | |
| (SEQ ID NO: 28) | 0.3 | 54 | 0.5 | 143 | 0.06 | 117 |
| (SEQ ID NO: 29) | 3 | 54 | 3 | 94 | | |
| (SEQ ID NO: 30) | 0.4 | 51 | 0.6 | 126 | | |
| (SEQ ID NO: 31) | 0.8 | 47 | 0.9 | 110 | | |
| (SEQ ID NO: 32) | 0.5 | 48 | 1 | 119 | | |
| (SEQ ID NO: 33) | 0.3 | 62 | 0.4 | 101 | | |
| (SEQ ID NO: 34) | 0.2 | 50 | 0.7 | 120 | | |
| (SEQ ID NO: 35) | 0.8 | 42 | 1 | 116 | | |
| (SEQ ID NO: 36) | 0.6 | 58 | 0.9 | 130 | | |
| (SEQ ID NO: 37) | 1.3 | 55 | 4 | 72 | | |
| (SEQ ID NO: 38) | 0.5 | 89 | 0.7 | 97 | | |
| (SEQ ID NO: 39) | 0.2 | 82 | 0.5 | 86 | | |
| (SEQ ID NO: 40) | 2 | 99 | 1 | 86 | | |
| (SEQ ID NO: 41) | 0.4 | 75 | 0.9 | 105 | | |
| (SEQ ID NO: 42) | 1.3 | 56 | 0.2 | 76 | | |
| (SEQ ID NO: 43) | 0.5 | 39 | 0.2 | 30 | | |
| (SEQ ID NO: 44) | 0.1 | 58 | 0.2 | 69 | | |
| (SEQ ID NO: 45) | 0.1 | 50 | 0.3 | 79 | | |
| (SEQ ID NO: 46) | 0.7 | 60 | 0.5 | 104 | | |
| (SEQ ID NO: 47) | 1.5 | 85 | 0.4 | 64 | | |
| (SEQ ID NO: 48) | 0.3 | 78 | 0.2 | 77 | 0.07 | 141 |
| (SEQ ID NO: 49) | 0.5 | 66 | 0.4 | 83 | | |
| (SEQ ID NO: 50) | 1.2 | 65 | 1.2 | 87 | | |
| (SEQ ID NO: 51) | 0.2 | 65 | 0.3 | 107 | | |
| (SEQ ID NO: 92) | 0.4 | 61 | 0.3 | 67 | 0.2 | 156 |
| Wild-type IMD, ADM, and CGRP | | | | | | |
| (SEQ ID NO: 52) | 116 | 72 | 70 | 67 | | |
| (SEQ ID NO: 53) | 540 | 69 | 9 | 102 | | |
| (SEQ ID NO: 54) | 564 | 63 | 12 | 91 | 2.2 | 130 |
| (SEQ ID NO: 143) | 1.8-2.9 | 103 | >1000 | | | |
| Inactive or low potency chimeric peptides | | | | | | |
| (SEQ ID NO: 55) | >1000 | 1 | >1000 | 8 | | |
| (SEQ ID NO: 56) | 224 | 58 | 17 | 111 | | |
| (SEQ ID NO: 57) | 909 | 53 | 149 | 94 | | |
| (SEQ ID NO: 58) | >1000 | 0 | >1000 | 1 | | |
| (SEQ ID NO: 59) | 31 | 95 | 18 | 115 | | |
| (SEQ ID NO: 60) | 16 | 100 | 3 | 114 | | |
| (SEQ ID NO: 61) | 175 | 70 | 6 | 92 | | |
| (SEQ ID NO: 62) | >1000 | 2 | >1000 | 8 | | |
| (SEQ ID NO: 63) | 180 | 61 | 7 | 94 | | |
| (SEQ ID NO: 64) | >1000 | 1 | >1000 | 8 | | |
| (SEQ ID NO: 65) | 234 | 73 | 19 | 99 | | |
| (SEQ ID NO: 66) | >1000 | 4 | >1000 | 4 | | |
| (SEQ ID NO: 67) | 1 | 78 | >1000 | 77 | | |
| (SEQ ID NO: 68) | 11 | 48 | 7 | 70 | | |
| (SEQ ID NO: 93) | 771 | 53 | 17 | 85 | | |
| (SEQ ID NO: 104) | >1000 | 2 | >1000 | 4 | | |
| (SEQ ID NO: 105) | >1000 | 33 | 19 | 40 | | |
| (SEQ ID NO: 108) | >1000 | 6 | >1000 | 6 | | |
| CLR/RAMP2-specific superagonists | | | | | | |
| (SEQ ID NO: 69) | 13 | 70 | 0.6 | 147 | 0.6 | 127 |
| (SEQ ID NO: 70) | 619 | 69 | 1.1 | 68 | | |

TABLE 2-continued

List of agonistic activity of synthetic CR/RAMP receptor agonists

| | Identity | | | | | |
|---|---|---|---|---|---|---|
| | CLR/RAMP1 | | CLR/RAMP2 | | CLR/RAMP3 | |
| | EC50 (nM) | Max Activity % of positive control | EC50 (nM) | Max Activity % of positive control | EC50 (nM) | Max Activity % of positive control |
| (SEQ ID NO: 94) | 11 | 67 | 1.3 | 82 | | |
| (SEQ ID NO: 101) | 7.7 | 56 | 0.3 | 74 | 0.5 | 129 |
| (SEQ ID NO: 103) | 4.5 | 96 | 0.7 | 77 | 0.3 | 140 |
| (SEQ ID NO: 110) | 43 | 71 | 6.4 | 74 | | |
| Low potency CLR/RAMP1- or CLR/RAMP2-specific peptides | | | | | | |
| (SEQ ID NO: 71) | 24 | 53 | 3 | 78 | | |
| (SEQ ID NO: 72) | 28 | 45 | 3 | 90 | | |
| (SEQ ID NO: 73) | 34 | 79 | 49 | 46 | | |
| (SEQ ID NO: 74) | 2 | 95 | >1000 | 12 | | |

For the analysis of antagonistic activity, the synthetic analogs were pre-incubated with the cells before adding the reference ligand at its EC80. The assays showed that the wild type ADM22-52 (SEQ ID NO: 75) inhibited the CGRP-stimulated CLR/RAMP1 and ADM-stimulated CLR/RAMP2 receptor activation with IC50 of >20000 and 631 nM, respectively (Table 3). On the other hand, the CLR/RAMP1-specific CGRP8-37 (SEQ ID NO: 137) has an $IC_{50}$ of 133 and >10000 nM, for CLR/RAMP1 and CLR/RAMP3, respectively.

These data are consistently with the literature that CGRP8-37 and ADM22-52 are low potency antagonists specific for CLR/RAMP1 and CLR/RAMP2, respectively. The chimeric peptide consist of ADM and IMD sequence (SEQ ID NO: 76) appear to have mildly improved antagonistic activity toward CLR/RAMP1 and 2 receptors. The $IC_{50}$ for CGRP-stimulated CLR/RAMP1 and ADM-stimulated CLR/RAMP2 receptor signaling was 1123 and 289 nM, respectively. By contrast, the chimeric peptide with an N-terminal palmitoylation, or a palmitoylation and mini-PEG modification (SEQ ID NOS: 77-78, 112, 114, 119, 120-125, or 139) exhibited highly potent antagonistic activity toward CGRP-stimulated CLR/RAMP1 and/or ADM-stimulated CLR/RAMP2 receptor signaling.

Among these antagonists, SEQ ID NOS: 77-78, 112, 121, and 125 are pan-specific. SEQ ID NOS: 114, 120, 122-124, and 139 are CLR/RAMP1-specific; whereas SEQ ID NO: 119 is CLR/RAMP2-specific. The $IC_{50}$ for CGRP-stimulated CLR/RAMP1 and ADM-stimulated CLR/RAMP2 receptor signaling for these analogs was 1.8-9.9 and 0.6-47 nM, respectively. On the other hand, two synthetic peptides that have been reported to exhibit potent antagonistic activities for CLR/RAMP receptors (SEQ ID NOS: 115 and 116; Table 3) did not show superantagonistic activities in the same assays. Moreover, studies of the CLR/RAMP3 receptor-activation activities showed that select peptides are superagonists for CLR/RAMP3 as well. Unlike CGRP8-37 and ADM22-52, which have an $IC_{50}$ of 574 and 330 nM for CLR/RAMP3, respectively; the $IC_{50}$ of SEQ ID NOS: 78, 112, 114, 119, 120-122, and 123 were 0.8-9.2 nM. It is also important to note that some of these superantagonists are miniaturized antagonists which contain only 17-28 amino acids. The CGRP8-37 and ADM22-52 contain 30 and 31 amino acids, respectively.

These data indicated that the N-terminally modified chimeric peptides (SEQ ID NOS: 77-78, 112, 114, 119, 120-125, or 139) have antagonistic activities one to two orders of magnitude stronger than the parental peptide (SEQ ID NO: 76), or CGRP- and ADM-derived antagonists. Therefore, these modified chimeric or truncated peptides represent potent pan-specific, CLR/RAMP1-specific, or CLR/RAMP2-specific superantagnoists for CLR/RAMP1, 2, and 3 receptors.

TABLE 3

List of antagonistic activity of synthetic CLR/RAMP receptor antagonists

| | Identity | | | | | |
|---|---|---|---|---|---|---|
| | CLR/RAMP1 | | CLR/RAMP2 | | CLR/RAMP3 | |
| CLR/RAMP1 antagonist | IC50 (nM) | Max Activity % of positive control | IC50 (nM) | Max Activity % of positive control | IC50 (nM) | Max Activity % of positive control |
| BIBN4096 Pan-specific super-antagonist | 0.05 | 105 | >100 | 0 | | |
| (SEQ ID NO: 77) | 9.9 | 101 | 47 | 100 | | |
| (SEQ ID NO: 78) | 4.8 | 104 | 34 | 107 | 0.8 | 101 |

TABLE 3-continued

List of antagonistic activity of synthetic CLR/RAMP receptor antagonists

| CLR/RAMP1 antagonist | CLR/RAMP1 | | CLR/RAMP2 | | CLR/RAMP3 | |
|---|---|---|---|---|---|---|
| | IC50 (nM) | Max Activity % of positive control | IC50 (nM) | Max Activity % of positive control | IC50 (nM) | Max Activity % of positive control |
| (SEQ ID NO: 112) | 1.8 | 99 | 5.3 | 97 | 2.3 | 99 |
| (SEQ ID NO: 121) | 3.2 | 94 | 4.9 | 104 | 1.8 | 100 |
| (SEQ ID NO: 125) | 7 | 93 | 7.1 | 100 | | |
| ADM22-52 and CGRP8-37 | | | | | | |
| (SEQ ID NO: 75) | >20000 | 22 | 631 | 100 | 330 | 99 |
| (SEQ ID NO: 137) | 133 | 95 | >10,000 | 15 | 574 | 96 |
| Low potency antagonists | | | | | | |
| (SEQ ID NO: 76) | 1123 | 106 | 289 | 101 | | |
| (SEQ ID NO: 115) | 1878 | 99 | 117 | 100 | 115 | 98 |
| (SEQ ID NO: 116) | 152 | 101 | 7.3 | 101 | 53 | 98 |
| CLR/RAMP1-specifci super-antagonist | | | | | | |
| (SEQ ID NO: 114) | 4.8 | 101 | 146 | 87 | 8.4 | 102 |
| (SEQ ID NO: 120) | 5.8 | 94 | 85 | 98 | 9.2 | 100 |
| (SEQ ID NO: 122) | 7.3 | 95 | 61 | 100 | 4.1 | 100 |
| (SEQ ID NO: 123) | 4.7 | 94 | 50 | 101 | | |
| (SEQ ID NO: 124) | 6.7 | 95 | 64 | 103 | 5.9 | 102 |
| (SEQ ID NO: 139) | 3.8 | 98 | 462 | 101 | | |
| CLR/RAMP2-specifci super-antagonist | | | | | | |
| (SEQ ID NO: 119) | 21 | 95 | 0.6 | 101 | 1.5 | 102 |

While the present embodiments have been described in some detail for purposes of clarity and understanding, one skilled in the art will appreciate that various changes in form and detail can be made without departing from the true scope of the embodiments. All figures, tables, and appendices, as well as patents, applications, and publications, referred to above, are hereby incorporated by reference in their entirety.

Control Reagents. Human β-CGRP and human ADM were employed as positive controls, respectively. In addition, peptides having the sequences (human IMD, SEQ ID NO: 52), (human ADM, SEQ ID NO: 53), and (human ADM, SEQ ID NO: 54) were employed as additional controls.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in protein structure without affecting the biological action in kind or amount. All such modifications are intended to be included within the scope of the appended claims.

What is claimed is:

1. A CLR/RAMP receptor agonist peptide, comprising a structure of Formula I:

$$B^a—C^a\text{-}D^a \qquad (I)$$

wherein $B^a$ is SEQ ID NO:13
$C^a$ is a central core consist of 3-12 amino acids; and
$D^a$ is SEQ ID NO:27, SSPHSY-NH$_2$.

2. The agonist of claim 1 wherein the central core $C^a$ comprises a fragment of human adrenomedullin or intermedin.

3. The agonist of claim 1 wherein the sequence of $C^a$ has a sequence selected from SEQ ID NO:18-26.

4. The agonist of claim 1, wherein the sequence of $C^a$ has at least 60% sequence identity to a sequence selected from SEQ ID NO:18-26.

5. The agonist of claim 1, wherein the sequence of $C^a$ has at least 80% sequence identity to a sequence selected from SEQ ID NO:18-26.

6. The agonist of claim 1, wherein the sequence of $C^a$ has at least 90% sequence identity to a sequence selected from SEQ ID NO:18-26.

7. A CLR/RAMP receptor agonist peptide, comprising an amino acid sequence of SEQ ID NO:43.

* * * * *